(12) United States Patent
Del Poeta et al.

(10) Patent No.: US 11,390,580 B2
(45) Date of Patent: Jul. 19, 2022

(54) ANTI-FUNGALS TARGETING THE SYNTHESIS OF FUNGAL SHINGOLIPIDS

(71) Applicants: Maurizio Del Poeta, Mount Sinai, NY (US); Visesato Mor, Nagaland (IN)

(72) Inventors: Maurizio Del Poeta, Mount Sinai, NY (US); Visesato Mor, Nagaland (IN)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 16/450,772

(22) Filed: Jun. 24, 2019

(65) Prior Publication Data
US 2020/0062698 A1 Feb. 27, 2020

Related U.S. Application Data

(63) Continuation of application No. 15/534,353, filed as application No. PCT/US2015/064278 on Dec. 7, 2015, now abandoned.
(Continued)

(51) Int. Cl.
C07C 251/86 (2006.01)
A61K 45/06 (2006.01)
(Continued)

(52) U.S. Cl.
CPC ............ *C07C 251/86* (2013.01); *A01N 37/28* (2013.01); *A61K 31/16* (2013.01); *A61K 31/166* (2013.01);
(Continued)

(58) Field of Classification Search
None
See application file for complete search history.

(56) References Cited

U.S. PATENT DOCUMENTS 5,306,712 A 4/1994 Tobitsuka
5,786,374 A 7/1998 Farooq
(Continued)

FOREIGN PATENT DOCUMENTS

DE 1 101 145 3/1961
GB 930988 A 7/1963
(Continued)

OTHER PUBLICATIONS

Lazzarini ("Acylhydrazones as Antifungal Agents Targeting the Synthesis of Fungal Sphingolipids" Antimicrobial Agents and Chemotherapy, published on Mar. 5, 2018, 62:e00156-18, including supplemental information (SI)) (Year: 2018).*
(Continued)

*Primary Examiner* — Amy C Bonaparte
(74) *Attorney, Agent, or Firm* — Gary J. Gershik

(57) ABSTRACT

The present invention provides a compound having the structure:
(Continued)

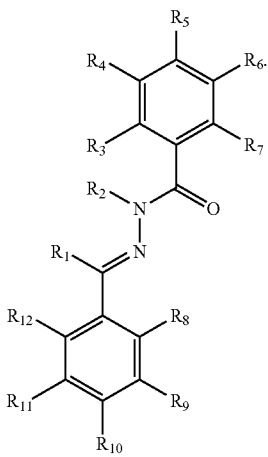

13 Claims, 42 Drawing Sheets

| | | | |
|---|---|---|---|
| 10,570,124 | B2 | 2/2020 | Radu |
| 10,646,577 | B2 | 5/2020 | Shokat |
| 10,696,634 | B2 | 6/2020 | Grammenos |
| 10,906,897 | B2 | 2/2021 | Quaranta |
| 10,947,205 | B2 | 3/2021 | Mandal |
| 10,947,237 | B2 | 3/2021 | Bhattacharjee |
| 10,952,436 | B2 | 3/2021 | Quaranta |
| 11,014,889 | B2 | 5/2021 | Hoffman |
| 11,053,205 | B2 | 7/2021 | Huigens |
| 11,064,697 | B2 | 7/2021 | Grammenos |
| 2012/0010075 | A1* | 1/2012 | Young ............... A01N 59/20 |
| | | | 504/101 |
| 2018/0141897 | A1 | 5/2018 | Del Poeta et al. |

FOREIGN PATENT DOCUMENTS

| | | | | |
|---|---|---|---|---|
| WO | WO 2008/137128 | A2 | 11/2008 | |
| WO | WO 2010/083307 | A2 | 7/2010 | |
| WO | WO 2012/027548 | | 3/2012 | |
| WO | WO-2012027548 | A1 * | 3/2012 | ........... A61K 31/166 |
| WO | WO 2013/071001 | A1 | 5/2013 | |
| WO | WO-2014204859 | A2 * | 12/2014 | ........... A61K 31/496 |
| WO | WO 2016/094307 | A1 | 6/2016 | |
| WO | WO 2016/160552 | A1 | 10/2016 | |
| WO | WO 2018/232298 | | 12/2018 | |
| WO | WO-2018232298 | A1 * | 12/2018 | ........... C07D 239/30 |

Related U.S. Application Data

(60) Provisional application No. 62/192,459, filed on Jul. 14, 2015, provisional application No. 62/088,914, filed on Dec. 8, 2014.

(51) Int. Cl.
*A61K 31/16* (2006.01)
*A61K 31/7072* (2006.01)
*A61K 38/12* (2006.01)
*A61K 31/7048* (2006.01)
*A61K 31/4196* (2006.01)
*A01N 37/28* (2006.01)
*A61K 31/166* (2006.01)

(52) U.S. Cl.
CPC ...... *A61K 31/4196* (2013.01); *A61K 31/7048* (2013.01); *A61K 31/7072* (2013.01); *A61K 38/12* (2013.01); *A61K 45/06* (2013.01)

(56) References Cited

U.S. PATENT DOCUMENTS

| | | | |
|---|---|---|---|
| 5,922,710 | A | 7/1999 | Muller |
| 5,932,583 | A | 8/1999 | Ziegler |
| 6,211,240 | B1 | 4/2001 | Zurfluh |
| 6,232,339 | B1 | 5/2001 | Gypser |
| 7,504,362 | B2 | 3/2009 | Döller et al. |
| 7,943,774 | B2 | 5/2011 | Cristau |
| 8,063,063 | B2 | 11/2011 | Sutton |
| 8,124,616 | B2 | 2/2012 | Frechette |
| 8,299,262 | B2 | 10/2012 | Grammenos |
| 9,029,549 | B2 | 5/2015 | Cristau |
| 9,108,958 | B2 | 8/2015 | Ebel |
| 9,215,875 | B2 | 12/2015 | Cristau |
| 9,221,827 | B2 | 12/2015 | Duffy |
| 9,221,841 | B2 | 12/2015 | Hans |
| 9,586,969 | B2 | 3/2017 | Bou Hamdan |
| 9,730,447 | B2 | 8/2017 | Bereznak |
| 9,896,454 | B2 | 2/2018 | Quaranta |
| 10,098,350 | B2 | 10/2018 | Bereznak |
| 10,221,171 | B2 | 3/2019 | Gestwicki |
| 10,266,544 | B2 | 4/2019 | Lee |
| 10,314,820 | B2 | 6/2019 | Önder |
| 10,407,435 | B2 | 9/2019 | Shuttleworth |
| 10,450,279 | B2 | 10/2019 | Grammenos |

OTHER PUBLICATIONS

Li ("Synthesis and structures of two molybdenum(VI)complexes derived from similar benzohydrazone ligands with catalytic properties" Journal of Coordination Chemistry, published on Mar. 31, 2014, vol. 67, issue 6, p. 1022-1031) (Year: 2014).*
https://www.drugs.com/inactive/methyl-alcohol-457.html, downloaded Jun. 19, 2020 (Year: 2020).*
Registry No. 316132-97-5, entered into STN on Jan. 23, 2001 by Chemical Library Supplier: MicroChemistry Ltd (Year: 2001).*
Registry No. 316137-31-2, entered into STN on Jan. 23, 2001 by Chemical Library Supplier: MicroChemistry Ltd (Year: 2001).*
https://www.drugs.com/inactive/acetone-180.html, downloaded on Jun. 19, 2020 (Year: 2020).*
Capriotti ("Dimethyl Sulfoxide: History, Chemistry, and Clinical Utility in Dermatology" The Journal of Clinical and Aesthetic Dermatology, 2012, vol. 5(9), p. 24-26) (Year: 2012).*
https://www.cas.org/support/documentation/chemical-substances/zerorefs, downloaded on Nov. 19, 2020 (Year: 2020).*
https://www.nature.com/subjects/chemical-libraries, downloaded on Nov. 19, 2020 (Year: 2020).*
https://en.wikipedia.org/wiki/Chemical_library (Year: 2020).*
STN registry file for the compound with registry No. 681000-38-4, entered into STN on May 10, 2004 by Chemical Library Supplier: Ambinter (Year: 2004).*
Chan ("A Method for Identifying Small-Molecule Aggregators Using Photonic Crystal Biosensor Microplates" JALA, 2009, p. 348-359) (Year: 2009).*
Zhao ("1,8-Naphthalimide-based 'turn-on' fluorescent sensor for the detection of zinc ion in aqueous media and its applications for bioimaging" Tet. Lett., 2013, 54, p. 3353-3358) (Year: 2013).*
Yuan ("Syntheses, Characterization, and Crystal Structures of Oxovanadium (V) Complexes with Similar Tridentate Hydrazones" Russian Journal of Coordination Chemistry, 2011, 37, p. 606-612) (Year: 2011).*
Gawande ("Synthesis and biological evaluation of azetidinone derivatives from 2-(phenylacetyl)benzohydrazide moiety by microwave method" Der Pharma Chemica, 2014, 6, p. 70-74) (Year: 2014).*
Amendment In Response To May 8, 2018 Communication Pursuant To Rules 70(2) And 70a (2) EPC filed Nov. 19, 2018 in connection with European Application No. EP 15867510.8.
Catalog #5271226, Cambridge Online Chemical Store, www.hit2lead.com/result.asp?search=24181768, retrieved Aug. 4, 2014.
Catalog #5285729, Cambridge Online Chemical Store, www.hit2lead.com/result.asp?search=60511156, retrieved Aug. 4, 2014.

(56) References Cited

OTHER PUBLICATIONS

Chun-Bao Tang, "N'-(4-Hydroxybenzylidine)-2-methylbenzohydrazide", Acta Crystallographica Section E, 2010, 66(10), p. o2482.
Communication Pursuant to Rules 70(2) and 70a (2) EPC dated May 8, 2018 in connection with European Patent Application No. 15867510.8.
D. Kumudha, et al., "Synthesis and evaluation of substituted aryl thazolidin-4-ones for analgesic and anti-inflammatory activities", Der Pharmacia Lettre, 2012, 4(4), pp. 1149-1154.
Davinder Kumar, et al., "Antimicrobial evaluation of 4-methylsulfanyl benzylidene/3-hydroxy benzylidene hydrazides and QSAR studies", Medical Chemistry Research, 2012, 21, pp. 382-394.
Extended European Search Report dated Apr. 20, 2018 in connection with European Patent Application No. 15867510.8.
Guo-Biao Cao, "(E)-3-Bromo-N'-(4-methoxybenzylidene)benzohydrazide methanol solvate", Acta Crystallographica Section E, 2009, 65(9), p. o2086.
International Search Report in connection with PCT International Application No. PCT/US2015/064278, dated Apr. 28, 2016.
J.-J. Ma, "Characterization and crystal structures of solvated N'-(4-hydroxy-3-nitrobenzylidene)-3-methylbenzohydrazide and N'-(4-dimethylaminobenzylidene)-3-methylbenzohydrazide", Journal of Structural Chemistry, 2013, vol. 54, No. 6, pp. 1145-1150.
K. Morimoto, et al., "Infrared absorption spectra of acyl hydrazine derivatives", Nippon Kagaku Zasshi, 1963, 84(8), pp. 613-617.
Maurizio Del Poeta et al. (2014) Synthesis and Biological Properties of Fungal Glucosylceramide. PLOS Pathogens, vol. 10, No. 1, p. e1003832.
Mor, V. et al. (2015) Identification of a New Class of Antifungals Targeting the Synthesis of Fungal Sphingolipids. mBio, 6, 3, e00647-15.
Mor, V. et al. Identification of new compounds targeting the fungal sphingolipid pathway. Abstract dated May 28, 2013.
Nolan Ung, et al., "An Approach to Quantify Endomembrane Dynamics in Pollen Utilizing Bioactive Chemicals", Molecular Plant, 2013, vol. 6, No. 4, pp. 1202-1213.
Pradeep Kumar, et al. "Substituted benzoic acid benzylidene/furan-2-yl-methylene hydrazides: synthesis, antimicrobial evaluation and QSAR analysis", ARKIVOC, 2008, pp. 159-178.
R.M. Desai, et al, "Synthesis and antimicrobial profile of 1,3,4-oxadiazoles, sulphonamides, 5-imidazolines, azomethines, 4-thiazolidinones, 2-azetidinones, formazans and tetrazolium chlorides", Indian Journal Heterocyclic Chemistry, 1999, vol. 8, pp. 329-334.
Rittershaus, P.C. et al. (2006) Glucosylceramide synthase is an essential regulator of pathogenicity of *Cryptococcus neoformans*. Journal of Clinical Investigation, 116, 6, 1651.
Tao Yang, et al. "3-Bromo-N'-[ (E)-4-hydroxybenzylidene]-benzohydrazide", Acta Crystallographica Section E, 2008, 64(7), p. o1186.
Written Opinion of the International Searching Authority in connection with PCT International Application No. PCT/US2015/064278, dated Apr. 28, 2016.
May 22, 2020 Second Preliminary Amendment in Response dated Mar. 23, 2020 Notification of Insufficiency Under 37 C.F.R. 1.492 and/or 1.495 (DO/EO/US) filed in connection with U.S. Appl. No. 16/495,605.
Mar. 4, 2020 Office Action issued in connection with U.S. Appl. No. 16/450,772.
Jun. 3, 2020 Communication in Response dated Mar. 4, 2020 Restriction Requirement and Petition for a One-Month Extension of Time filed in connection with U.S. Appl. No. 16/450,772.
Sep. 28, 2020 Office Action, issued in connection with U.S. Appl. No. 16/622,431.
Response to Communication pursuant to Rules 161(2) and 162 EPC, filed Aug. 4, 2020 in connection with European Patent Application No. EP18816480.0.
Communication pursuant to Article 94(3) EPC, dated Sep. 30, 2020 in connection with European Application No. EP15867510.8.
Chan et al., A Method for Identifying Small-Molecule Aggregators Using Photonic Crystal Biosensor Microplates JALA, 2009, p. 348-359.
Zhao et al., 1,8-Naphthalimide-based 'turn-on' fluorescent sensor for the detection of zinc ion in aqueous media and its applications for bioimaging Tet. Lett., 2013, 54, p. 3353-3358).
Gawande et al., Synthesis and biological evaluation of azetidinone derivatives from 2-a(phenylacetyl)benzohydrazide moiety by microwave method Der Pharma Chemica, 2014, 6, p. 70-74; 37, p. 606-612.
Yuan et al., Syntheses, Characterization, and Crystal Structures of Oxovanadium (V) Complexes with Similar Tridentate Hydrazones Russian Journal of Coordination Chemistry, 2011.
Bhat Ak et al: "Chemotherapy of fungus infections. III. Alkyl or aryl thiosemicarbazones, acid hydrazones, and styryl aryl ketones of 5-bromo-and 5-nitrosalicylaldehydes", Indian Journal of Chemistry, Council of Scientific and Industrial Research (C S I R), IN, vol. 10, No. 7, Jan. 1, 1972 (Jan. 1, 1972), pp. 694-698, XP009525187, ISSN: 0019-5103.
Xue L et al: "Dioxomolybdenum(VI) complexes derived from tridentate hydrazone ligands: Synthesis, characterization, crystal structures, and antibacterial activity", Russian Journal of Coordination Chemistry, Consultants Bureau, New York, NY, US, vol. 42, No. 2, Mar. 22, 2016 (Mar. 22, 2016), pp. 137-142, XP035650389, ISSN: 1070-3284, DOI: 10.1134/S1070328416020093.
S. Bala et al.: "Design, characterization, computational studies, and pharmacological evaluation of substituted-N'-[(1E)substituted-phenylmethylidene]benzohydrazide analogs", Med. Chem. Res., vol. 22, No. 6, Oct. 19, 2013 (Oct. 19, 2013), pp. 2755-2767, XP055557589.
N. P. Buu-Hoi et al.: "278. Tuberculostatic hydrazides and their derivatives", J. Che Soc., 1953, pp. 1358-1364, XP055557591.
Datta, K. et al., "Spread of *Cryptococcus gattii* into Pacific Northwest Region of the United States", Emerging Infectious Diseases, 2009,vol. 15, No. 8, pp. 1185-1191.
Dromer, F. et al., "Determinants of Disease Presentation and Outcome during Cryptococcosis: The CryptoA/D Study", PLoS ONE, 2007, vol. 4, No. 2, pp. 297-308.
Dromer, F. et al., "Major Role for Amphotericin B-Flucytosine Combination in Severe Cryptococcosis", PLoS ONE, 2008, vol. 3 No. 8, pp. 1-9.
Hajjeh, R.A. et al., "Cryptococcosis: Population-Based Multistate Active Surveillance and Risk Factors in Human Immunodeficiency Virus-Infected Persons", The Journal of Infectious Diseases, 1999, vol. 179, pp. 449-454.
Heung, L.J. et al., "Role of Sphingolipids in Microbial Pathogenesis", Infection and Immunity, 2006, vol. 74, No. 1, pp. 28-39.
Johnson, M.D and Perfect, J. R., "Caspofungin: first approved agent in a new class of antifungals" Expert Opinion on Pharmacotherapy, 2003, vol. 4, No. 5, pp. 807-823.
Lightowler, J.V.J., et al., "Treatment of Cryptococcal Meningitis in KwaZulu-Natal, South Africa", PLoS ONE, 2010, vol. 5, vol. 1, pp. 1-5.
Luberto, C. et al., "Roles for inositol-phosphoryl ceramide synthase 1 (IPC1) in pathogenesis of *C. neoformans*", Genes & Development, 2001, vol. 15, pp. 201-212.
McQuiston, T.J. et al., "Sphingolipids as Targets for Microbial Infections", Mini-Reviews in Medicinal Chemistry, 2006, vol. 6, pp. 671-680.
Mor V. et al., Erratum for Nor et al., "Identification of a New Class of Antifungals Targeting the Synthesis of Fungal Sphingolipids" MBio, 2018, vol. 9, No. 2, pp. 1-2.
Perfect, J.R. et al., "Voriconazole Treatment for Less-Common, Emerging, or Refractory Fungal Infections", Clinical Infectious Diseases, 2003, vol. 36, pp. 1122-1131.
Rhome, R. et al., "Biosynthesis and Immunogenicity of Glucosylceramide in *Cryptococcus neoformans* and Other Human Pathogens", Eukaryotic Cell, 2007, vol. 6, No. 10, pp. 1715-1726.
Rhome, R. and Poeta, M.D., "Sphingolipid Signaling in Fungal Pathogens", Adv Exp Med Biol, 2010, vol. 688, pp. 232-237.
Rhome, R. et al., "Surface Localization of Glucosylceramide during *Cryptococcus neoformans* Infection Allows Targeting as a Potential Antifungal", PLoS ONE, 2011, vol. 6, No. 1, pp. 1-13.

(56) References Cited

OTHER PUBLICATIONS

Shea, J.M. et al., "The Cryptococcal Enzyme Inositol Phosphosphingolipid-Phospholipase C Confers Resistance to the Antifungal Effects of Macrophages and Promotes Fungal Dissemination to the Central Nervous System", Infection and Immunity, 2006, vol. 74, No. 10, pp. 5977-5988.

Singh, A. et al., "Methylation of glycosylated sphingolipid modulates membrane lipid topography and pathogenicity of *Cryptococcus neoformans*", Cell Microbiol, 2012, vol. 14, No. 4, pp. 500-516.

Lazzarini, Cristina & Haranahalli, Krupanandan & McCarthy, J. & Mallamo, John & Ojima, Iwao & Poeta, Maurizio. (2020). Preclinical Evaluation of Acylhydrazone SB-AF-1002 as a Novel Broad-Spectrum Antifungal Agent. Antimicrobial Agents and Chemotherapy. 64. 10.1128/AAC. 00946-20.

Haranahalli K, Lazzarini C, Sun Y, et al. SAR Studies on Aromatic Acylhydrazone-Based Inhibitors of Fungal Sphingolipid Synthesis as Next-Generation Antifungal Agents. J Med Chem. 2019;62 (17) : 8249-8273. doi: 10. 1021/acs. jmedchem. 9b01004.

G. L. Backes et al., "Synthesis and antifungal activity of substituted salicylaldehyde hydrazones, hydrazides and sulfohydrazides", Bioorganic & Medicinal Chemistry, 2014, 22(17), pp. 4629-4636.

Y.-X. Feng et al., "Synthesis, molecular structures, and antimicrobial activities of N'-(3, 5-dibromo-2-hydroxybenzylidene)-2-fluorobenzohydrazide and N'-(4-diethylamino-2-hydroxybenzylidene)-2-fluorobenzohydrazide", J. Chil. Chem. Soc., 2014, 59(3), pp. 2555-2558.

International Search Report dated Sep. 27, 2018 in connection with PCT International Application No. PCT/US2018/037846.

Written Opinion (form PCT/ISA/237) dated Sep. 27, 2018 in connection with PCT International Application No. PCT/US2018/037846.

* cited by examiner

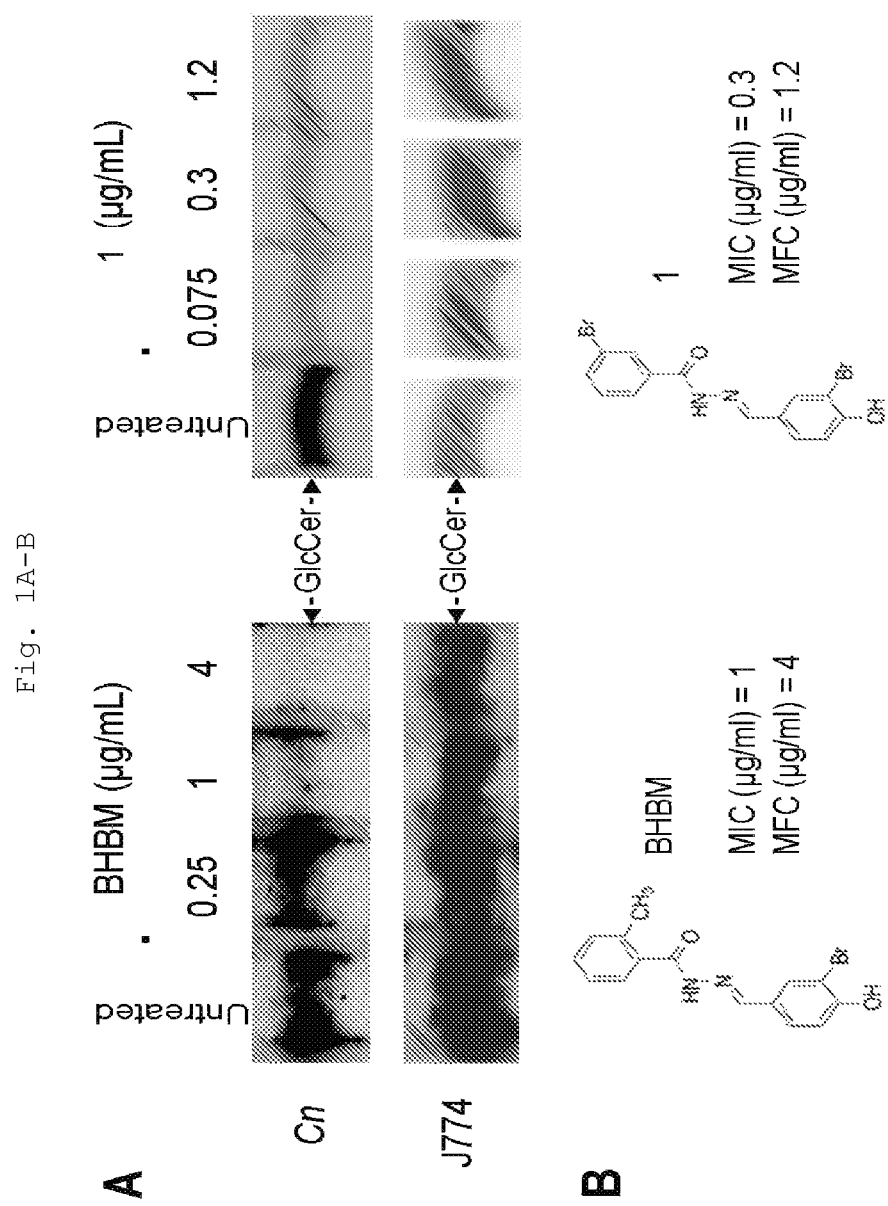
Fig. 1A-B

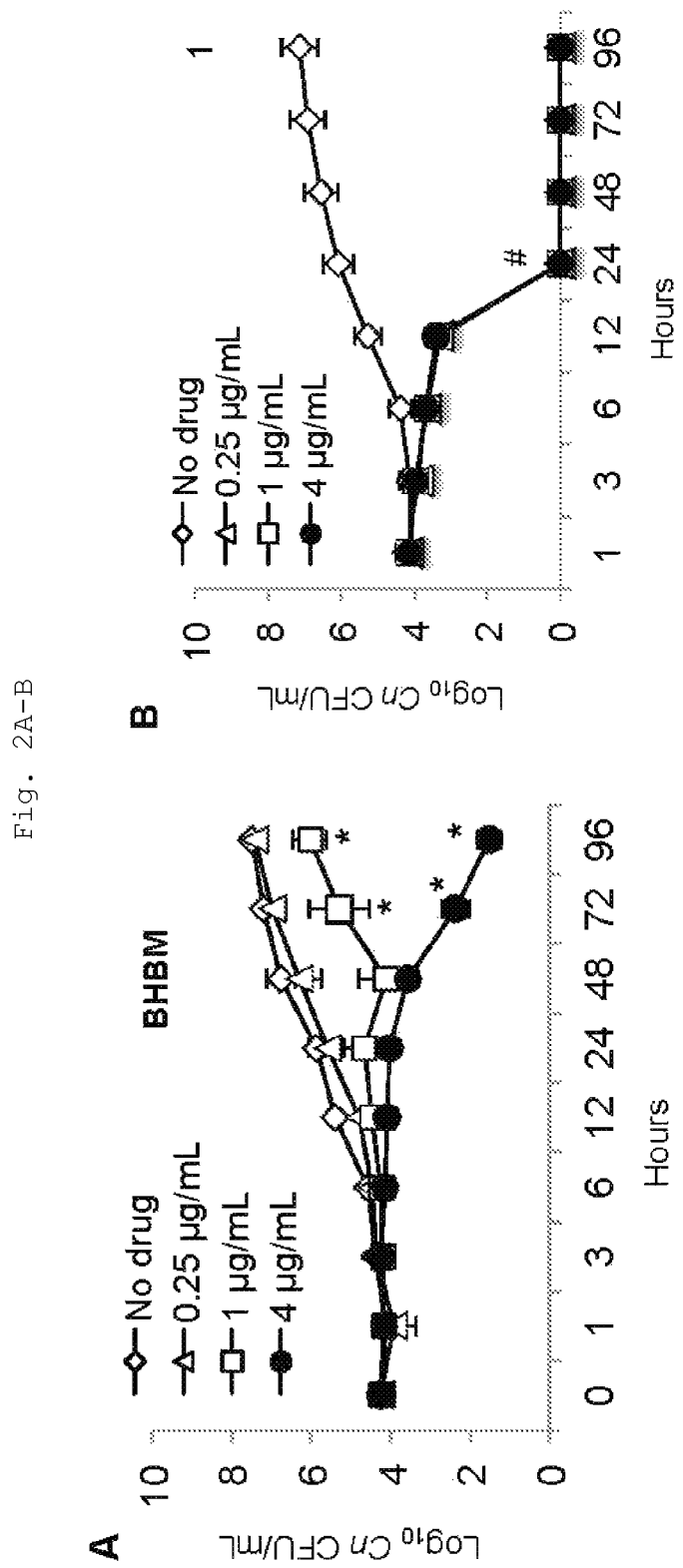
Fig. 2A-B

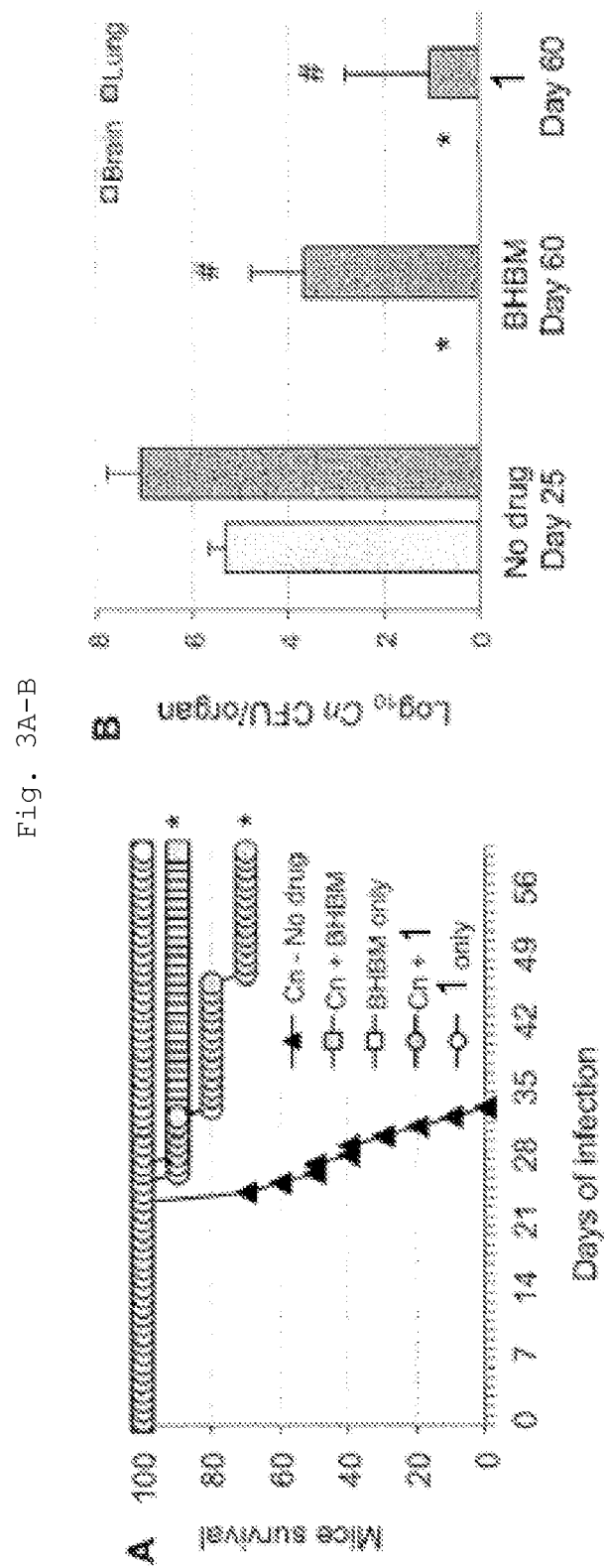
Fig. 3A-B

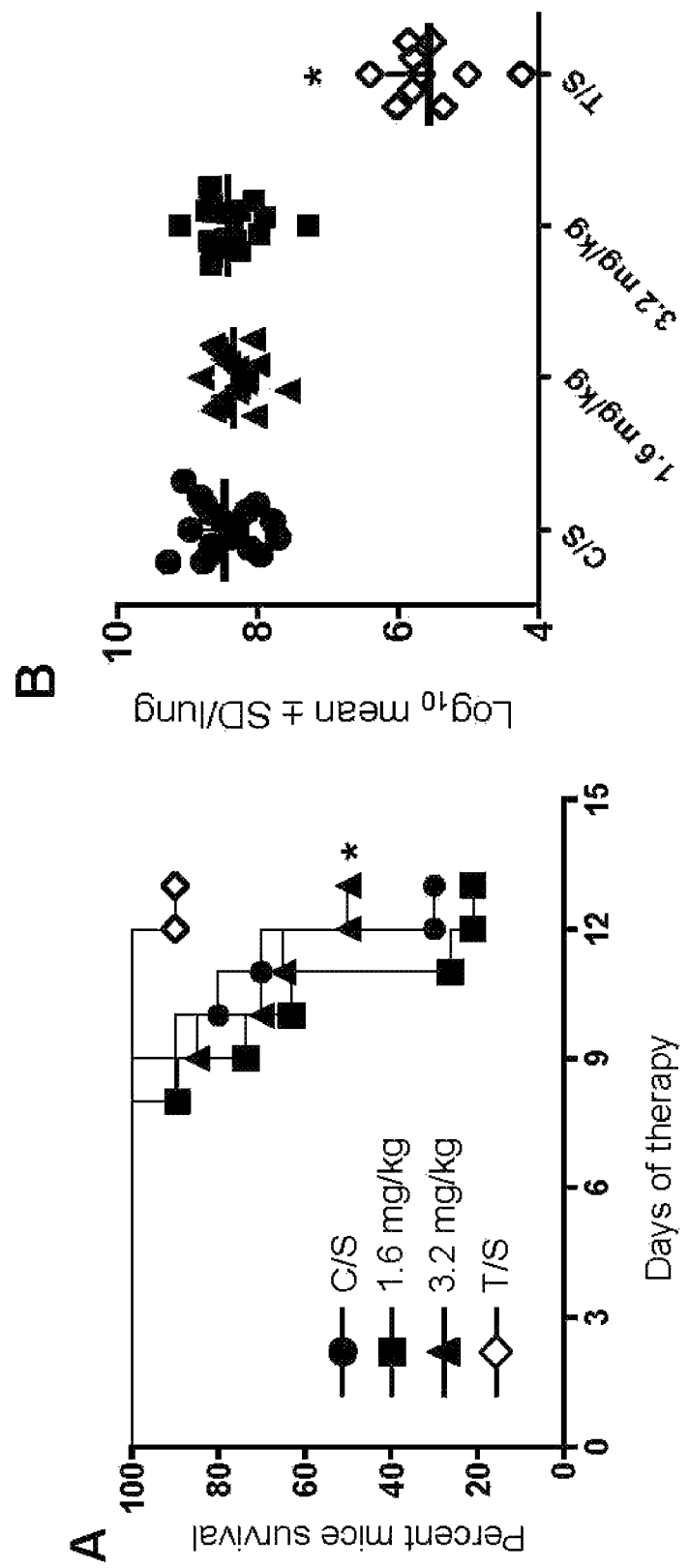
Fig. 4A-B

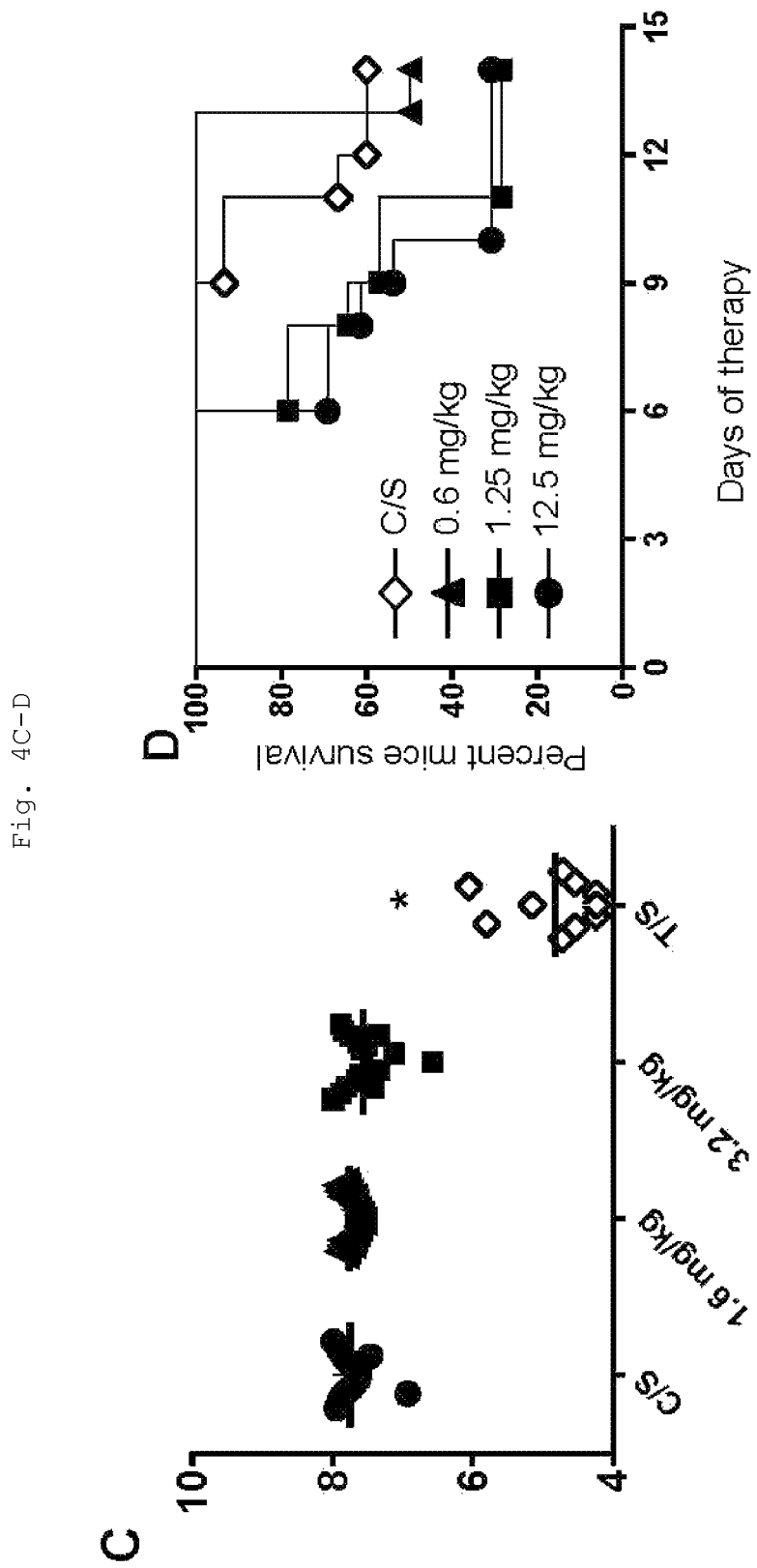
Fig. 4C-D

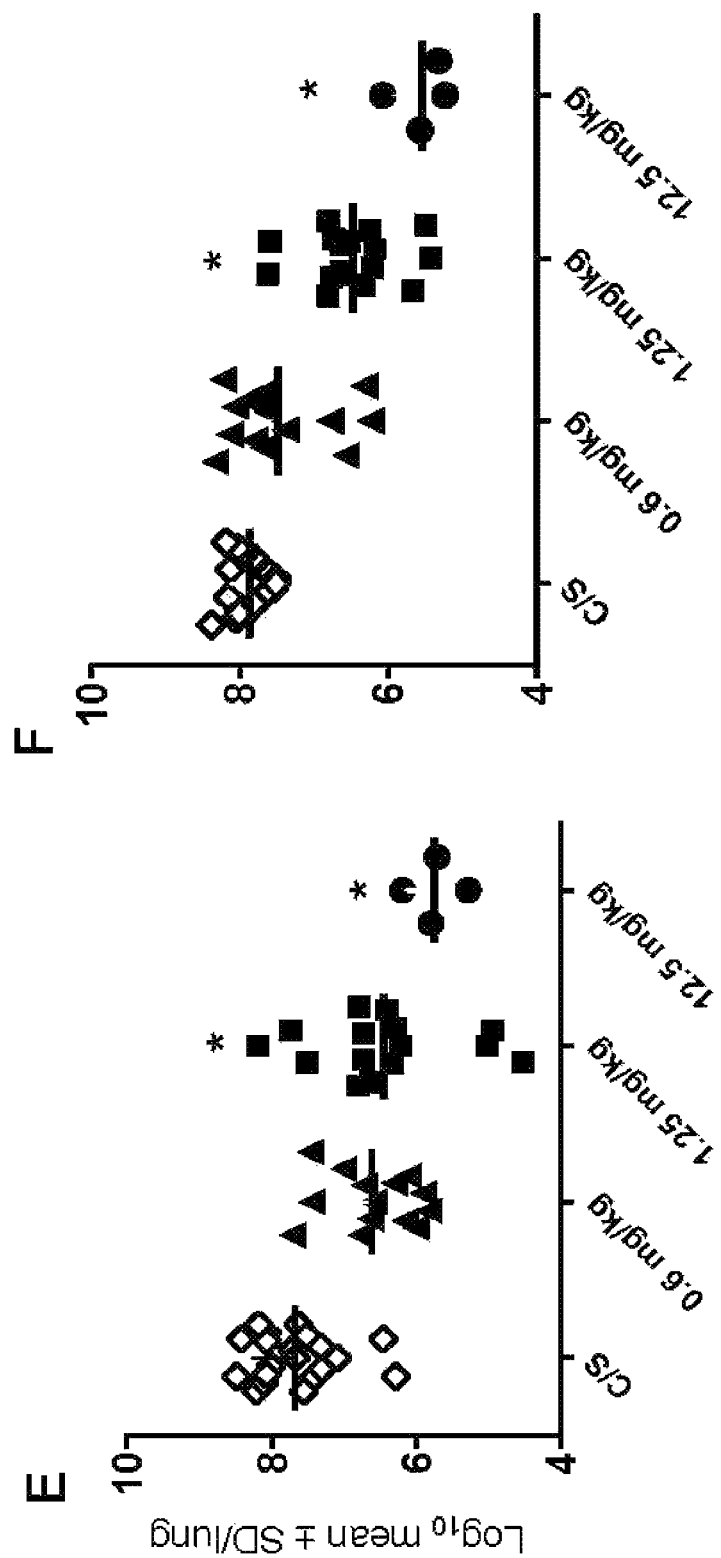
Fig. 4E-F

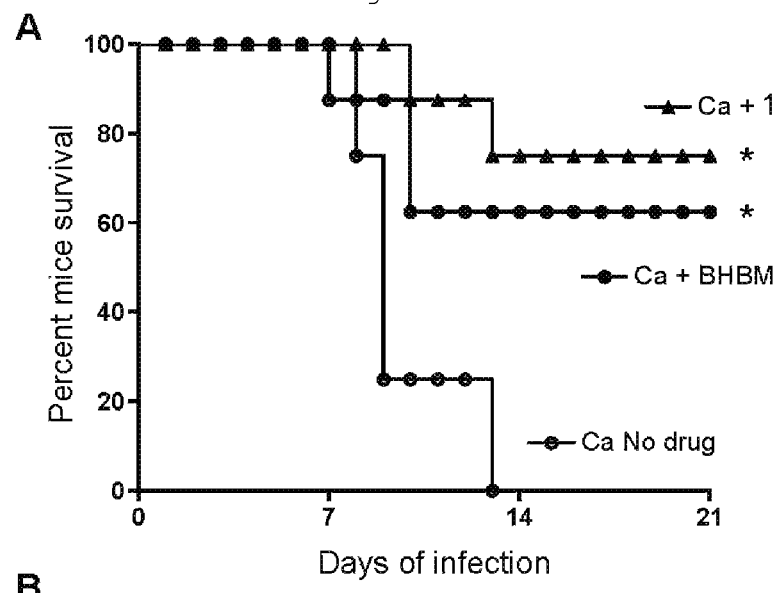
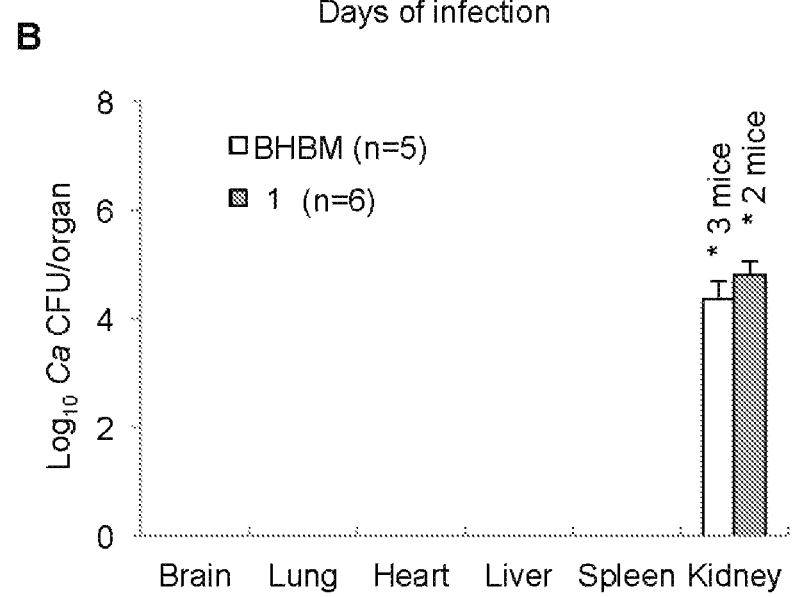
Fig. 5A-B

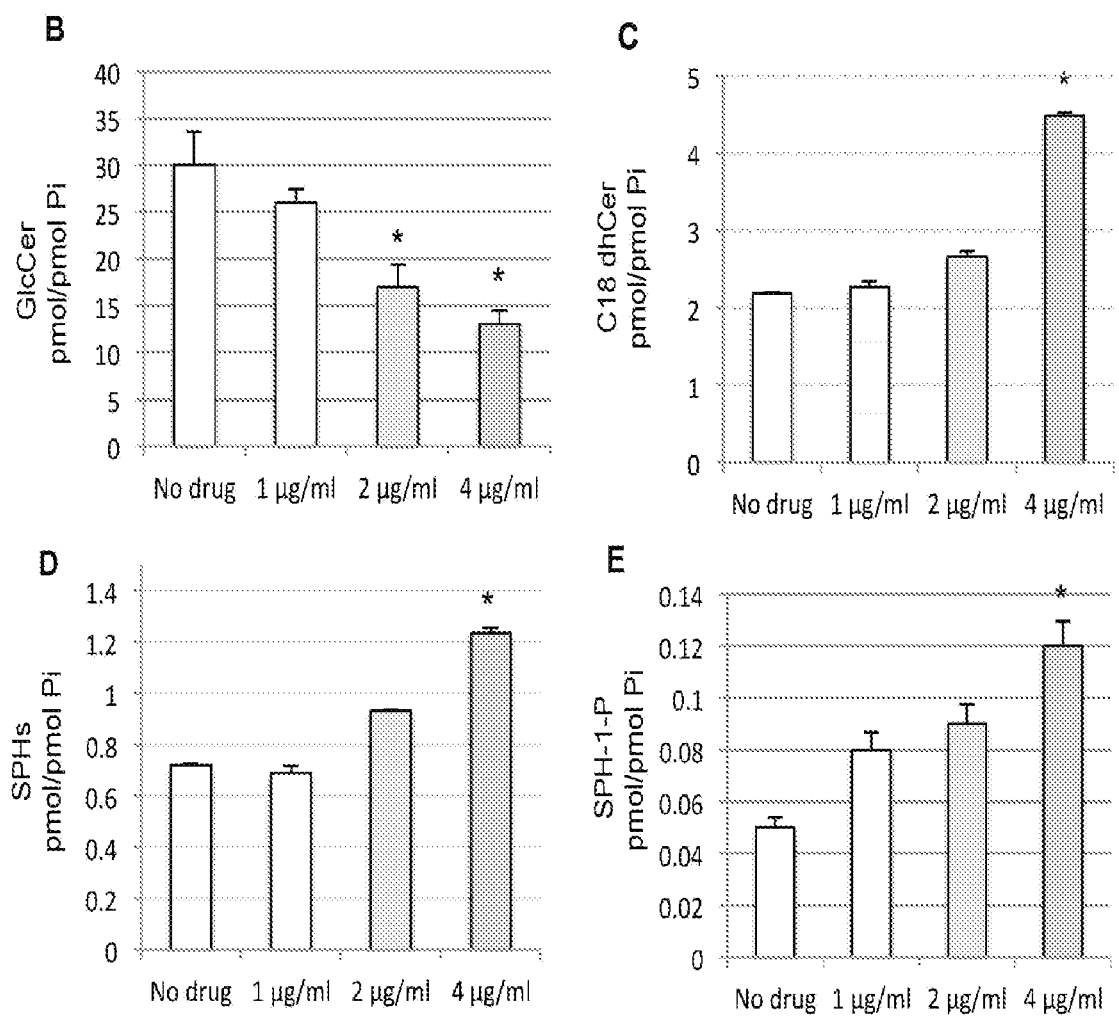
Fig. 6B-E

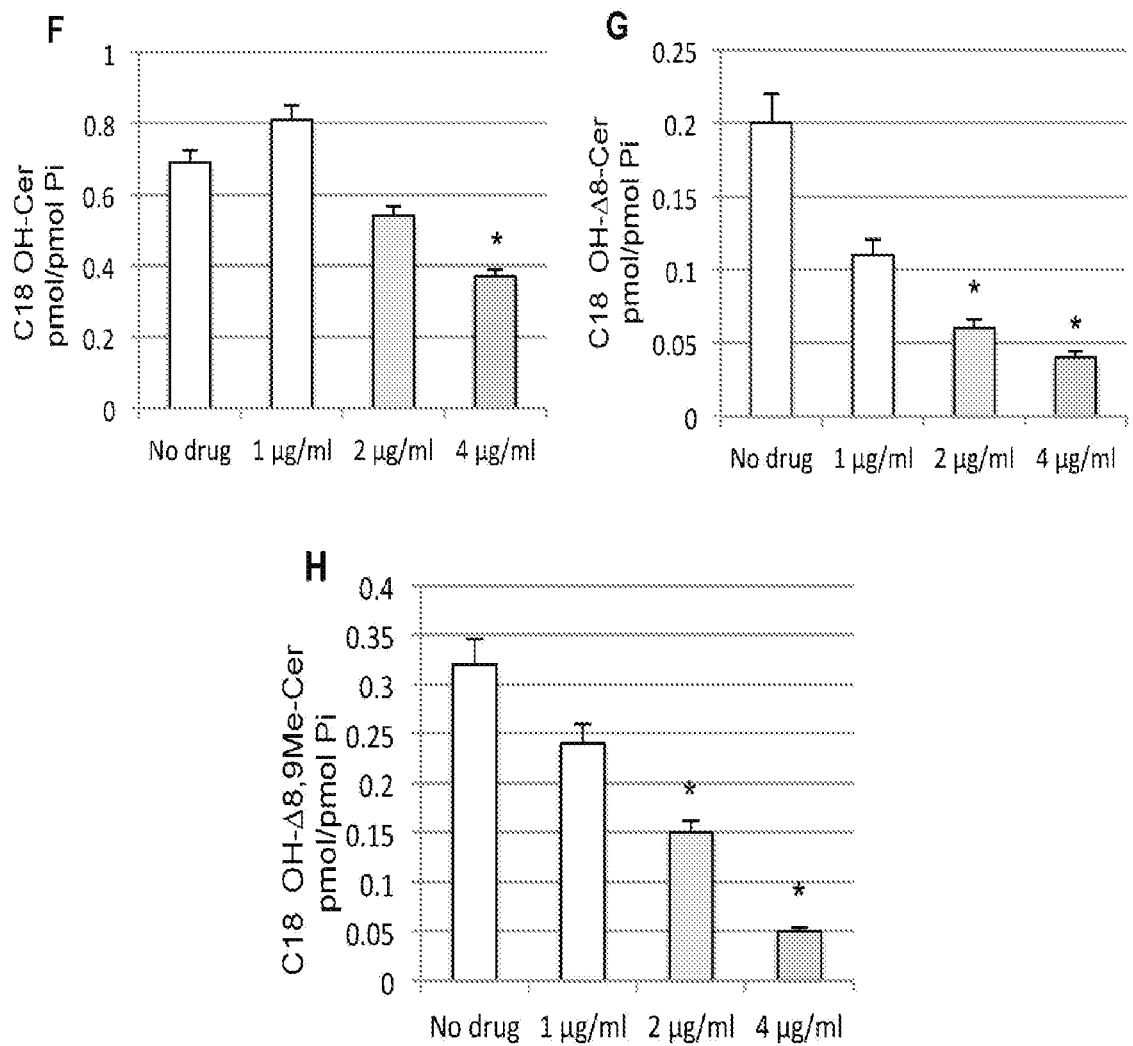
Fig. 6F-H

Fig. 7A-C
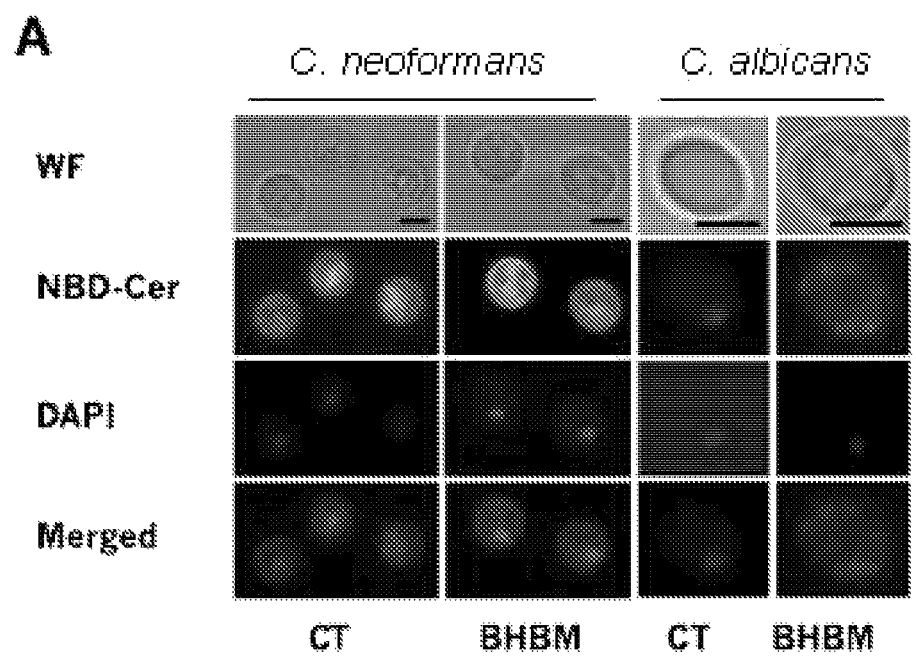
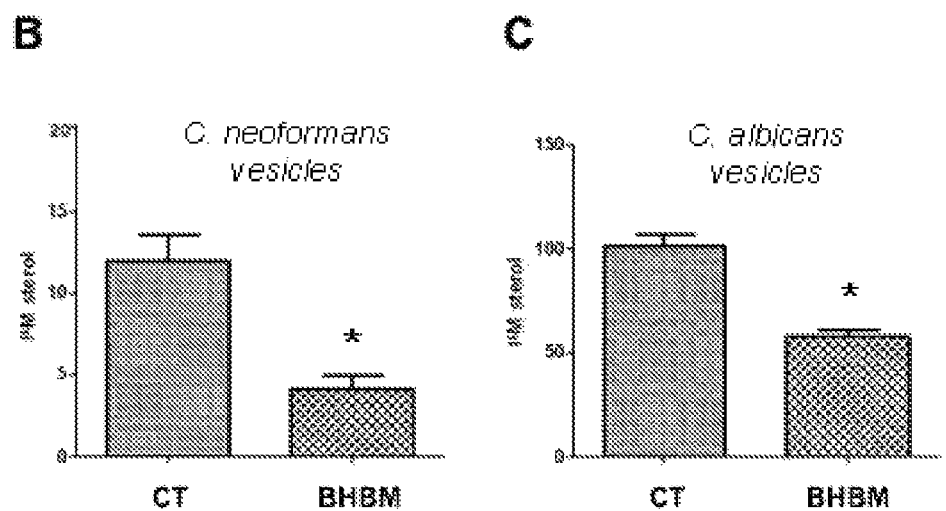

Schematic of the compound library screening

N'-(3-bromo-4-hydroxybenzylidene)-2-methylbenzohydrazide

BHBM

Formula : $C_{15}H_{13}BrN_2O_2$
Molecular Weight : 333

Solubility : Up to 50 mg/mL in 100% DMSO
: 1 mg/mL in PBS containing 30% DMSO
Stability : Stock of 50 mg/mL in -20°C for at least 1 year 3-bromo-N'-(3-bromo-4-hydroxybenzylidene) benzohydrazide

| Formula | : $C_{14}H_{10}Br_2N_2O_2$ |
| --- | --- |
| Molecular Weight | : 398 |
| Solubility | : 50 mg/mL in 100% DMSO |
| | : 1 mg/mL in in PBS containing 50% DMSO |
| Stability | : Stock of 50 mg/mL in -20°C for at least 1 year |

Fig. 11

| | Drug A | | | Drug B | | FIC* |
|---|---|---|---|---|---|---|
| | MIC alone | MIC combined (μg/mL) | | MIC alone | MIC combined (μg/mL) | |
| BHBM | 1 | 0.125 | Fluconazole | 3.12 | 0.8 | 0.38 |
| BHBM | 1 | 0.25 | Amphotericin B | 0.6 | 0.3 | 0.75 |
| BHBM | 1 | 0.5 | Caspofungin | 17.5 | 8.75 | 1 |
| BHBM | 1 | 0.25 | Tunicamycin | 0.4 | 0.2 | 0.5 |
| 1 | 0.3 | 0.063 | Fluconazole | 3.12 | 0.8 | 0.47 |
| 1 | 0.3 | 0.15 | Amphotericin B | 0.6 | 0.16 | 0.77 |
| 1 | 0.3 | 0.15 | Caspofungin | 8.75 | 4.3 | 1 |
| 1 | 0.3 | 0.15 | Tunicamycin | 0.4 | 0.2 | 1 |

*Strongly synergistic: FIC< 0.5; Synergistic: FIC< 1; Additive: FIC= 1; No effect: 1< FIC <2; Antagonistic: FIC > 2

Fig. 14

| Test (Units) | Normal range | Control (n=3) | BHBM (n=5) |
|---|---|---|---|
| ALP (U/L) | 35.00-101.00 | 114.33 ± 13.27 | 94.00 ± 6.51 |
| ALT (U/L) | 17.00-32.00 | 28.00 ± 1.73 | 28.00 ± 5.88 |
| AST (U/L) | 54.00-120.00 | 48.00 ± 5.56 | 100.00 ± 59.12 |
| TBILI (mg/dL) | 2.00-2.40 | 0.23 ± 0.05 | 0.28 ± 0.05 |
| CREAT (mg/dL) | 0.20-0.90 | 0.24 ± 0.02 | 0.18 ± 0.01 |

ALP, Alkaline Phosphatase; ALT, Alanine Aminotransferase; AST, Aspartate Aminotransferase; TBILI, Total bilirubin; CREAT, Creatinine

Fig. 15

| Leukocytes (Units) | Normal range | Control (n=3) | BHBM (n=5) |
|---|---|---|---|
| WBC (K/uL) | 1.80-10.70 | 4.11 ± 0.56 | 5.11 ± 1.00 |
| NE (K/uL) | 0.10-2.40 | 0.40 ± 0.03 | 0.91 ± 0.15 |
| LY (K/uL) | 0.90-9.30 | 3.34 ± 0.52 | 3.72 ± 0.87 |
| MO (K/uL) | 0.00-0.40 | 0.32 ± 0.05 | 0.35 ± 0.07 |
| EO (K/uL) | 0.00-0.20 | 0.03 ± 0.03 | 0.06 ± 0.02 |
| BA (K/uL) | 0.00-0.20 | 0.02 ± 0.01 | 0.02 ± 0.01 |

WBC, White blood cell; NE, Neutrophils; LY, lymphocytes; MO, Monocytes; EO, Eosinophils; BA, Basophils. K/µl

Fig. 16

| | Normal range | Control (n=3) | BHBM (n=5) |
|---|---|---|---|
| Erythrocytes (Units) | | | |
| RBC (M/uL) | 6.36-9.42 | 7.33 ± 0.24 | 8.36 ± 0.18 |
| Hb (g/dL) | 11.00-15.10 | 11.15 ± 0.07 | 12.06 ± 0.40 |
| HCT (%) | 35.10-45.40 | 39.33 ± 1.36 | 44.02 ± 1.03 |
| MCV (fL) | 45.40-60.30 | 53.87 ± 0.25 | 52.66 ± 0.51 |
| MCH (pg) | 14.10-19.30 | 15.00 ± 0.30 | 14.44 ± 0.16 |
| MCHC (g/dL) | 30.20-34.20 | 28.05 ± 0.45 | 27.40 ± 0.45 |
| RWD (fL) | 12.40-27.00 | 16.27 ± 0.51 | 16.26 ± 0.35 |
| Thrombocytes (Units) | | | |
| PLT (K/uL) | 592.00-2972.00 | 372.33 ± 221.34 | 502.20 ± 125.59 |
| MPV (fL) | 5.00-20.00 | 4.17 ± 0.05 | 4.25 ± 0.12 |

RBC, Red blood cell; Hb, Haemoglobin; HCT, Haematocrit; MCV, Mean Corpuscular Volume; MCH, Mean Corpuscular Haemoglobin; MCHC, Mean Corpuscular Haemoglobin Concentration; RWD, Red blood cell Distribution Width; PLT, platelets; MPV, Mean Platelets Volume.

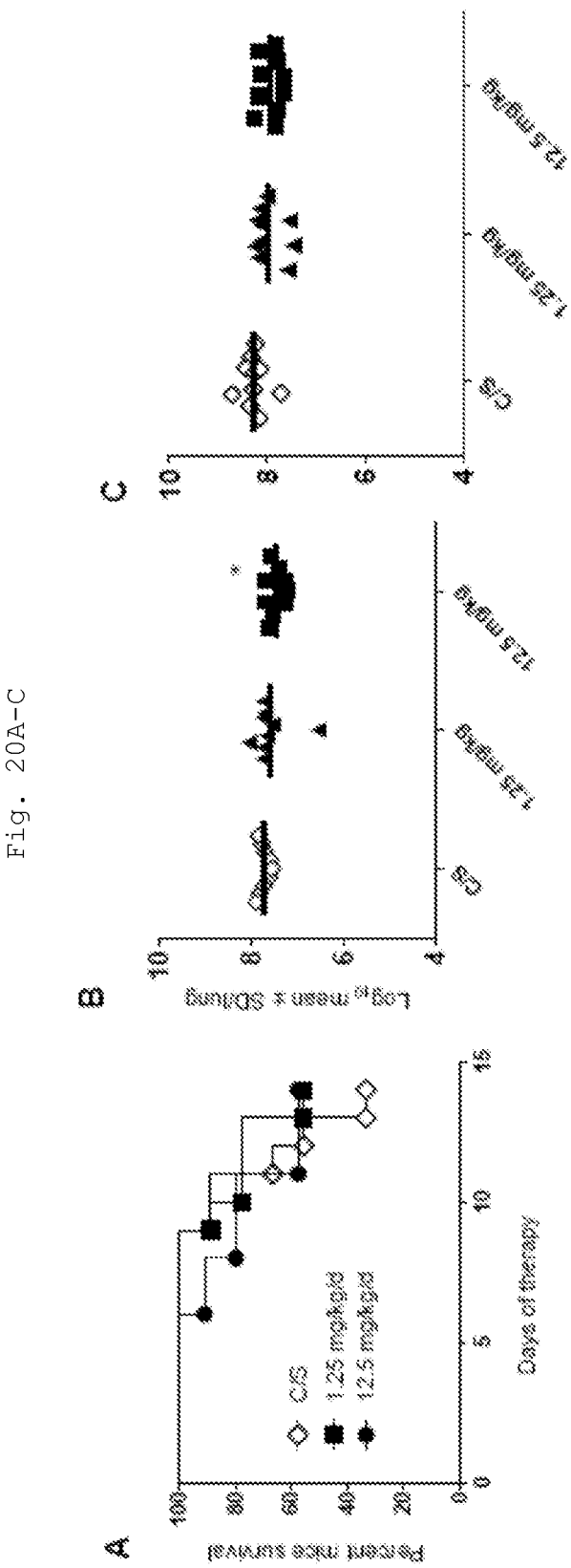
Fig. 20A-C

Fig. 21

Pharmacokinetic parameters upon BHBM IV dosing

| Parameter | Unit | Normal mice High IV dose | IS/IN mice High IV dose | Normal mice Low IV dose | IS/IN mice Low IV dose |
|---|---|---|---|---|---|
| $T_{1/2}$ | h | 1.03 | 1.243 | 0.983 | 1.295 |
| $C_{5\,min}$ | ng/ml | 105.80 | 171.612 | 72.52 | 59.45 |
| $C_0$ | ng/ml | 125.44 | 609.56 | 150.04 | 144.60 |
| $AUC_{0-t}$ | ng/ml*h | 192.62 | 224.98 | 121.42 | 126.57 |

Pharmacokinetic parameters upon BHBM IP dosing

| Parameter | Unit | Normal mice High IP dose | IS/IN mice High IP dose | Normal mice Low IP dose | IS/IN mice Low IP dose |
|---|---|---|---|---|---|
| $T_{1/2}$ | h | 1.43 | 0.84 | 1.70 | 0.79 |
| $T_{max}$ | h | 0.50 | 0.50 | 0.50 | 0.50 |
| $C_{max}$ | ng/ml | 112.39 | 374.60 | 82.73 | 213.42 |
| $AUC_{0-t}$ | ng/ml*h | 174.51 | 326.06 | 88.79 | 173.57 |
| BA | % | 90.59 | 100.33 | 92.18 | 106.82 |

Fig. 23

|  | BHBM | 2 | 3 | 4 | 5 |
|---|---|---|---|---|---|
| MIC (μg/mL) on H99 | 1 | >100 | >100 | >100 | 3.13 |
| Solubility (100 mg/mL) | 100% DMSO | 100% DMSO | 100% DMSO | 100% DMSO | 100% DMSO |
| Solubility (1 mg/mL) | 30% DMSO | 50% DMSO | 20% DMSO | 30% DMSO | 1% DMSO |
| Stability (Stock of 100 mg/mL) | At least 1 year at -20C | At least 1 year at -20C | At least 1 year at -20C | At least 1 year at -20C | At least 1 year at -20C |
| Toxicity on J774.16 (IC$_{50}$) | 50 μg/mL | ND | ND | ND | 50 μg/mL |

|  | 6 | 1 | 7 | 8 | 9 | 10 |
|---|---|---|---|---|---|---|
| MIC (μg/mL) on H99 | 5 | 0.3 | >100 | >100 | 3.13 | 1.6 |
| Solubility (100 mg/mL) | 100% DMSO | 100% DMSO | 100% DMSO | 100% DMSO | 100% DMSO | 100% DMSO |
| Solubility (1 mg/mL) | >50% DMSO | 50% DMSO | 30% DMSO | 50% DMSO | 40% DMSO | 50% DMSO |
| Stability (Stock of 100 mg/mL) | At least 1 year at -20C | At least 1 year at -20C | At least 1 year at -20C | At least 1 year at -20C | At least 1 year at -20C | At least 1 year at -20C |
| Toxicity on J774.16 (IC$_{50}$) | ND | 50 μg/mL | ND | ND | 50 μg/mL | 25 μg/mL |

Fig. 28A-B
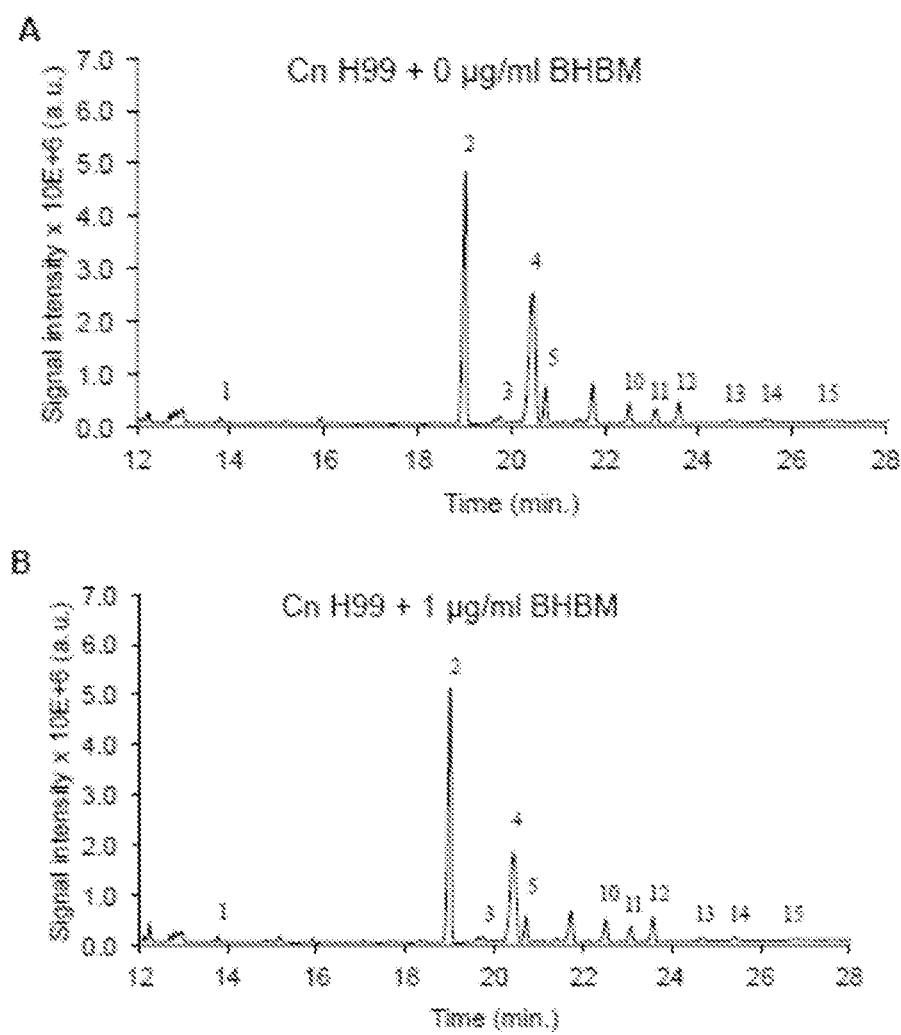

Fig. 28C-D
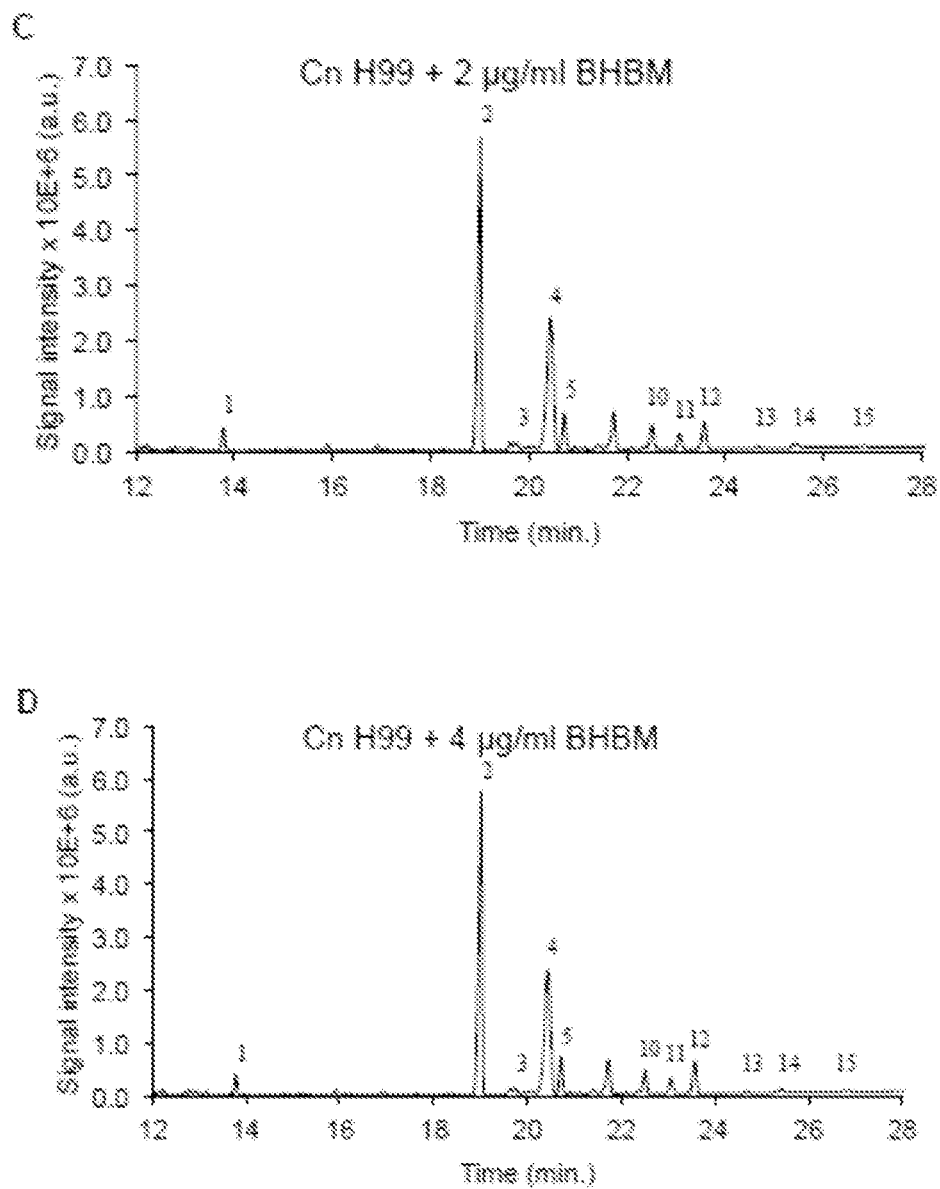

Fig. 30A-C
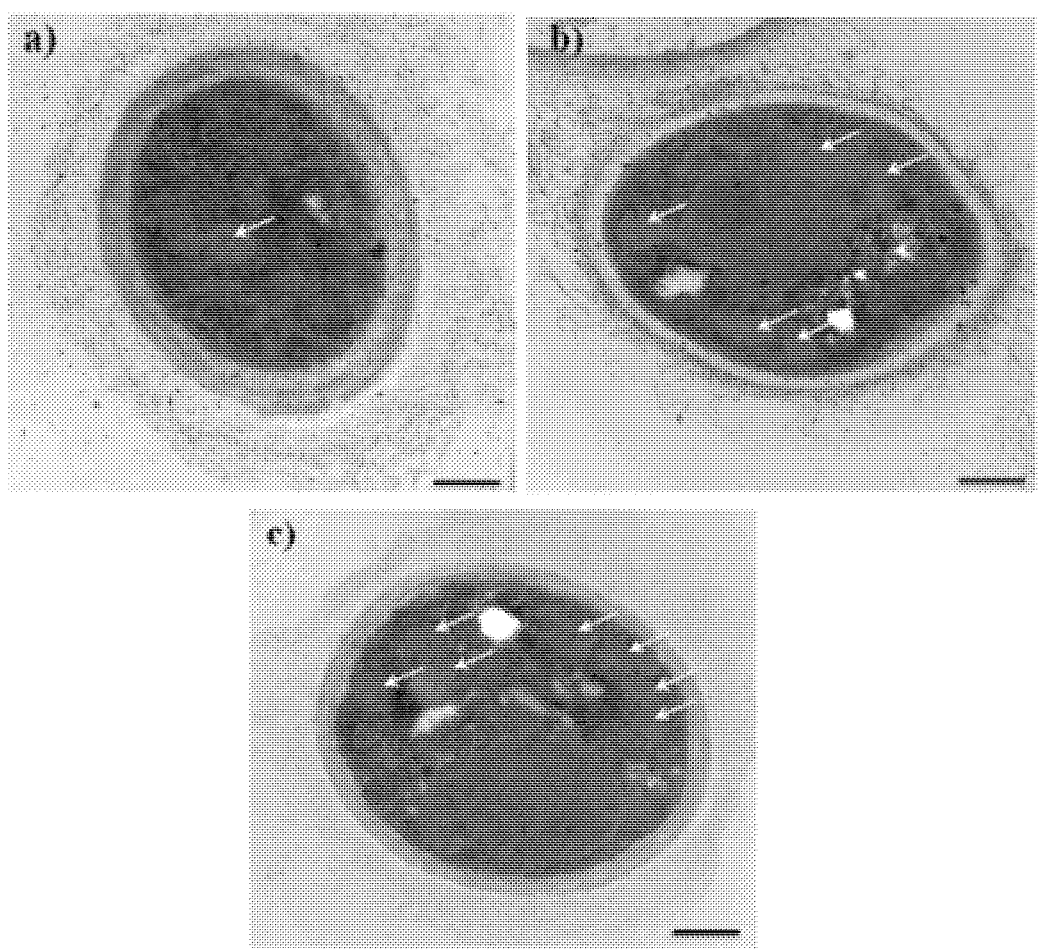

ANTI-FUNGALS TARGETING THE SYNTHESIS OF FUNGAL SHINGOLIPIDS

CROSS-REFERENCE TO RELATED APPLICATIONS

This application is a continuation of U.S. Ser. No. 15/534,353, which is a § 371 national stage of PCT International Application No. PCT/US2015/064278, filed Dec. 7, 2015, claiming the benefit of U.S. Provisional Applications Nos. 62/192,459, filed Jul. 14, 2015 and 62/088,914, filed Dec. 8, 2014, the content of each of which is hereby incorporated by reference into the application.

This invention was made with government support under grant numbers AI100631, AI056168, AI071142, and AI087541 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Globally, over 300 million people are afflicted by a serious fungal infection and 25 million are at risk of dying or losing their sight (Fungal Infection Trust 2011). Among fungal infections, invasive fungal infections such as cryptococcosis, candidiasis, aspergillosis and pneumocystosis are the most common and the most life-threatening (Brown, G. D. et al. 2012; Gullo, A. 2009; Tuite, N. L. & Lacey. K. 2013). These infections have risen dramatically over the last 20 years, some over 14-fold. The CDC estimates that more than 1 million new cases per year of cryptococcosis will occur worldwide in patients with AIDS, and 600,000 will die from the infection. This is a drastic increase considering that prior to the mid-1950s, fewer than 300 cases had been reported in the medical literature (reviewed in Sorrell, T. C. et al. 2011). Certain medical devices, such as catheters, provide the port of entry to fungi that colonize the skin and mucosa. As a result, disseminated candidiasis is the 4th most common hospital-acquired sepsis with >120,000 deaths/year (Perlroth, J. et al. 2007; Rueping, M. J. et al. 2009; Guery B. P. et al. 2009). Disseminated aspergillosis represents another invasive fungal infection that is steadily increasing in immunocompromised patients with a mortality rate of 450,000/year (Mayr, A. & Lass-Florl, C. 2011; Maschmeyer, G. et al. 2007; Munoz, P. et al. 2008; Ruping, M. J. et al. 2008). *Aspergillus* spp. is also responsible for severe asthma by fungal sensitization (SAFS) accounting for 100,000 additional deaths annually.

*Pneumocystis* spp. are a group of host-specific opportunistic fungi that reside in the lungs of humans and animals in nature. The organism is named *P. jirovecii* in humans, *P. carinii* in rats, and *P. murina* in mice. *Pneumocystis* pneumonia (PCP) remains the most prevalent opportunistic infection in patients infected with the human immunodeficiency virus (HIV). An estimated 539 million patients were discharged from hospitals between 1986 and 2005, of whom an estimated 312,411 had AIDS-associated PCP. Although numbers of cases of PCP has decreased in economically developed countries, the worldwide incidence is estimated to exceed 400,000 (Kelley, C. F. et al. 2009). Reports on mortality rates for PCP are variable, ranging from 13% to as high as 80%, which even at the lowest rate results in more than 52,000 deaths per year (Kelley, C. F. et al. 2009). PCP is also prevalent in other patient groups, notably patients that are chronically immune suppressed due to solid organ transplantation or due to chemotherapy for cancer or autoimmune disease. *P. jirovecii* (Pj) is also a frequent colonizer of the respiratory tract in immunocompetent individuals with other underlying pulmonary diseases, such as Chronic Obstructive Pulmonary Disease (COPD), in which it initiates a deleterious inflammatory reaction (Huang, L. et al. 2006). Based on these reports, over 1,300,000 people are estimated to die every year because of invasive fungal infections and, most likely, this is an underestimated figure (1, 2). This mortality rate is similar to the one from malaria (1,240,000/year) (WHO World Malaria Report 2013) and tuberculosis (1,400,000/year) (WHO World Global Tuberculosis 2013).

While there are about 30 branded prescription antifungal drugs on the market, three classes of antifungals are mainly used to manage invasive fungal infections; 1) Azoles, such as fluconazole launched in the mid-1980s, 2) polyenes, such as amphotericin B launched in the mid-1950s and 3) echinocandins, such as caspofungin launched in early 2000. However, the increased use of current azoles has led to an increase in drug resistance, limiting their effectiveness. In addition, drug-drug interaction issues can be a major impediment to the use of voriconazole, itraconazole and posaconazole. The interactions with cancer chemotherapy agents and immunosuppressants can be particularly difficult to handle clinically. Systemic antifungals, such as amphotericin B, tend to have relatively high toxicity and side effects. The echinocandins have a lower incidence of adverse events compared to older antifungals but they bind highly to serum proteins, there are no oral formulations, and their antifungal spectrum of activity is very narrow (Farowski, F. et al. 2012; Farowski, F. et al. 2013; Odabasi, Z. et al. 2007; Saribas, Z. et al. 2012; Yanni, S. B. et al. 2011). In the case of *Pneumocystis*, the situation is direr. *Pneumocystis* pneumonia does not respond to any of the standard antifungals described above (Carmona, E. M. & Limper, A. H. 2011). The drug of choice for the treatment and chemoprophylaxis of PCP is trimethoprim-sulfamethoxazoe (TMP-SMX). Analysis of *P. jirovecii* isolates demonstrates that the pathogen is evolving mutations in the target genes of TMP-SMX, suggesting *P. jirovecii* could soon become resistant to SMX in the combination, considered the more potent of the two drugs that makeup the combination therapy (Ma, L. et al. 1999). Atovaquone and pentamidine, both second line treatments, suffer from low efficacy and severe adverse events (SAEs) that include nephrotoxicity, neutropenia, hypotension and hypoglycemia (Benfield, T. et al. 2008). Atovaquone inhibits the mitochondrial cytochrome Bc1 complex in parasites at much lower concentrations than the respective mammalian complex. However, evolving resistance to atovaquone, corresponding to mutations in the *Pneumocystis* cytochrome b gene, has been observed (Kazanjian, P. et al. 2001). Pentamidine has a broad antimicrobial action with no specific target known and is highly toxic and often considered to be a drug of last resort. We are faced, then, with a growing patient population, a microorganism that cannot be easily subjected to detailed biochemical analysis in the laboratory, a developing resistance to standard of care medications and a limited industrial effort to advance new therapies into the clinic. Thus, there is a need for new, safer and more effective compounds.

Studies in our and other laboratories identified sphingolipids as key regulators of fungal pathogenesis (reviewed in Heung, L. J. et al. 2006 and Singh, A. 2011). Particularly, a fungal sphingolipid named glucosylceramide (GlcCer) is required for the pathogenic fungus *Cryptococcus neoformans* to cause a lethal meningo-encephalitis (Kechichian, T. B. et al. 2007; Rittershaus, P. C. et al. 2006). In fact, mice survived the infection by a *C. neoformans* mutant strain lacking the final enzyme for the synthesis of GlcCer (GlcCer synthase 1 or Gcs1). The Δgcs1 mutant was confined in the lung granuloma and it did not reach the bloodstream and, thus, it did not disseminate to the brain. Later, other investigators corroborated and extended our findings that mutation of genes involved in the last steps of the GlcCer pathway affect fungal virulence not only of fungi infecting humans, such as *C. neoformans* (Liu, O. W. et al. 2008; Singh, A. et al. 2012), *Candida albicans* (Oura, T. & Kajiwara, S. 2010; Noble, S. M. et al. 2010; Oura, T. & Kajiwara, S. 2008), and *Aspergillus fumigatus* (Levery, S. B. et al. 2002), but also of fungi infecting plants (da Silva, A. F. et al. 2004; Ramaoorthy, V. et al. 2009). That GlcCer is required for fungal virulence in plants is also suggested by studies showing that plants defend themselves against fungi by producing specific defensins (e.g. RsAFP2 and others) that bind to fungal and not mammalian GlcCer (Thevissen, K. et al. 2004). Interestingly, these plant defensins are able to bind GlcCer of human pathogenic fungi and able to kill them in vitro and, in some cases, during in vivo infection in animal models (Thevissen, K. 2004; Tavares, P M. 2008; Aerts, A M. 2007; Lobo, D S. 2007; Thevissen, K. 2012; Mello Ede, O. et al. 2014; Oguro, Y. et al. 2014; Goncalves, S. et al. 2012; de Medeiros, L. N. et al. 2010).

Mechanistic studies revealed that GlcCer is involved in the regulation of fungal cell replication in environments characterized by neutral/alkaline pH (Kechichian, T. B. et al. 2007; Levery, S. B. et al. 2002; Rhome, R. et al. 2011). Particularly, when fungal cells lacking GlcCer are exposed to neutral/alkaline pH, they cannot progress through the cell cycle and, thus, cytokinesis does not occur (Rittershaus, P. C. et al. 2006; Levery, S. B. et al. 2002; Saito, K. et al. 2006). Later, we linked this phenomenon to the regulation by GlcCer of physical properties of fungal plasma membranes of *C. neoformans* (Singh, A. et al. 2012). The synthesis of GlcCer seems to be important also during *Pneumocystis* pneumonia (PCP) as GlcCer synthase transcripts have been found to be elevated at the time of isolation of the fungus from a fulminate lung infection (Cushion, M. T. et al. 2007). Interestingly, in most dimorphic fungi, production of GlcCer is detected only in the host infective form (yeast) and not in the environmental form (mold) (Warnecke, D. et al. 2003; Rhome, R. et al. 2007; Toledo, M. S. et al. 2001). Taken together, these studies suggest that GlcCer is most likely a pan-fungal virulence factor required during infection to promote fungal growth at neutral/alkaline environments in the host (e.g. alveolar spaces, cerebrospinal fluid and bloodstream), and as such, it is a promising novel drug target. Currently, inhibitors that block the fungal but not the mammalian GlcCer synthesis are not available.

SUMMARY OF THE INVENTION

The present invention provides a compound having the structure:

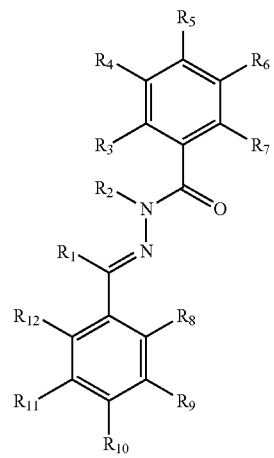

wherein
$R_1$ is —H, alkyl, alkenyl, or alkynyl;
$R_2$ is —H, alkyl, alkenyl, or alkynyl;
$R_3$, $R_4$, $R_5$, and $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_3$, —$NH_2$, —$NHR_{13}$, —$NR_{14}R_{15}$, —$NHCOR_{12}$, or —$CONR_{14}R_{15}$;
$R_9$, $R_{10}$, and $R_{11}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and
$R_8$ and $R_{12}$ are each independently —H, halogen, —CN, —$CF_3$, —$OCF_3$, —$NO_2$, alkyl, alkenyl, alkynyl, aryl, heteroaryl, —OAc, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$,
wherein each occurrence of $R_{13}$ is independently alkyl, alkenyl, alkynyl, aryl, or heteroaryl,
wherein each occurrence of $R_{14}$ is independently —H, alkyl, alkenyl, alkynyl, aryl, or heteroaryl,
wherein each occurrence of $R_{15}$ is independently —H, alkyl, alkenyl, alkynyl, aryl, or heteroaryl,
wherein when $R_1$, $R_2$, $R_3$, $R_4$, $R_5$, $R_6$, $R_8$, $R_{11}$, $R_{12}$ are each —H, $R_9$ is —Br, and $R_{10}$ is —OH, then $R_7$ is other than —$CH_3$,
or a pharmaceutically acceptable salt or ester thereof.

The present invention also provides a method of inhibiting the growth of a fungus comprising contacting the fungus with an effective amount of a compound having the structure:

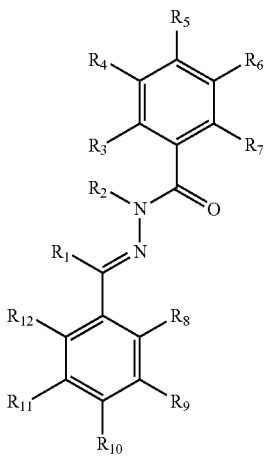

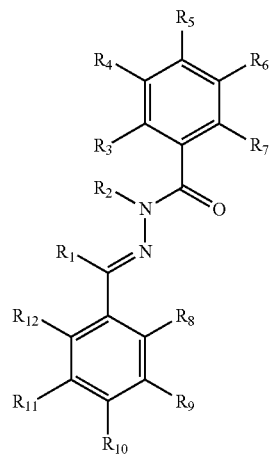

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}HR_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibit the growth of the fungus.

The present invention also provides a method of inhibiting fungal shingolipid synthesis in a fungus comprising contacting the fungus with an effective amount of a compound having the structure:

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R^{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibit shingolipid synthesis in the fungus.

The present invention also provides a method of inhibiting fungal shingolipid synthesis in a fungus in a mammal without substantially inhibiting mammalian shingolipid synthesis comprising administering to the mammal an effective amount of a compound having the structure:

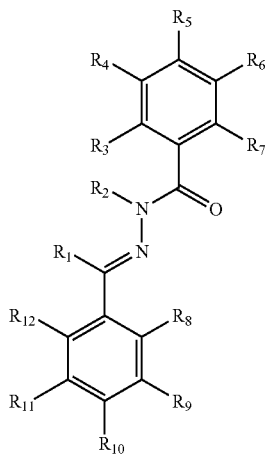

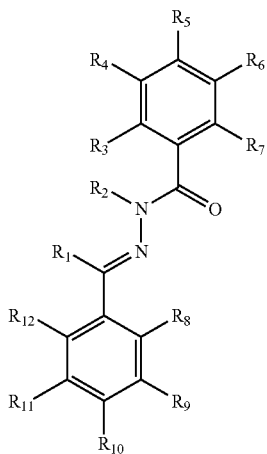

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibit fungal shingolipid synthesis in the fungus in the mammal without substantially inhibiting mammalian shingolipid synthesis.

The present invention further provides method of inhibiting the growth of a fungus comprising contacting the fungus with an effective amount of a compound having the structure:

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt or ester thereof, so as to thereby inhibit the growth of the fungus, wherein the fungus is other than *Cryptococcus neoformans*.

The present invention further provides a method of inhibiting fungal shingolipid synthesis in a fungus comprising contacting the fungus with an effective amount of a compound having the structure:

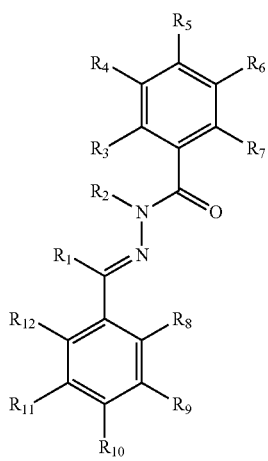

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt or ester thereof, so as to thereby inhibit shingolipid synthesis in the fungus, wherein the fungus is other than *Cryptococcus neoformans*.

The present invention further provides a method of inhibiting fungal shingolipid synthesis in a fungus in a mammal without substantially inhibiting mammalian shingolipid synthesis comprising administering to the mammal an effective amount of a compound having the structure:

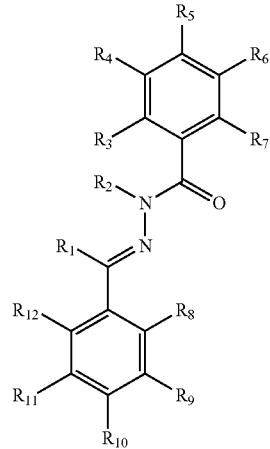

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt or ester thereof, so as to thereby inhibit fungal shingolipid synthesis in the fungus in the mammal without substantially inhibiting mammalian shingolipid synthesis, wherein the fungus is other than *Cryptococcus neoformans*.

The present invention furthermore provides a method of inhibiting the growth of or killing a fungus in a subject afflicted with a fungal infection comprising administering to the subject an effective amount of a compound having the structure:

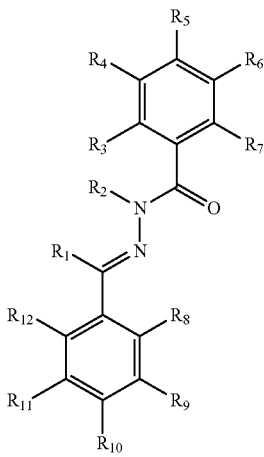

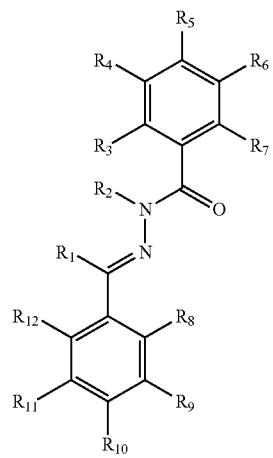

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibiting the growth of or kill the fungus in the subject afflicted with the fungal infection.

The present invention also provides a method of inhibiting the growth of or killing a fungus in a subject afflicted with a fungal infection comprising administering to the subject an effective amount of a compound having the structure:

wherein $R_1$ is —H, alkyl, alkenyl, or alkynyl;

$R_2$ is —H, alkyl, alkenyl, or alkynyl;

$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{16}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt or ester thereof, so as to thereby inhibit the growth of or kill the fungus in the subject afflicted with the fungal infection, wherein the fungus in the subject afflicted with the fungal infection is other than *Cryptococcus neoformans*.

BRIEF DESCRIPTION OF THE FIGURES

FIG. 1A: BHBM and 1 inhibit the synthesis of fungal but not mammalian glucosylceramide. Thin layer chromatography analysis of the synthesis of glucosylceramide (GlcCer) upon in vivo labeling of *C. neoformans* (Cn) or J774 cells with $^3$H-palmitate and treated with BHBM or 1 at the indicated concentrations.

FIG. 1B: Structure of N'-(3-bromo-4-hydroxybenzylidene)-2-methylbenzo-hydrazide (BHBM) and 3-bromo- N'-(3-bromo-4-hydroxybenzylidene) benzohydrazide (1). MIC. Minimum inhibitory concentration; MFC, minimum fungicidal concentration.

FIG. 2A: Killing activity of BHBM and 1. Killing activity was determined using a killing in vitro assay in which the compounds, at the illustrated concentrations, were added to *C. neoformans* cells and tubes incubated at 37° C., 5% $CO_2$ and pH 7.4. Colony forming units (CFU) were counted during the course of 96 hours of incubation.

FIG. 2B: 1 showed higher killing activity than BHBM (A). *, P<0.05, 1 μg/ml of BHBM at 48 h versus 0.25 μg/ml, 1 or 4 μg/ml at 72 h versus 0.25 μg/ml, 4 μg/ml at 96 h versus 0.25 μg/ml; * P<0.05, 1 or 4 μg/ml of 1 at 24 h versus 0.25 μg/ml or drug. Cn, *C. neoformans*.

FIG. 3A: Effect of BHBM and 1 on cryptococcosis. Survival of mice infected with *C. neoformans* (Cn) and receiving 1.2 mg/Kg/day of either BHBM or 1 intraperitoneally. * P<0.01, BHBM or 1 treated brains versus untreated. Statistical analysis for survival studies was performed using Student-Newman-Keuls t test for multiple comparisons using INSTAT.

FIG. 3B: Tissue burden culture of lungs and brains of infected mice were performed at day 25 (untreated) or at day 60 (treated). * P<0.001, BHBM or 1 treated brains versus untreated brains; #P<0.01, BHBM or 1 treated lungs versus untreated lungs. Statistical analysis for CFU data was performed using the analysis of variance (ANOVA).

FIG. 4A: Effect of BHBM and 1 on pneumocystosis. Survival of corticosteroid-immunosuppressed mice after 13 days of BHBM treatment. A significant difference was observed between the BHBM high dose and BHBM low dose treatment groups. C/S, control steroids vehicle treated mice, T/S, Trimethoprim/Sulfamethaxozole.

FIG. 4B-C: Mean asci (B) and nuclei (C) counts after 13 days of BHBM treatment. (C/S) vehicle, negative control. T/S, trimethoprim/Sulfamethaxozole.

FIG. 4D: Survival curves after 14 days of 1 treatment. C/S, control steroids vehicle immunosuppressed mice.

FIG. 4E-F: Mean asci (E) and nuclei (F) counts after 14 days of 1 treatment. * P<0.01, Statistical analysis for survival studies was performed using Student-Newman-Keuls t test for multiple comparisons using INSTAT. Statistical analysis for trophic form and asci counts was performed using the analysis of variance (ANOVA).

FIG. 5A: Effect of BHBM and 1 on candidiasis. Survival of mice infected with *C. albicans* SC 5314 and receiving 1.2 mg/Kg/day of either BHBM or 1 intraperitoneally. * P<0.01, BHBM or 1 treated brains versus untreated. Statistical analysis for survival studies was performed using Student-Newman-Keuls t test for multiple comparisons using INSTAT.

FIG. 5B: Tissue burden culture of organs of infected mice were performed at day 21 of treated mice that survived the infection.

FIG. 6B-H: Mass spectrometry analysis of sphingosines. 9 methyl glucosylceramide - GlcCer (B), C18 dihydroceramide - C18dhCER (C), sphingosine - SPHs (D), sphingosine -1-phosphate - SPH-1-P (E), C18 ceramide - C18 OH-Cer (F), C18 Δ8-ceramide - C18 OH—Δ8-Cer (G), and C18 Δ8-C9-methylceramide -C18 OH-Δ8, 9 Me-Cer (H) in treated and untreated Cn cells. *, P<0.05 versus untreated (no drug) cultures. Statistical analysis for CFU data was performed using the analysis of variance (ANOVA). Statistical significance is accepted at a P value <0.05.

FIG. 7A: Effects of BHBM on Golgi morphology and vesicle secretion in *C. neoformans* and *C. albicans*. A) Control (CT) or BHBM-treated cells were stained with C6-NBD-ceramide (Golgi, green fluorescence or gray in black & white depection) and DAPI (nucleus, blue fluorescence or light gray in black & white depection). Columns 1 and 2 show *C. neoformans*, while columns 3 and 4 show *C. albicans* cells.

FIG. 7B-C: Quantitative determination of vesicular sterols in *C. neoformans* (B) and *C. albicans* (C) secreted vesicles revealed that BHBM treatment efficiently inhibited vesicle secretion. * P<0.05. WF, white field; NBD-Cer, NBD-ceramide.

FIG. 11: Synergistic activity of BHBM and 1 with fluconazole, amphotericin B, caspofungin, tunicamycin and aureobasidin A.

FIG. 14: Liver and kidney function test in the blood of BHBM treated mice that received 1.2 mg/kg/day of BHBM intraperitoneally for 60 days.

FIG. 15: Total leukocytes counts in the blood of BHBM treated and un-infected mice. The mice received 1.2 mg/kg/day of BHBM intraperitoneally for 60 days.

FIG. 16: Erythrocytes and leukocytes measurements in the blood of BHBM treated and un-infected mice. The mice received 1.2 mg/kg/day of BHBM intraperitoneally for 60 days.

FIG. 20A: Survival of CD-4-depleted immunosuppressed mice after 14 days of treatment with 1. Treatment showed improvement in survival. No evidence of drug toxicity was observed. C/S, control vehicle CD4-depleted mice.

FIG. 20B-C: Mean asci (b) and nuclei (c) count after 14 days of treatment. *P<0.05. Statistical analysis for survival studies was performed using Student-Newman-Keuls t test for multiple comparisons using INSTAT. Statistical analysis for trophic form and asci counts was performed using analysis of variance (ANOVA).

FIG. 21: Pharmacokinetics of BHBM in mice, Mean blood concentration-time profiles of BHBM after a single intravenous (IV) 1.6 mg/kg (high dose) or intraperitoneal (IP) 0.8 mg/kg (low IP dose) or 1.6 mg/kg (high IP dose) administration in normal or immunosuppressed (IS) and infected (IN) mice. N=3 mice per group per time point.

FIG. 23: In vitro activity ($MIC_{80}$), solubility, stability and toxicity of compounds BHBM and 1-10.

FIG. 28A-D: Gas ion chromatogram of sterols extracted from untreated and BHBM treated C. Neoformans cells. A, B, C, and D represent the sterol profiles of 0, 1, 2, and 4 μg/mL BHBM C. Neoformans treated H99 wild-type cells, respectively. Lipid extraction was performed as described by Singh et al. (Cell Microbiol. (2012) 14, 4, 500-516). Sterol derivatization, detection, and analysis was performed by GC-MS using methods described by Nes et al. Arch Biochem. Biophys. (2009) 481, 2, 210-218; Singh et al. OMICS (2013) 17, 2, 84-93; and Chang et al. (2014) PLoS Genet. (2014) 10, 4, e1004292. The experiments were performed in duplicate. Structures are: 1. squalene; 2. cholesterol (internal standard); 3. dehyoergosterol; 4. ergosterol; 5. ergosta-7,22-dien-3-ol; 6. ergosta-8-ol; 7. Fecosterol; 8. Ergosta-7-i1; 9. Lanosterol; 10. 4α-methyl episterol; 11. 24-methylenelanost-8-en-3-ol; 12. Putative noreburicol; 13., 14., 15. Unknown sterol intermediates.

FIG. 30A-D: TEM images of C. neoformans (A) untreated or treated with 4 μg/mL of (B) 1 and (C) BHBM for 6 hours. A higher magnification image of BHBM treated cell is shown in (D). White arrows in G show membrane structure, whereas black arrows indicate intracellular vesicles. Black scale bar=500 nm in A, B, and C; 200 nm in D. Representative data of 3 separate experiments.

DETAILED DESCRIPTION OF THE INVENTION

Figure 2C:
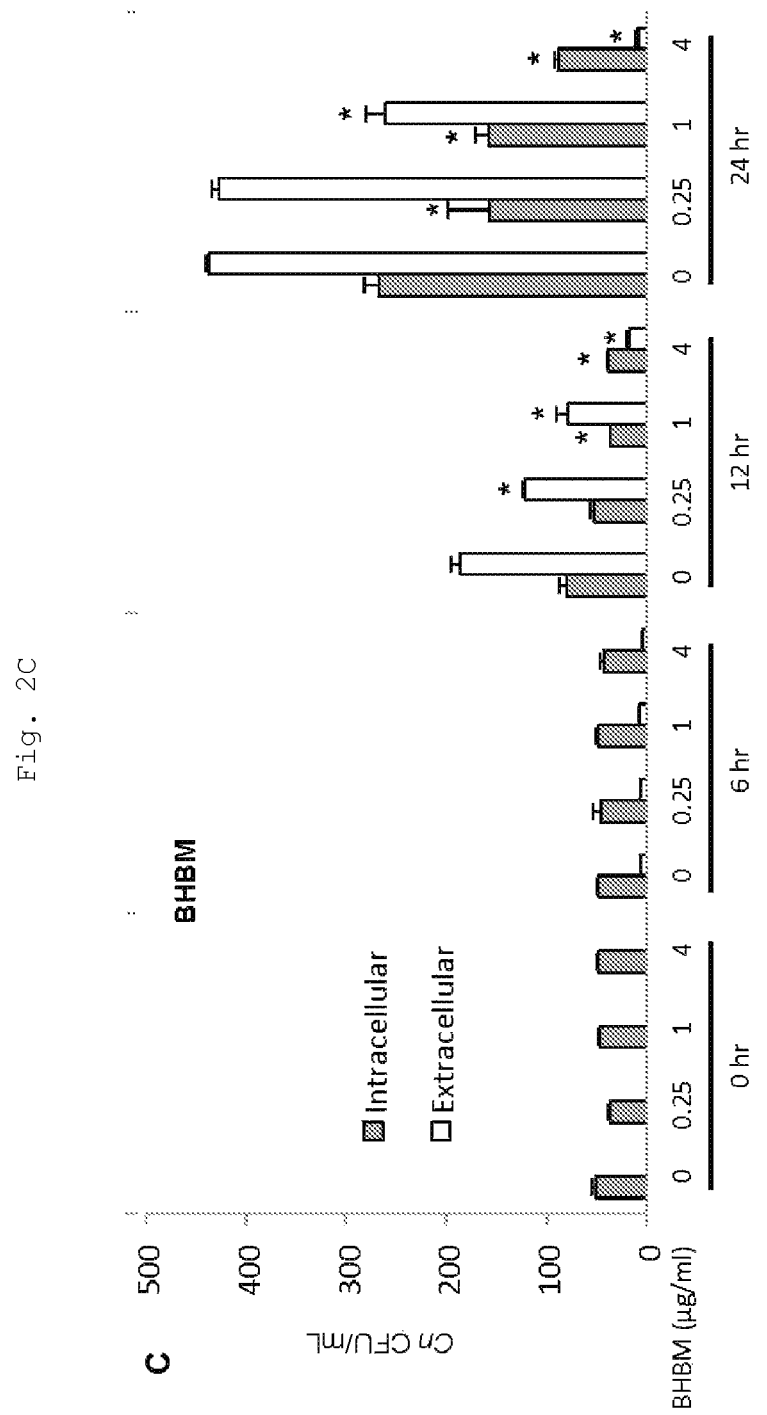
FIG. 2C: Intracellular activity of BHBM was assessed by incubating macrophages internalized with *C. neoformans* with different concentration of BHBM in absence of opsonins. *, P<0.05, extracellular or intracellular treated (0.25, 1 or 4 μg/ml) versus extracellular or intracellular untreated (0 μg/ml), respectively. Statistical analysis was performed using the analysis of variance (ANOVA). Statistical significance is accepted at a P value<0.05.

The present invention provides a compound having the structure:

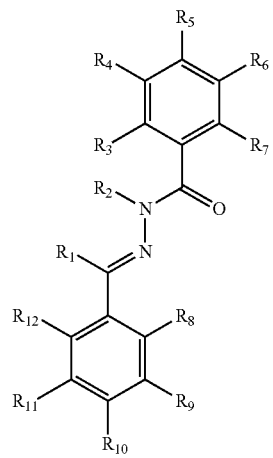

wherein $R_1$ is —H, alkyl, alkenyl, or alkynyl;

$R_2$ is —H, alkyl, alkenyl, or alkynyl;

$R_3$, $R_4$, $R_5$, and $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_9$, $R_{10}$, and $R_{11}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and $R_8$ and $R_{12}$ are each independently —H, halogen, —CN, —$CF_3$, —$OCF_3$, —$NO_2$, alkyl, alkenyl, alkynyl, aryl, heteroaryl, —OAc, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, wherein when $R_1$, $R_2$, $R_3$, $R_4$, $R_5$, $R_6$, $R_8$, $R_{11}$, $R_{12}$ are each —H, $R_9$ is —Br, and $R_{10}$ is —OH, then $R_7$ is other than —$CH_3$, or a pharmaceutically acceptable salt or ester thereof.

In some embodiments, at least one of $R_8$, $R_9$, $R_{10}$, $R_{11}$, and $R_{12}$ are other than —H. In some embodiments, at least two of $R_8$, $R_9$, $R_{10}$, $R_{11}$, and $R_{12}$ are other than —H.

In some embodiments, $R^7$ is $C_2$-$C_{12}$ alkyl or $C_2$-$C_{20}$ alkyl. In some embodiments, $R_1$ is H or —$CH_3$; and $R_2$ is H or —$CH_3$. In some embodiments, $R_1$ is —H; and $R_2$ is —H.

In some embodiments, the compound wherein $R_3$, $R_4$, $R_5$, $R_6$, and $R_7$ are each independently —H, —Br, alkyl, —OH, —$OR_{13}$, or —$NR_{14}R_{15}$; and $R_8$, $R_9$, $R_{10}$, $R_{11}$, and $R_{12}$ are each independently —H, —Br, alkyl, —OH, —$OR_{13}$, or —$NR_{14}R_{15}$, wherein each occurrence of $R_{13}$, $R_{14}$, and $R_{15}$ is alkyl, or a pharmaceutically acceptable salt thereof.

In some embodiments, the compound wherein $R_3$, $R_4$, $R_5$, $R_6$, and $R_7$ are each independently —H, —Br, or alkyl; and $R_8$, $R_9$, $R_{10}$, $R_{11}$, and $R_{12}$ are each independently —H, —Br, —OH, —$OR_{13}$, or —$NR_{14}R_{15}$, wherein each occurrence of $R_{13}$, $R_{14}$, and $R_{15}$ is alkyl, or a pharmaceutically acceptable salt thereof.

In some embodiments, the compound wherein $R_3$, $R_4$, $R_5$, $R_6$, and $R_7$ are each independently —H, —Br, or —$CH_3$; and $R_8$, $R_9$, $R_{10}$, $R_{11}$, and $R_{12}$ are each independently —H, —Br, —OH, —$OCH_3$, or —$N(CH_3)_2$, or a pharmaceutically acceptable salt thereof.

In some embodiments, the compound having the structure:

wherein $R_9$, $R_{10}$, and $R_{11}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$; and $R_8$ and $R_{12}$ are each independently —H, halogen, —CN, —$CF_3$, —$OCF_3$, —$NO_2$, alkyl, alkenyl, alkynyl, aryl, heteroaryl, —OAc, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt thereof.

In some embodiments, the compound wherein $R_8$ and $R_{12}$ are each independently —H, —Br, or —$NR_{14}R_{15}$, $R_9$, $R_{10}$, and $R_{11}$ are each independently —H, —Br, —OH, —$OR_{13}$, or —$NR_{14}R_{15}$, wherein each occurrence of $R_{13}$, $R_{14}$, and $R_{15}$ is alkyl, or a pharmaceutically acceptable salt thereof.

In some embodiments, the compound wherein $R_8$ and $R_{12}$ are each independently —H, —Br, or —$N(CH_3)_2$, $R_9$, $R_{10}$, and $R_{13}$ are each independently —H, —Br, —OH, —$OCH_3$, or —$N(CH_3)_2$, or a pharmaceutically acceptable salt thereof.

In some embodiments, the compound having the structure:

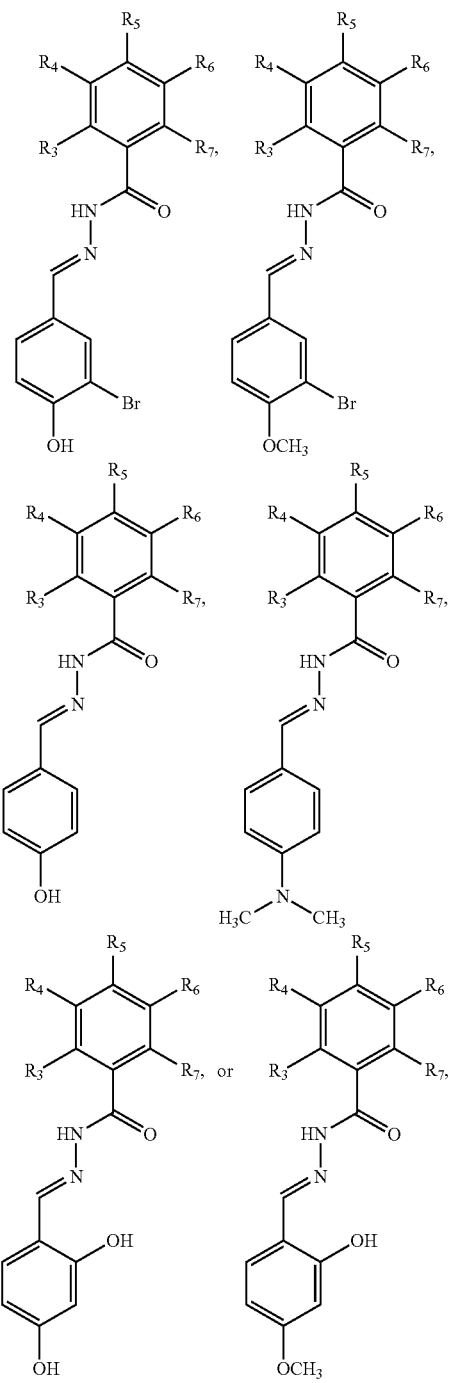

wherein
R$_3$, R$_4$, R$_5$, and R$_6$, and R$_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$, wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt thereof.

In some embodiments, the compound wherein
R$_3$, R$_4$, R$_5$, R$_6$, and R$_7$ are each independently —H, —Br, or alkyl, or a pharmaceutically acceptable salt thereof.

In some embodiments, the compound wherein
R$_3$, R$_4$, R$_5$, R$_6$, and R$_7$ are each independently —H, —Br, or —CH$_3$, or a pharmaceutically acceptable salt thereof.

In some embodiments, the compound having the structure:

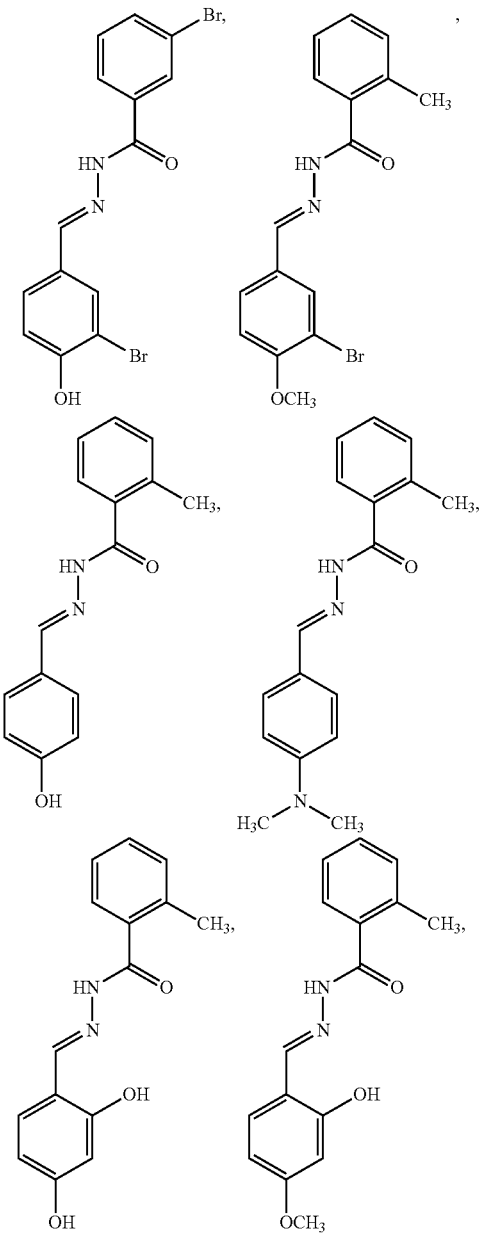

-continued

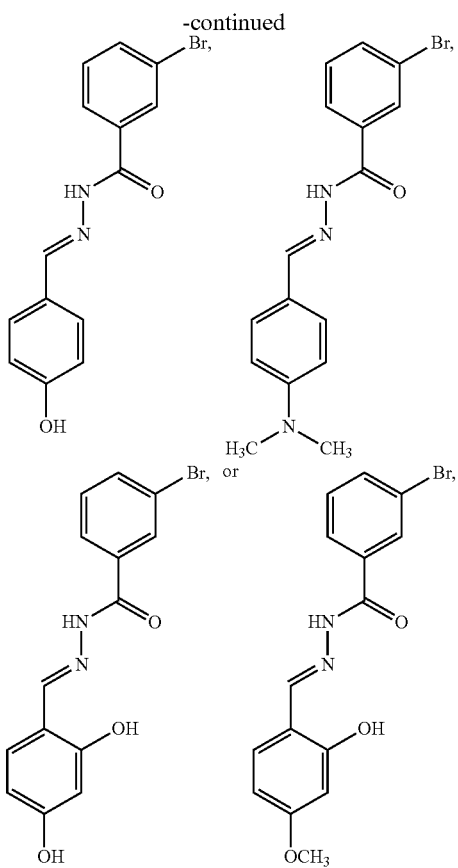

or a pharmaceutically acceptable salt thereof.

In some embodiments, a pharmaceutical composition comprising the compound of the present invention and a pharmaceutically acceptable carrier.

The present invention also provides a method of inhibiting the growth of a fungus comprising contacting the fungus with an effective amount of a compound having the structure:

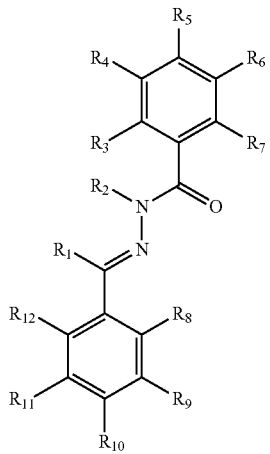

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$;
$R_8$ and $R_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;
$R_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NHCOR$_{12}$, or —CONR$_{14}$R$_{15}$; and
$R_{11}$ and $R_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;
wherein each occurrence of $R_{13}$ is independently alkyl, alkenyl, alkynyl, aryl, or heteroaryl,
wherein each occurrence of $R_{14}$ is independently —H, alkyl, alkenyl, alkynyl, aryl, or heteroaryl,
wherein each occurrence of $R_{15}$ is independently —H, alkyl, alkenyl, alkynyl, aryl, or heteroaryl,
when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —OCH$_3$, then $R_7$ is other than —CH$_3$; and
when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —CH$_3$ or —Br and H, respectively,
or a pharmaceutically acceptable salt or ester thereof, so as to thereby inhibit the growth of the fungus.

The present invention also provides a method of inhibiting fungal shingolipid synthesis in a fungus comprising contacting the fungus with an effective amount of a compound having the structure:

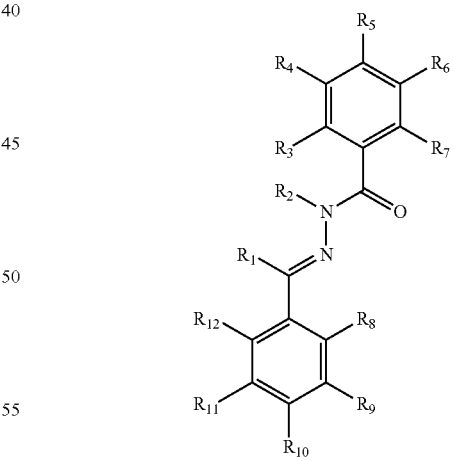

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CM, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibit fungal shingolipid synthesis in the fungus.

The present invention also provides a method of inhibiting fungal shingolipid synthesis in a fungus in a mammal without substantially inhibiting mammalian shingolipid synthesis comprising administering to the mammal an effective amount of a compound having the structure:

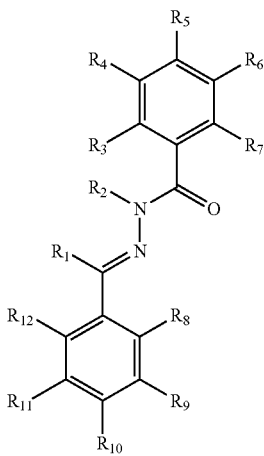

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;

$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;

$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and $R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, when $R_1$, $R_2$, $R_3$, $R_4$, $R_5$, $R_6$, $R_8$, $R_{11}$, $R_{12}$ are each —H, $R_9$ is —Br, and —$R_{10}$ is —OH or —$OCH_3$, then $R_7$ is other than —$CH_3$; and when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively, or a pharmaceutically acceptable salt or ester thereof, so as to thereby inhibit fungal shingolipid synthesis in the fungus in the mammal without substantially inhibiting mammalian shingolipid synthesis.

In some embodiments, the method wherein at least one of $R_8$, $R_9$, $R_{10}$, $R_{11}$, and $R_{12}$ are other than —H. In some embodiments, the method wherein at least two of $R_8$, $R_9$, $R_{10}$, $R_{11}$, and $R_{12}$ are other than —H.

In some embodiments, the method wherein $R_1$ is H or —$CH_3$; and $R_2$ is H or —$CH_3$. In some embodiments, the method wherein $R_1$ is —H; and $R_2$ is —H. In some embodiments, the method wherein $R_7$ is $C_2$-$C_{12}$ alkyl or $C_2$-$C_{20}$ alkyl.

In some embodiments, the method wherein $R_3$, $R_4$, $R_5$, $R_6$, and $R_7$ are each independently —H, —Br, alkyl, —OH, —$OR_{13}$, or —$NR_{14}R_{15}$; and $R_8$, $R_9$, $R_{10}$, $R_{11}$, and $R_{12}$ are each independently —H, —Br, alkyl, —OH, or —$OR_{13}$, wherein each occurrence of $R_{13}$, $R_{14}$, and $R_{15}$ is alkyl, or a pharmaceutically acceptable salt thereof.

In some embodiments, the method wherein $R_3$, $R_4$, $R_5$, $R_6$, and $R_7$ are each independently —H, —Br, or alkyl; and $R_8$, $R_9$, $R_{10}$, $R_{11}$, and $R_{12}$ are each independently —H, —Br, —OH, or —$OR_{13}$, wherein $R_{13}$ is alkyl, or a pharmaceutically acceptable salt thereof.

In some embodiments, the method wherein $R_3$, $R_4$, $R_5$, $R_6$, and $R_7$ are each independently —H, —Br, or —$CH_3$; and $R_8$, $R_9$, $R_{10}$, $R_{11}$, and $R_{12}$ are each independently —H, —Br, —OH, or —O $CH_3$, or a pharmaceutically acceptable salt thereof.

In some embodiments, the method wherein the compound has the structure:

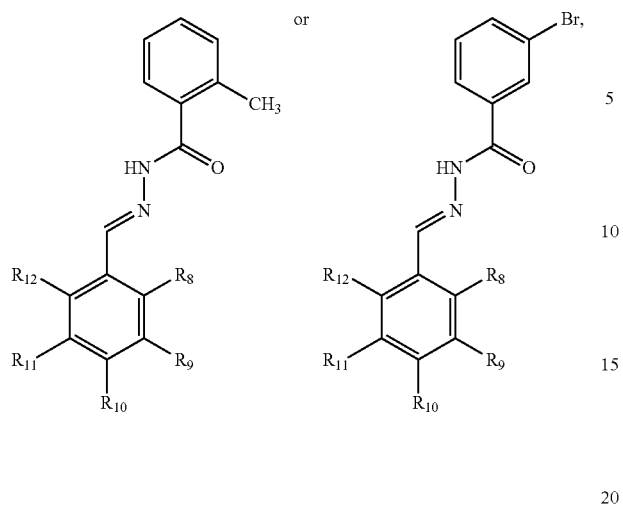

wherein $R_8$ and $R_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;

$R_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NHCOR$_{12}$, or —CONR$_{14}$R$_{15}$; and $R_{11}$ and $R_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$R$_{14}$R$_{15}$, —NH$_2$, —NHR$_{13}$, NR$_{14}$R$_{15}$, —NHCOR$_{12}$, or —CONR$_{14}$R$_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt thereof.

In sane embodiments, the method wherein $R_8$ and $R_{12}$ are each independently —H, —Br, or —NR$_{14}$R$_{15}$, $R_9$, $R_{10}$, and $R_{11}$ are each independently —H, —Br, —OH, or —OR$_{13}$, wherein each occurrence of $R_{13}$, $R_{14}$, and $R_{15}$ is alkyl, or a pharmaceutically acceptable salt thereof.

In some embodiments, the method wherein $R_8$ and $R_{12}$ are each independently —H, —Br, or —N(CH$_3$)$_2$, $R_9$, $R_{10}$, and $R_{11}$ are each independently —H, —Br, —OH, or —OCH$_3$, or a pharmaceutically acceptable salt thereof.

In some embodiments, the method wherein the compound has the structure:

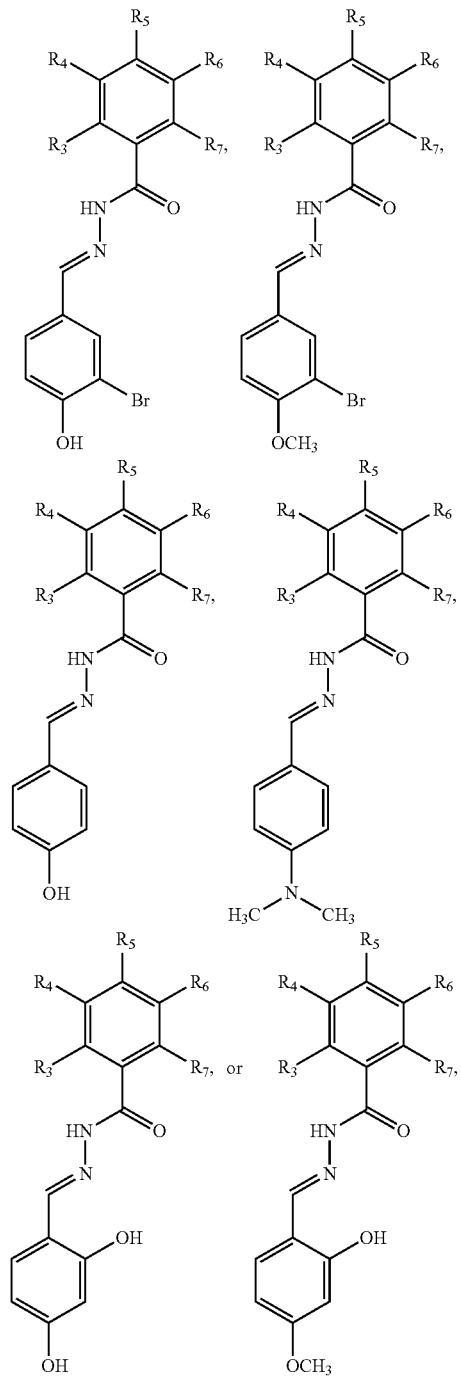

wherein $R_3$, $R_4$, $R_5$, and $R_6$, and $R_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl,
or a pharmaceutically acceptable salt thereof.

In some embodiments, the method wherein
$R_3$, $R_4$, $R_5$, $R_6$, and $R_7$ are each independently —H, —Br, or alkyl,
or a pharmaceutically acceptable salt thereof.

In some embodiments, the method wherein
$R_3$, $R_4$, $R_5$, $R_6$, and $R_7$ are each independently —H, —Br, or —$CH_3$,
or a pharmaceutically acceptable salt thereof.

In some embodiments, the method wherein the compound has the structure:

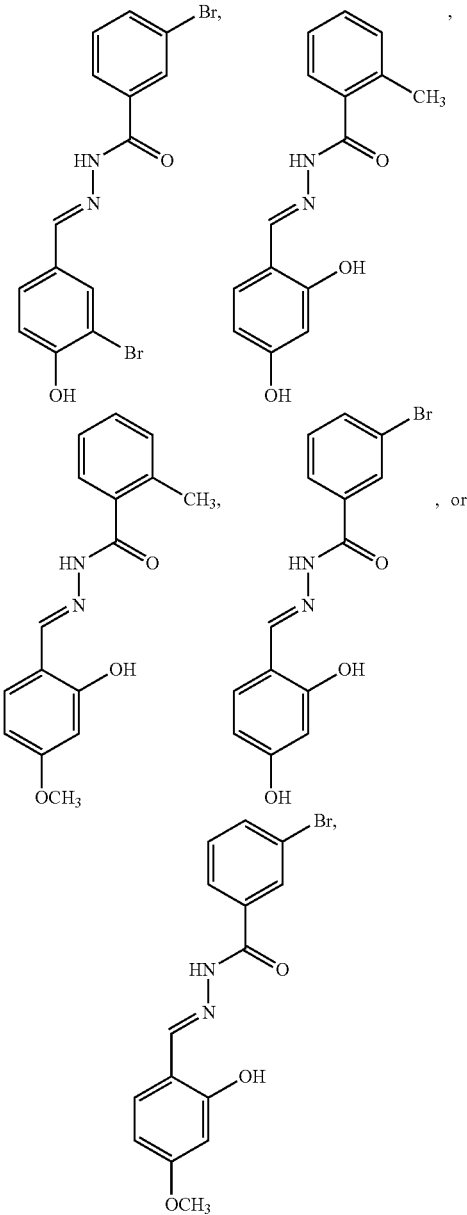

or a pharmaceutically acceptable salt thereof.

In some embodiments, the method further comprising contacting the fungus with an amount of an anti-fungal agent.

In some embodiments, the method wherein the amount of the compound and the amount of the anti-fungal agent when taken together is more effective to inhibit the growth of the fungus than the anti-fungal agent alone.

In some embodiments, the method wherein the anti-fungal agent is fluconazole, amphotericin B, caspofungin, tunicamycin or aureobasidin A.

In some embodiments, the method wherein the fungus is *Cryptococcus Neoformans, Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., a dimorphic fungi or a mucorales fungi.

In some embodiments, the method wherein the fungal shingolipid is glucosylceramide (GlcCer).

The present invention further provides method of inhibiting the growth of a fungus comprising contacting the fungus with an effective amount of a compound having the structure:

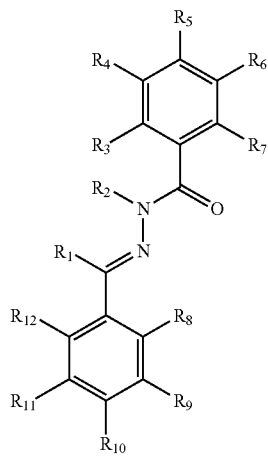

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CM, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;
$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$;
$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NR_{14}R_{15}$, —$NHCOR_{12}$, or —$CONR_{14}R_{15}$; and
$R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$, wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt or ester thereof, so as to thereby inhibit the growth of the fungus, wherein the fungus is other than *Cryptococcus neoformans*.

The present invention further provides a method of inhibiting fungal shingolipid synthesis in a fungus comprising contacting the fungus with an effective amount of a compound having the structure:

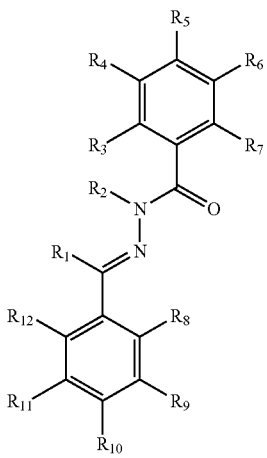

wherein

R$_1$ is —H, alkyl, alkenyl, or alkynyl;

R$_2$ is —H, alkyl, alkenyl, or alkynyl;

R$_3$, R$_4$, R$_5$, R$_6$, and R$_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$;

R$_8$ and R$_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;

R$_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$; and R$_{11}$ and R$_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$, wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt or ester thereof, so as to thereby inhibit shingolipid synthesis in the fungus, wherein the fungus is other than *Cryptococcus neoformans*.

The present invention further provides a method of inhibiting fungal shingolipid synthesis in a fungus in a mammal without substantially inhibiting mammlian shingolipid synthesis comprising administering to the mammal an effective amount of a compound having the structure:

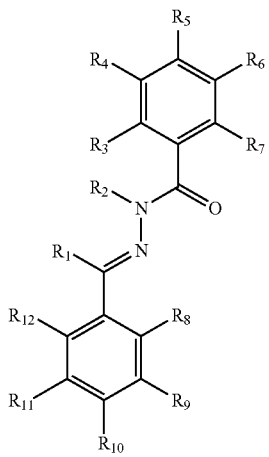

wherein

R$_1$ is —H, alkyl, alkenyl, or alkynyl;

R$_2$ is —H, alkyl, alkenyl, or alkynyl;

R$_3$, R$_4$, R$_5$, R$_6$, and R$_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$;

R$_8$ and R$_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$;

R$_{10}$ is —H, halogen, —CN, —CF$_3$, —OCF$_3$, —NO$_2$, alkyl, alkenyl, alkynyl, aryl, heteroaryl, —OH, —OAc, —OR$_n$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$; and R$_{11}$ and R$_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$, wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt or ester thereof, so as to thereby inhibit fungal shingolipid synthesis in the fungus in the mammal without substantially inhibiting mammalian shingolipid synthesis, wherein the fungus is other than *Cryptococcus neoformans*.

In some embodiments, the method wherein at least one of $R_8$, $R_9$, $R_{10}$, $R_{11}$, and $R_{12}$ are other than —H. In some embodiments, the method wherein at least two of $R_8$, $R_9$, $R_{10}$, $R_{11}$, and $R_{12}$ are other than —H.

In some embodiments, the method wherein $R_1$ is H or —CH$_3$; and $R_2$ is —H or —CH$_3$. In some embodiments, the method wherein $R_1$ is —H; and $R_2$ is —H. In some embodiments, the method wherein $R_7$ is $C_2$-$C_{12}$ alkyl or $C_2$-$C_{20}$ alkyl.

In some embodiments, the method wherein
$R_3$, $R_4$, $R_5$, $R_6$, and $R_7$ are each independently —H, —Br, alkyl, —OH, —OR$_{13}$, or —NR$_{14}$R$_{15}$; and
$R_8$, $R_9$, $R_{10}$, $R_{11}$, and $R_{12}$ are each independently —H, —Br, alkyl, —OH, —OR$_{13}$ or NR$_{14}$R$_{15}$,
wherein each occurrence of $R_{13}$, $R_{14}$, and $R_{15}$ is alkyl,
or a pharmaceutically acceptable salt thereof.

In some embodiments, the method wherein
$R_3$, $R_4$, $R_5$, $R_6$, and $R_7$ are each independently —H, —Br, or —CH$_3$; and
$R_8$, $R_9$, $R_{10}$, $R_{11}$, and $R_{12}$ are each independently —H, —Br, —OH, —OCH$_3$, or —N(CH$_3$)$_2$,
or a pharmaceutically acceptable salt thereof.

In some embodiments, the method wherein the compound has the structure:

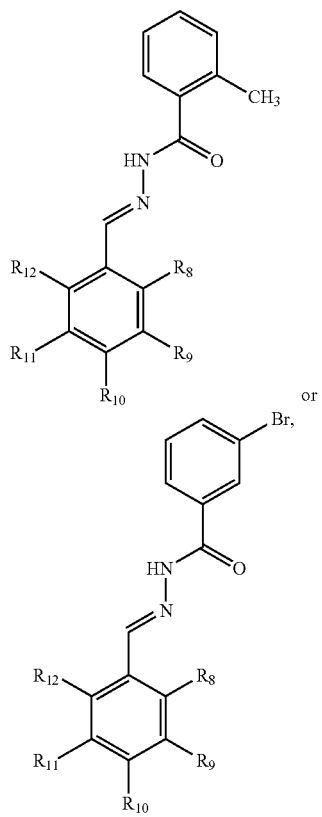

wherein
$R_8$ and $R_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$;

$R_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$; and $R_{11}$ and $R_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$,
wherein each occurrence of $R_{13}$ is independently alkyl, alkenyl, alkynyl, aryl, or heteroaryl,
wherein each occurrence of $R_{14}$ independently —H, alkyl, alkenyl, alkynyl, aryl, or heteroaryl,
wherein each occurrence of $R_{15}$ is independently —H, alkyl, alkenyl, alkynyl, aryl, or heteroaryl,
or a pharmaceutically acceptable salt thereof.

In some embodiments, the method wherein
$R_8$, $R_9$, $R_{10}$, $R_{11}$, and $R_{12}$ are each independently —H, —Br, alkyl, —OH, —OR$_{13}$ or NR$_{14}$R$_{15}$,
wherein each occurrence of $R_{13}$, $R_{14}$, and $R_{15}$ is alkyl,
or a pharmaceutically acceptable salt thereof.

In some embodiments, the method wherein
$R_8$, $R_9$, $R_{10}$, $R_{11}$, and $R_{12}$ are each independently —H, —Br, —OH, —OCH$_3$, or —N(CH$_3$)$_2$,
or a pharmaceutically acceptable salt thereof.

In some embodiments, the method wherein the compound has the structure:

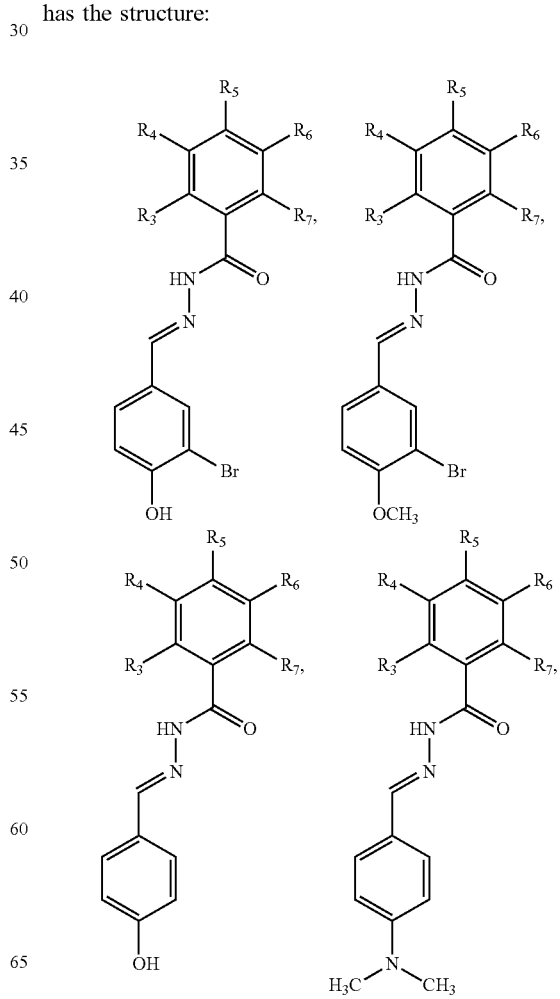

-continued

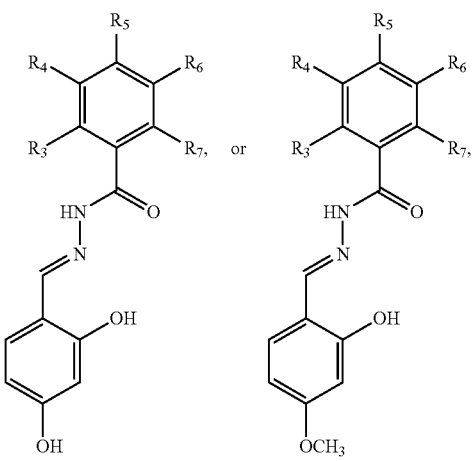

wherein $R_3$, $R_4$, $R_5$, and $R_6$, and $R_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt thereof.

In some embodiments, the method wherein $R_3$, $R_4$, $R_5$, $R_6$, and $R_7$ are each independently —H, —Br, or alkyl, or a pharmaceutically acceptable salt thereof.

In some embodiments, the method wherein $R_3$, $R_4$, $R_5$, $R_6$, and $R_7$ are each independently —H, —Br, or —CH$_3$, or a pharmaceutically acceptable salt thereof.

In some embodiments, the method wherein the compound has the structure:

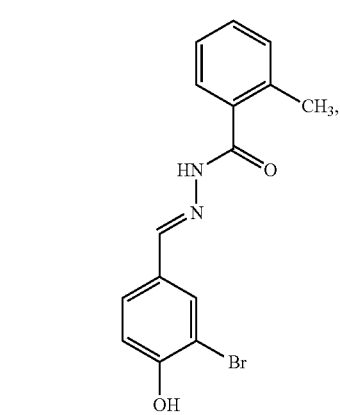

-continued

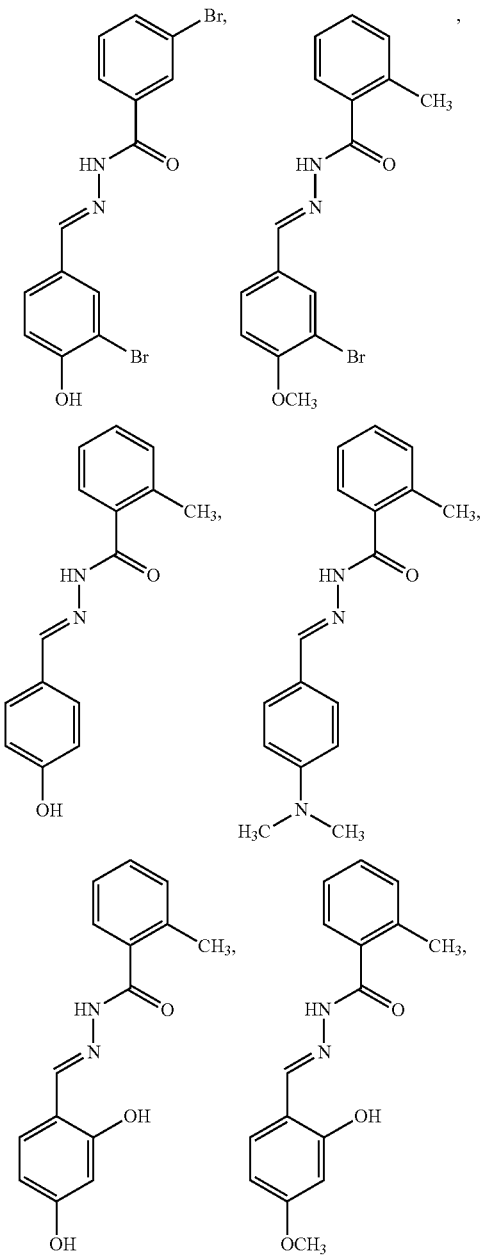

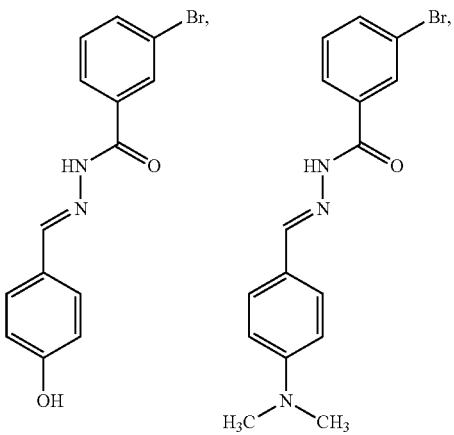

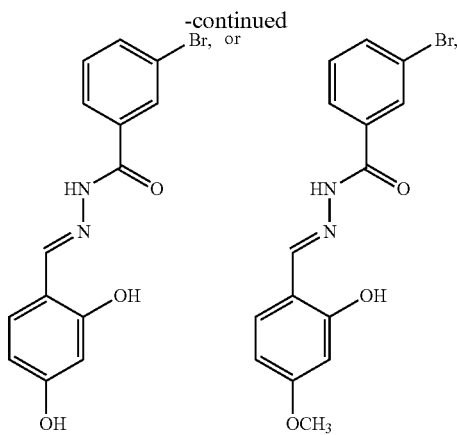

or a pharmaceutically acceptable salt thereof.

In some embodiments, the method further comprising contacting the fungus with an amount of an anti-fungal agent.

In some embodiments, the method wherein the amount of the compound and the amount of the anti-fungal agent when taken together is more effective to inhibit the growth of the fungus than the anti-fungal agent alone.

In some embodiments, the method wherein the anti-fungal agent is fluconazole, amphotericin B, caspofungin, tunicamycin or aureobasidin A.

In some embodiments, the method wherein the fungus is *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., a dimorphic fungi or a mucorales fungi.

In some embodiments, the method wherein the fungal shingolipid is glucosylceramide (GlcCer).

The present invention furthermore provides a method of inhibiting the growth of or killing a fungus in a subject afflicted with a fungal infection comprising administering to the subject an effective amount of a compound having the structure:

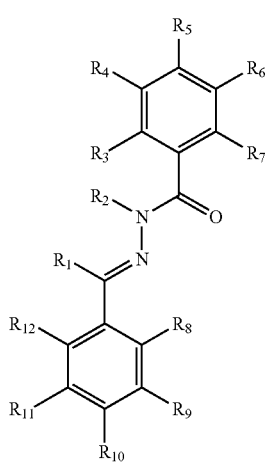

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$;
$R_8$ and $R_9$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;
$R_{10}$ is —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, —$NHCOR_{12}$, or —$CONR_{14}R_{15}$; and
$R_{11}$ and $R_{12}$ are each independently —H, halogen, —CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$SO_2NR_{14}R_{15}$, —$NH_2$, —$NHR_{13}$, $NR_{14}R_{15}$, —$NHCOR_{12}$, or —$CONR_{14}R_{15}$;
wherein each occurrence of $R_{13}$ is independently alkyl, alkenyl, alkynyl, aryl, or heteroaryl,
wherein each occurrence of $R_{14}$ is independently —H, alkyl, alkenyl, alkynyl, aryl, or heteroaryl,
wherein each occurrence of $R_{15}$ is independently —H, alkyl, alkenyl, alkynyl, aryl, or heteroaryl,
when $R_1$, $R_2$, $R_3$, $R_4$, $R_5$, $R_6$, $R_8$, $R_{11}$, $R_{12}$ are each —H, $R_9$ is —Br, and —$R_{10}$ is —$OCH_3$, then $R_7$ is other than —$CH_3$; and
when $R_1$, $R_2$, $R_3$, $R_4$, $R_5$, $R_8$, $R_9$, $R_{11}$, and $R_{12}$ are each —H, and —$R_{10}$ is OH, then $R_6$ and $R_7$ are other than —H and —$CH_3$ or —Br and H, respectively,
or a pharmaceutically acceptable salt thereof, so as to thereby inhibiting the growth of or kill the fungus in the subject afflicted with the fungal infection.

In some embodiments, the method wherein at least one of $R_8$, $R_9$, $R_{10}$, $R_{11}$, and $R_{12}$ are other than —H. In some embodiments, the method wherein at least two of $R_8$, $R_9$, $R_{10}$, $R_{11}$, and $R_{12}$ are other than —H.

In some embodiments, the method wherein $R_1$ is —H or —$CH_3$; and $R_2$ is —H or —$CH_3$. In some embodiments, the method wherein $R_3$ is —H; and $R_2$ is —H.

In some embodiments, the method wherein $R_7$ is $C_2$-$C_{12}$ alkyl or $C_2$-$C_{20}$ alkyl. In some embodiments, the method wherein $R_3$, $R_4$, $R_5$, $R_6$, and $R_7$ are each independently —H, —Br, alkyl, —OH, —$OR_{13}$, or —$NR_{14}R_{15}$; and
$R_8$, $R_9$, $R_{10}$, $R_{11}$, and $R_{12}$ are each independently —H, —Br, alkyl, —OH, or —$OR_{13}$,
wherein each occurrence of $R_{13}$, $R_{14}$, and $R_{15}$ is alkyl,
or a pharmaceutically acceptable salt thereof.

In some embodiments, the method
wherein $R_3$, $R_4$, $R_5$, $R_6$, and $R_7$ are each independently —H, —Br, or alkyl; and
$R_8$, $R_9$, $R_{10}$, $R_{11}$, and $R_{12}$ are each independently —H, —Br, —OH, or —$OR_{13}$,
wherein $R_{13}$ is alkyl,
or a pharmaceutically acceptable salt thereof.

In some embodiments, the method
wherein $R_3$, $R_4$, $R_5$, $R_6$, and $R_7$ are each independently —H, —Br, or —$CH_3$; and
$R_8$, $R_9$, $R_{10}$, $R_{11}$, and $R_{12}$ are each independently —H, —Br, —OH, or —O $CH_3$,
or a pharmaceutically acceptable salt thereof.

In some embodiments, the method wherein the compound has the structure:

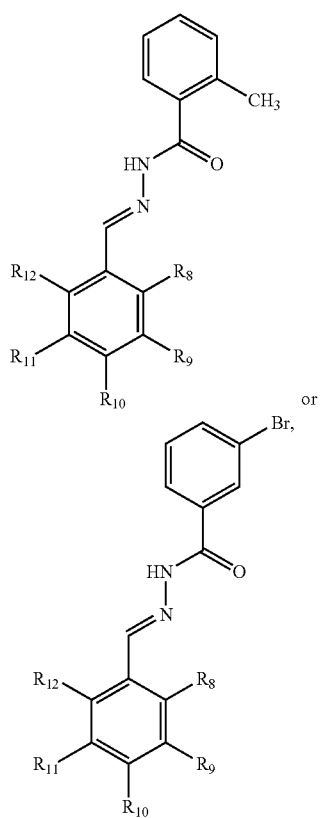

or wherein
$R_8$ and $R_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;

$R_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NHCOR$_{12}$, or —CONR$_{14}$R$_{15}$; and $R_{11}$ and $R_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;
wherein each occurrence of $R_{13}$ is independently alkyl, alkenyl, alkynyl, aryl, or heteroaryl,
wherein each occurrence of $R_{14}$ is independently —H, alkyl, alkenyl, alkynyl, aryl, or heteroaryl,
wherein each occurrence of $R_{15}$ is independently —H, alkyl, alkenyl, alkynyl, aryl, or heteroaryl,
or a pharmaceutically acceptable salt thereof.

In some embodiments, the method
wherein $R_8$ and $R_{12}$ are each independently —H, —Br, or —NR$_{14}$R$_{15}$,
$R_9$, $R_{10}$, and $R_{11}$ are each independently —H, —Br, —OH, or —OR$_{13}$,
wherein each occurrence of $R_{13}$, $R_{14}$, and $R_{15}$ is alkyl, or a pharmaceutically acceptable salt thereof.

In some embodiments, the method
wherein $R_8$ and $R_{12}$ are each independently —H, —Br, or —N(CH$_3$)$_2$, $R_9$, $R_{10}$, and $R_{11}$ are each independently —H, —Br, —OH, or —OCH$_3$,
or a pharmaceutically acceptable salt thereof.

In some embodiments, the method wherein the compound has the structure:

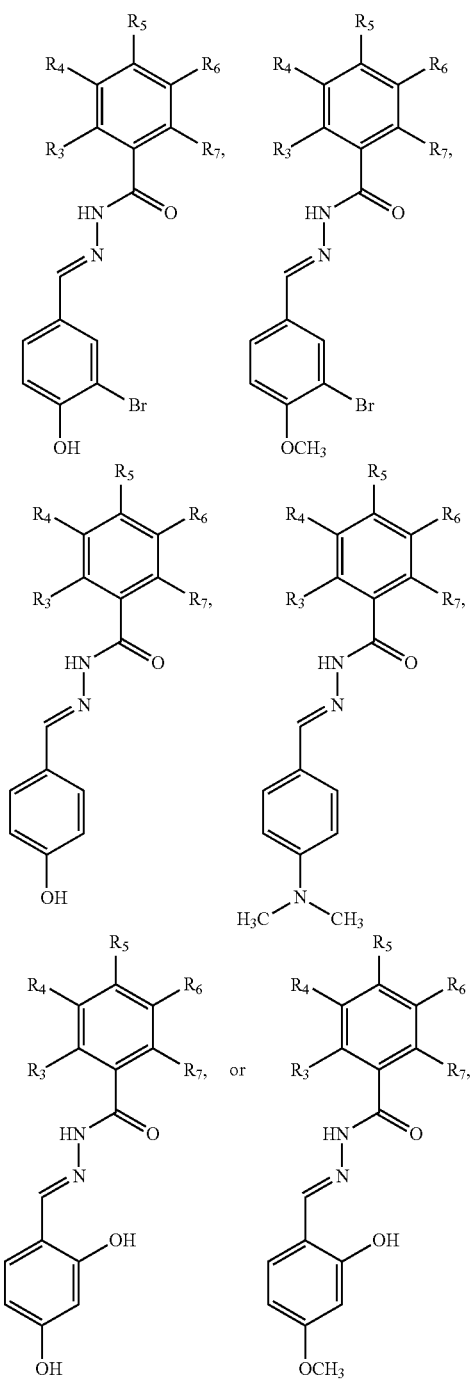

wherein
$R_3$, $R_4$, $R_5$, and $R_6$, and $R_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$, wherein each occurrence of $R_{13}$ is independently alkyl, alkenyl, alkynyl, aryl, or heteroaryl,
wherein each occurrence of $R_{14}$ is independently —H, alkyl, alkenyl, alkynyl, aryl, or heteroaryl,
wherein each occurrence of $R_{15}$ is independently —H, alkyl, alkenyl, alkynyl, aryl, or heteroaryl,
or a pharmaceutically acceptable salt thereof.
In some embodiments, the method
wherein $R_3$, $R_4$, $R_5$, $R_6$, and $R_7$ are each independently —H, —Br, or alkyl,
or a pharmaceutically acceptable salt thereof.
In some embodiments, the method
wherein $R_3$, $R_4$, $R_5$, $R_6$, and $R_7$ are each independently —H, —Br, or —CH$_3$,
or a pharmaceutically acceptable salt thereof.
In some embodiments, the method wherein the compound has the structure:

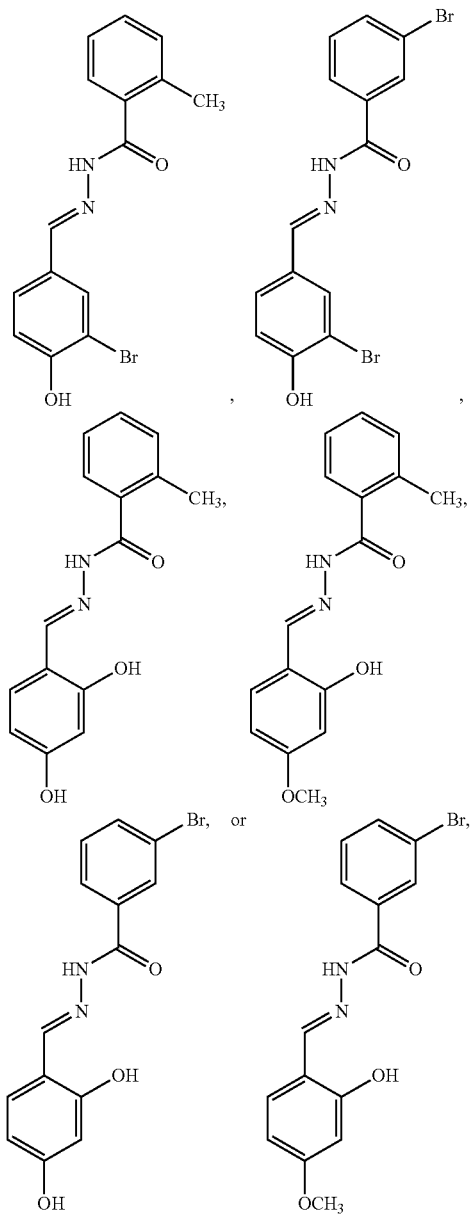

or a pharmaceutically acceptable salt thereof.

In some embodiments, the method further comprising administering an effective amount of an anti-fungal agent.

In some embodiments, the method wherein the amount of the compound and the amount of the anti-fungal agent when taken together is more effective to treat the subject than when the anti-fungal agent is administered alone.

In some embodiments, the method wherein the amount of the compound and the amount of the anti-fungal agent when taken together is effective to reduce a clinical symptom of the fungal infection in the subject.

In some embodiments, the method wherein the anti-fungal agent is fluconazole, amphotericin B, caspofungin, tunicamycin or aureobasidin A.

In some embodiments, the method wherein the fungal infection is caused by *Candida, Aspergillus, Cryptococcus, Histoplasma, Pneumocystis, Stachybotrys* or *Mycrorales* fungus.

In some embodiments, the method wherein the fungal infection is caused by *Cryptococcus Neoformans*.

In some embodiments, the method wherein the fungal infection is *Cryptococcus neoformans* cryptococcosis.

In some embodiments, the method wherein the fungal infection is Aspergillosis, Blastomycosis, Candidiasis, Coccidioidomycosis, *Cryptococcus gattii* cryptococcosis, Fungal Keratitis, Dermatophytes, Histoplasmosis, Mucormycosis, Pneumocystis pneumonia (PCP), or Sporotrichosis.

In some embodiments, the method wherein the fungal infection is caused by *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., or dimorphic fungi.

The present invention also provides a method of inhibiting the growth of or killing a fungus in a subject afflicted with a fungal infection comprising administering to the subject an effective amount of a compound having the structure:

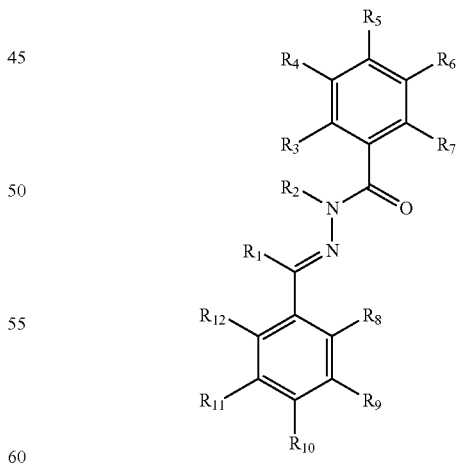

wherein
$R_1$ is —H, alkyl, alkenyl, or alkynyl;
$R_2$ is —H, alkyl, alkenyl, or alkynyl;
$R_3$, $R_4$, $R_5$, $R_6$, and $R_7$ are each independently —H, halogen, CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —NH$_2$, —NHR$_{13}$, —NR$_{14}$R$_{15}$, —NHCOR$_{12}$, or —CONR$_{14}$R$_{15}$;

R$_8$ and R$_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;

R$_{10}$ is —H, halogen, —CN, —CF$_3$, —OCF$_3$, —NO$_2$, alkyl, alkenyl, alkynyl, aryl, heteroaryl, —OH, —OAc, —OR$_u$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$; and R$_{11}$ and R$_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, NR$_{14}$R$_{15}$, —NHCOR$_{12}$, or —CONR$_{14}$R$_{15}$;

wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt or ester thereof, so as to thereby inhibit the growth of or kill the fungus in the subject afflicted with the fungal infection, wherein the fungus in the subject afflicted with the fungal infection is other than *Cryptococcus neoformans.*

In some embodiments, the method wherein at least one of R$_8$, R$_9$, R$_{10}$, R$_{11}$, and R$_{12}$ are other than —H. In some embodiments, the method wherein at least two of R$_8$, R$_9$, R$_{10}$, R$_{11}$, and R$_{12}$ are other than —H.

In some embodiments, the method wherein R$_1$ is —H or —CH$_3$; and R$_2$ is —H or —CH$_3$. In some embodiments, the method wherein R$_1$ is —H; and R$_2$ is —H.

In some embodiments, the method wherein R$_7$ is C$_2$-C$_{12}$ alkyl or C$_2$-C$_{20}$ alkyl.

In some embodiments, the method wherein R$_3$, R$_4$, R$_5$, R$_6$, and R$_7$ are each independently —H, —Br, alkyl, —OH, —OR$_{13}$, or —NR$_{14}$R$_{15}$; and R$_8$, R$_9$, R$_{10}$, R$_{11}$, and R$_{12}$ are each independently —H, —Br, alkyl, —OH, —OR$_{13}$ or NR$_{14}$R$_{15}$, wherein each occurrence of R$_{13}$, R$_{14}$, and R$_{15}$ is alkyl, or a pharmaceutically acceptable salt thereof.

In some embodiments, the method wherein R$_3$, R$_4$, R$_5$, R$_6$, and R$_7$ are each independently —H, —Br, or alkyl; and R$_8$, R$_9$, R$_{10}$, R$_{11}$, and R$_{12}$ are each independently —H, —Br, —OH, —OR$_{13}$, or NR$_{14}$R$_{15}$, wherein each occurrence of R$_{13}$, R$_{14}$, and R$_{15}$ is alkyl, or a pharmaceutically acceptable salt thereof.

In some embodiments, the method wherein R$_3$, R$_4$, R$_5$, R$_6$, and R$_7$ are each independently —H, —Br, or —CH$_3$; and R$_8$, R$_9$, R$_{10}$, R$_{11}$, and R$_{12}$ are each independently —H, —Br, —OH, —OCH$_3$, or —N(CH$_3$)$_2$, or a pharmaceutically acceptable salt thereof.

In some embodiments, the method wherein the compound has the structure:

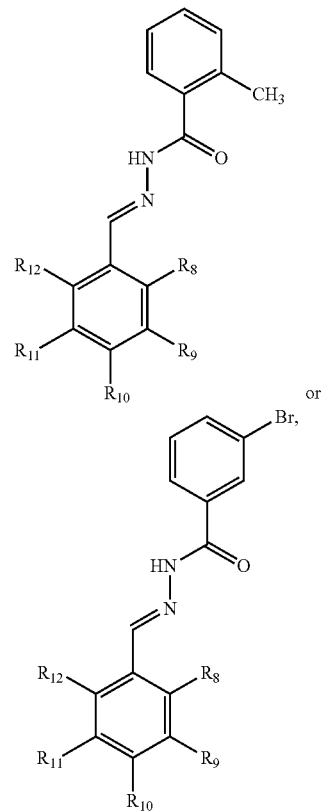

wherein

R$_8$ and R$_9$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$;

R$_{10}$ is —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$; and R$_{11}$ and R$_{12}$ are each independently —H, halogen, —CN, —CF$_3$, —OCF$_3$, —NO$_2$, alkyl, alkenyl, alkynyl, aryl, heteroaryl, —OH, —OAc, —OR$_{13}$, —COR$_{13}$, —SH, —SR$_{13}$, —SO$_2$R$_{13}$, —SO$_2$NR$_{14}$R$_{15}$, —NH$_2$, —NHR$_{13}$, —NR$_{14}$R$_{15}$, —NHCOR$_{12}$, or —CONR$_{14}$R$_{15}$, wherein each occurrence of R$_{13}$ is independently alkyl, alkenyl, alkynyl, aryl, or heteroaryl, wherein each occurrence of R$_{14}$ is independently —H, alkyl, alkenyl, alkynyl, aryl, or heteroaryl, wherein each occurrence of R$_{15}$ is independently —H, alkyl, alkenyl, alkynyl, aryl, or heteroaryl, or a pharmaceutically acceptable salt thereof.

In some embodiments, the method wherein R$_8$, R$_9$, R$_{10}$, R$_{11}$, and R$_{12}$ are each independently —H, —Br, alkyl, —OH, —OR$_{13}$ or NR$_{14}$R$_{15}$, wherein each occurrence of R$_{13}$, R$_{14}$, and R$_{15}$ is alkyl, or a pharmaceutically acceptable salt thereof.

In some embodiments, the method wherein R$_8$, R$_9$, R$_{10}$, R$_{11}$, and R$_{12}$ are each independently —H, —Br, —OH, —OCH$_3$, or —N(CH$_3$)$_2$, or a pharmaceutically acceptable salt thereof.

In some embodiments, the method wherein the compound has the structure:

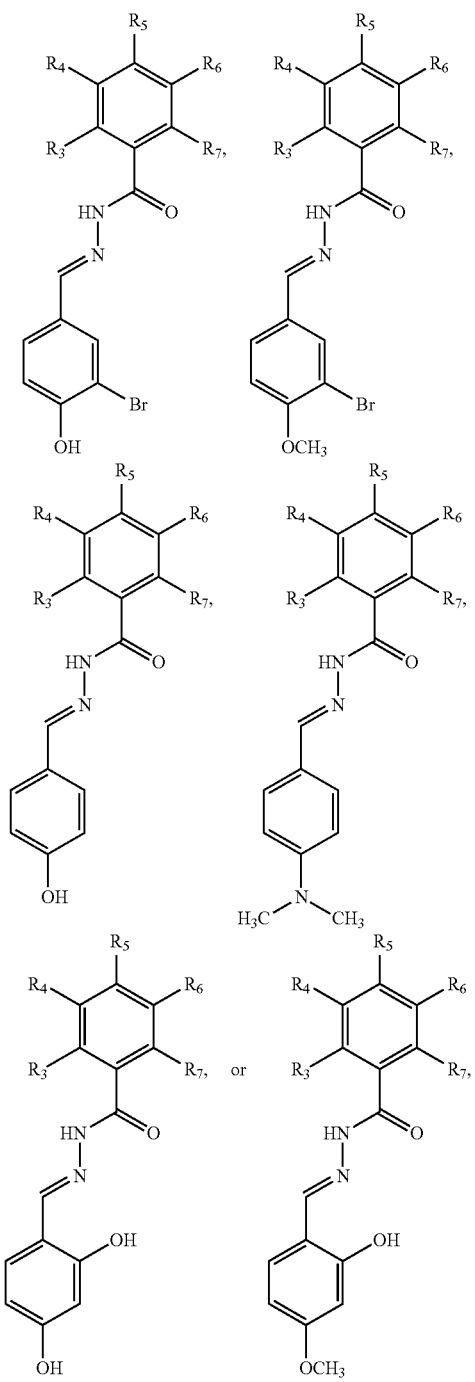

wherein $R_3$, $R_4$, $R_5$, and $R_6$, and $R_7$ are each independently —H, halogen, CN, —$CF_3$, —$OCF_3$, —$NO_2$, alkyl, alkenyl, alkynyl, aryl, heteroaryl, —OH, —OAc, —$OR_{13}$, —$COR_{13}$, —SH, —$SR_{13}$, —$SO_2R_{13}$, —$NH_2$, —$NHR_{13}$, —$NR_{14}R_{15}$, —$NHCOR_{12}$, or —$CONR_{14}R_{15}$, wherein each occurrence of $R_{13}$ is independently alkyl, alkenyl, alkynyl, aryl, or heteroaryl, wherein each occurrence of $R_{14}$ is independently —H, alkyl, alkenyl, alkynyl, aryl, or heteroaryl, wherein each occurrence of $R_{15}$ is independently —H, alkyl, alkenyl, alkynyl, aryl, or heteroaryl, or a pharmaceutically acceptable salt thereof.

In sane embodiments, the method
wherein $R_3$, $R_4$, $R_5$, $R_6$, and $R_7$ are each independently —H, —Br, or alkyl,
or a pharmaceutically acceptable salt thereof.

In some embodiments, the method
wherein $R_3$, $R_4$, $R_5$, $R_6$, and $R_7$ are each independently —H, —Br, or —$CH_3$,
or a pharmaceutically acceptable salt thereof.

In some embodiments, the method wherein the compound has the structure:

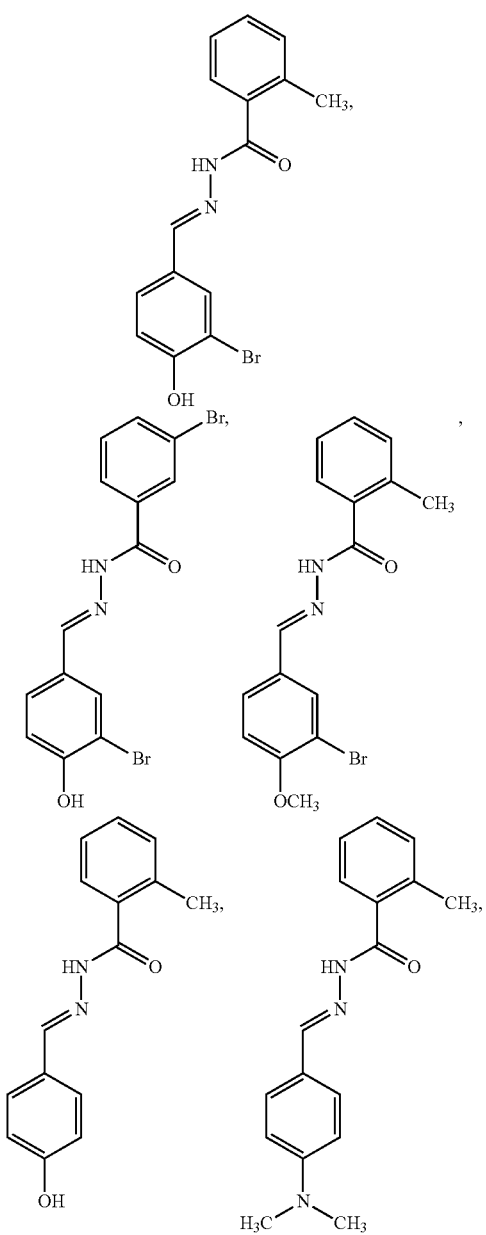

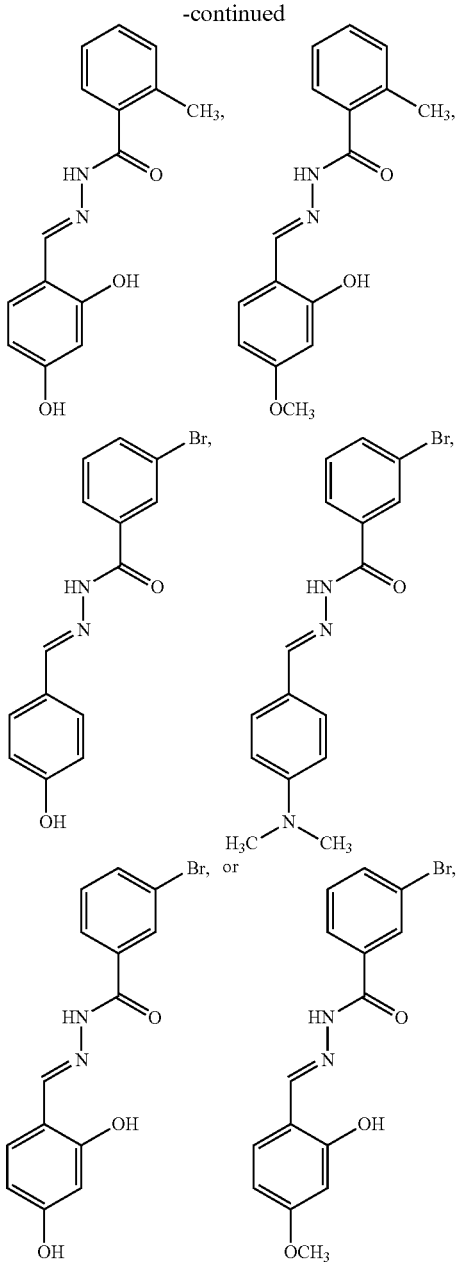

or a pharmaceutically acceptable salt thereof.

In some embodiments, the method further comprising administering an effective amount of an anti-fungal agent.

In some embodiments, the method wherein the amount of the compound and the amount of the anti-fungal agent when taken together is more effective to treat the subject than when the anti-fungal agent is administered alone.

In some embodiments, the method wherein the amount of the compound and the amount of the anti-fungal agent when taken together is effective to reduce a clinical symptom of the fungal infection in the subject.

In some embodiments, the method wherein the anti-fungal agent is fluconazole, amphotericin B, caspofungin, tunicamycin or aureobasidin A.

In some embodiments, the method wherein the fungal infection is caused by *Candida, Aspergillus, Cryptococcus, Histoplasma, Pneumocystis, Stachybotrys* or *Mycrorales* fungus.

In some embodiments, the method wherein the fungal infection is Aspergillosis, Blastomycosis, Candidiasis, Coccidioidomycosis, *Cryptococcus gattii* cryptococcosis, Fungal Keratitis, Dermatophytes, Histoplasmosis, Mucormycosis, Pneumocystis pneumonia (PCP), or Sporotrichosis.

In some embodiments, the method wherein the fungal infection is caused by *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum*, or dimorphic fungi.

In some embodiments, the fungal infection is an internal fungal infection. In some embodiments, the fungal infection is an invasive fungal infection. In some embodiments, the fungal infection is a fungal infection of the skin or lung. In some embodiments, the compound has a fungistatic effect on the fungus. In some embodiments, the compound has a fungicidal effect on the fungus. In some embodiments, the compound is administered orally to the subject. In some embodiments, the compound is administered topically to the subject. In some embodiments, the subject is also afflicted with an immunodeficiency disorder. In some embodiments, the subject is also afflicted with human immunodeficiency virus (HIV).

In some embodiments, the antifungal agent is Amphotericin B, Candicidin, Filipin, Hamycin, Natamycin, Nystatin, Rimocidin, Clotrimazole, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Tolnaftate, or Undecylenic acid. In some embodiments, a pharmaceutical composition comprising a compound of the present invention and an antifungal agent, and at least one pharmaceutically acceptable carrier for use in treating a fungal infection.

In some embodiments, a pharmaceutical composition comprising an amount of the compound of the present invention for use in treating a subject afflicted with a fungal infection as an add-on therapy or in combination with, or simultaneously, contemporaneously or concomitantly with an anti-fungal agent.

In some embodiments of any of the above methods or uses, the subject is a human. In some embodiments of any of the above methods or uses, the compound and/or anti-fungal agent is orally administered to the subject. In some embodiments of any of the above methods or uses, the compound and/or anti-fungal agent is topically administered to the subject.

In some embodiments, the fungus or fungal infection has developed resistance to one or more drugs. For example, a drug resistant fungal infection may have developed drug-resistance to an azole antifungal drug, a polyene antifungal drug and/or an echinocandin antifungal drug.

In some embodiments of any of the above methods or uses, the compound targets APL5, COS111, MKK1, and STE2 in the fungus.

In some embodiments of any of the above methods or uses, the compound targets at least one of APL5, COS111, MKK1, or STE2 in the fungus.

In some embodiments of any of the above methods or uses, the compound disrupts vesicular transport mediate by APL5.

In some embodiments of any of the above methods or uses, the fungus carries non-mutated APL5, COS111, MKK1, and STE2.

In some embodiments of any of the above methods or uses, the fungus carries at least one of non-mutated APL5, COS111, MKK1, and STE2.

As used herein, a "symptom" associated with a fungal infection includes any clinical or laboratory manifestation associated with the fungal infection and is not limited to what the subject can feel or observe.

As used herein, "treating", e.g. of a fungal infection, encompasses inducing prevention, inhibition, regression, or stasis of the disease or a symptom or condition associated with the infection.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley 6 Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl, $C_3$-$C_{12}$ alkenyl, $C_4$-$C_{12}$ alkenyl and so on.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl, $C_3$-$C_{12}$ alkynyl, $C_4$-$C_{12}$ alkynyl and so on "Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to; benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —$CH_2$—($C_5H_4N$), —$CH_2$—$CH_2$—($C_5H_4N$) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references; 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers; Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods
Strains, Media and Reagents

A series of fungal clinical isolates and reference strains were used in this study. This includes *Cryptococcus neoformans, Cryptococcus gattii, Candida albicans, Candida krusei, Candida glabrata, Candida parapsilosis, Candida guilliermondii, Aspergillus fumigatus, Rhizopus oryzae, Blastomyces dermatitis, Histoplasma capsulatum, Coccidioides* spp. *Paecilomyces variotii, Pneumocystis murina*, and, *Pneumocystis jiroveci* (see Table 1 and Table 2). *Escherichia coli* DH5-α and *Pseudomonas aeruginosa* were also used. Yeast Peptone Dextrose (YPD), Yeast Nitrogen Base (YNB), Luria Bertani (LB), Roswell Park Memorial Institute (RPMI) or Dulbecco Modified Eagle Medium (DMEM) were purchased from Invitrogen Life Technologies and used as described. Fluconazole, Amphotericin B, Dexamethasone, Cyclophosphamide, Tunicamycin were purchased from Sigma-Aldrich, St Louis, Mo. Caspofungin and Posaconazole were obtained from Merck, Rahway, N.J. Voriconazole was obtained from Pfizer, Rey Brook, N.Y. N'-(3-bromo-4-hydroxybenzylidene)-2-methylbenzohydrazide (BHBM) and 3-bromo-N'-(3-bromo-4-hydroxybenzylidene) benzohydrazide (1) were obtained from ChemBridge, San Diego, Calif. Cryptococcal capsular antibody mAb 18B7 was a gift from Casadevall's Lab.

Library Screening

The DIVERSet™-CL library was obtained from ChemBridge and contained 10 mM compound(s) per well in 100% DMSO in 96 well plate format. In each well, 10 compounds were mixed together. The compounds were first diluted to 1 mM each (1:10 dilution, 101 DMSO) with yeast nitrogen base (YNB) medium buffered with HEPES at pH 7.4 containing 2% glucose and subsequently diluted to 300 μM (1:3.3 dilution) with the same medium (3% DMSO). Then, 100 μL of this solution was placed into each well of 96 well plates and stored at $-20°$ C. until use. Then, $4\times10^4$ *C. neoformans* cells in 100 μL of YNB medium buffered at pH 7.4 with HEPES were added to each well. Thus, final concentration of the tested drugs was 150 μM in YNB medium containing 1.5% DMSO. The plates were incubated at $37°$ C. in the presence of 5% $CO_2$ for 48 hrs. Optical density at 495 nm was recorded using the Multi-mode microplate reader (FilterMax 5, Molecular Device, Sunnyvale, Calif.) and cocktail compounds in wells showing an OD<80% compared to the OD in the control well (1.5% DMSO but no drug) were selected for further studies. Schematic of the high throughput screening is summarized in FIG. 8.

Synthesis of BHBM Derivatives

The benzaldehyde (1 mmol, 2 ml ethanol) and the benzohydrazide (1 mmol in 2 ml hot ethanol) were combined. All products—except 3 and 7—crystallized within seconds. After 30 minutes at room temperature the product was collected by filtration (Yield: 80 to 95%). Homogeneity of the product was confirmed by thin layer chromatography (TLC) on silicagel $F_{254}$ (Merck KGaA, Darmstadt, Germany) in two different solvent systems benzene/acetic acid 9:1 v/v and hexane/ethylacetate 1:3 v/v. If impurities were present the product was recrystallized from ethanol. For the synthesis of compounds 3 and 7 the reaction was conducted as described above. After 24 h at $4°$ C. the solvent was completely evaporated and the product crystallized from ethylacetate (Yields: 3=72.9%, 7=67.3%). Products were analyzed by TLC as described above.

In Vivo Labeling with Tritiated Palmitate ($^3$H Palmitate)

Labeling fungal cells. *C. neoformans* cells were grown in YNB (pH 7.4) at $37°$ C. in presence of 5% $CO_2$ for 16 hrs. Cells were centrifuged for 10 min at 3,000 rpm at room temperature. Supernatant was removed and the cell pellet was suspended and counted. Next, 900 μL containing $5\times10^8$ *C. neoformans* cells were placed into a 15 ml round bottom Corning centrifuge tube. Then, 100 μL of different concentrations of BHBM or 1 diluted in YNB containing 0.1% DMSO was added resulting in final concentrations of 0.25, 1 and 4 μg/ml, or 0.075, 0.3, 1.2 μg/ml, respectively. Tubes were incubated at in a shaker incubator at 225 rpm at $37°$ C. in the presence of 5% $CO_2$ for 4 hours. Then, 30 μCi/ml of $^3$H palmitate (PerkinElmer, Waltham, Mass.) was added to the culture and incubated for additional 2 hours. Cells without the drug were included as negative control. The cells were then pelleted and washed once with distilled sterile water and suspended in 1.5 ml of Mandala lipid extraction buffer. The lipids were extracted by the methods of Mandala, (Mandala, S. M. et al. 1997) and Bligh and Dyer followed by methanolic based-hydrolysis as previously described (Bligh, E. G. & Dyer, W. J. 1959). The tube was flushed with nitrogen gas and the samples dried in a SPD210 SpeedVac system (ThermoFisher Scientific, Waltham, Mass. The dried lipids were resuspended in 30 μL of 1:1 methanol: chloroform and loaded on thin layered chromatography (TLC) silica gel 60 (EDM Millipore, Billerica, Mass.). Glucosylceramide (GlcCer) standard from soybean (Avanti Polar Lipids, Alabaster, Ala.) was added in a separate lane as control. The sample was resolved in a tank containing a chloroform:methanol:water (65:25:4) as the mobile phase. The TLC plates were then dried, exposed to iodine fume for the identification of the GlcCer standard band, which was marked. The TLC plate was then enhanced by spraying with ENHENCER (PerkinElmer) exposed to X-Ray film at −80° C. for 72 hours and the film was developed.

Labeling Mammalian Cells.

The murine macrophage cell line J774.16 was maintained in Dulbecco Minimum Eagle Medium (DMEM) containing 10% Fetal Bovine Serum (FBS) and 1% Pen-strep by regular seeding. Cell at a density of $5 \times 10^6$ cells/ml of passage 8 were cultured in a 6 well culture plate for 14 hours to achieve adherence. BHBM or 1 at the same concentrations used for fungal cells (see above) were added to the plate for 4 hours. Then, 30 μCi/mL of $^3$H palmitic acid was added and the plate was further incubated for 2 hrs. Labeled J774.16 but untreated cells were included as control. The cells were harvested by the addition of 0.05% trypsin-EDTA and scraping with cell scrapper, and washed once with PBS and dissolved in 2 ml methanol and 1 ml chloroform. Lipids were extracted by the method of Bligh and Dyer followed by base hydrolysis. The samples were flushed with nitrogen and dried in SpeedVac. Dried lipids were suspended in 30 μL of 1:1 methanol:chloroform and loaded on a TLC plate with GlcCer as standard.

In Vitro Susceptibility Testing

Minimal inhibitory concentration (MIC) was determined following the methods of the Clinical Laboratory Standards Institutes (CLSI) with modifications. MIC studies used either RPMI or YNB medium (pH 7.0, 0.2% glucose) buffered with HEPES. HEPES was used instead of MOPS because MOPS totally inhibits the activity of BHBM or of its derivative 1. BHBM or 1 was serially diluted from 32 to 0.03 μg/ml or 19 to 0.02 μg/ml respectively in a 96 well plate with the respective medium. The yeast inoculum was prepared as described in the CLSI protocol M27-A3 guidelines. Plates were incubated at 37° C. and in the presence of 5% $CO_2$ for 24-96 hours (see Table 2). Against all fungal isolates used in the initial susceptibility screen, the MICs were determined as the lowest concentration of the drug that inhibited 50% of growth compared to the control. MIC80 and MIC100, whose drug concentrations inhibited 80% and 100% growth compared to the control respectively, were also determined. For antibacterial activity, E. coli DH5α and P. aeruginosa PA14 were grown overnight in Luria Bertani (LB) broth at 30° C. The cells were washed with PBS and counted. Then, 300 μL from $2 \times 10^8$ cells/mL was spreaded onto LB agar plate using a hockey stick glass spreader. The plate was dried and wells were punched out using a cut tips. Fifty microliters of different drug concentration was added to the well. The plate was then incubated at 30° C. for 24 hours.

In Vitro Testing Against P. murina and P. jiroveci

Cryopreserved and characterized P. carinii isolated from rat lung tissue (Pc 08-4 #45) was distributed into triplicate wells of 48-well plates with a final volume of 500 μL and a final concentration of $5 \times 10^7$ nuclei/ml. Control dilutions were added and incubated at 37° C. At 24, 48, and 72 hours, 10% of the well volume was removed and the ATP content was measured using Perkin Elmer ATP-liteM luciferin-luciferase assay. The luminescence generated by the ATP content of the samples was measured by a spectrophotometer (PolarStar Optima BMG, Ortenberg, Germany). A sample of each group was examined microscopically on the final assay day of the assay to rule out the presence of bacteria contamination.

In Vitro Killing Assay

From an overnight culture, C. neoformans cells were washed in PBS, resuspended in YNB buffered with HEPES at pH 7.4. Cells were counted and $2 \times 10^4$ cells were incubated with either 1, 2 or 4 μg/ml of either BHBM or 1 in a final volume of 10 ml. Tubes were then incubated at 37° C. in the presence of 5% $CO_2$ on a rotary shaker at 200 rpm. At the illustrated time points, aliquots were taken and diluted and 100 μL was plated onto yeast peptone dextrose (YPD) plates. YPD plates were incubated in a 30° C. incubator and, after 72 hours, colony forming units (CFU) were counted and recorded.

Intracellular Effect of BHBM

To assess whether BHBM will be effective against intracellular C. neoformans, we first incubated J774.16 macrophages with C. neoformans cells at a 1:20 ratio in presence of opsonins (complement and antibody mAb 18B7 against the cryptococcal capsular antigen). After 2 hours of incubation, about 60-80% of macrophages have at least one C. neoformans cell internalized. At this time, wells were washed to remove extracellular fungal cells and fresh DMEM medium without serum and without mAb 18B7 but containing different concentrations of BHBM was added. Plates were incubated at 37° C. and 5% $CO_2$. At selected time points, 0, 6, 12 and 24 hours, extracellular cells were collected by washing and plated onto YPD for CFU counting of extracellular cells. Then, macrophages containing C. neofromans were lysed, collected and serial dilutions were plated onto YPD for CFU counting of intracellular fungal cells.

Synergistic Assay

Synergistic activity was assayed by calculating the fractional inhibitory index (FIC) as previously described (Del Poeta, M. et al. 2000). Briefly, in a 96 well plate, drug A (either BHBM or 1) was serially diluted from 16 to 0.015 μg/ml (11 dilutions) whereas drug B (either Fluconazole, Amphotericin B, Caspofungin, or Tunicamycin) was serially diluted from 12 to 0.19 μg/ml, 5 to 0.078 μg/ml, 70 to 1.09 μg/ml, and 6 to 0.09 μg/ml (7 dilutions), respectively. The FIC was defined as: [MIC combined/MIC Drug A alone]+ [MIC combined/MIC Dug B alone].

Resistance Assay

To see whether incubation with the drugs will induce resistance, C. neoformans cells were passaged daily in sub-MIC drug concentrations. Briefly, from an overnight culture, C. neoformans cells were washed with PBS, resuspended in YNB buffered with HEPES at pH 7.4 and counted. Then, $10^6$ cells were incubated with 0.5, 0.25 or 0.125 μg/ml of BHBM or 0.15, 0.075 and 0.037 μg/ml of 1 in 1 ml final volume. Tubes without the drug served as negative control. Tubes with Fluconazole (0.5, 1 and 2 μg/ml) served as positive control. The cells were grown at 37° C. in the presence on 5% $CO_2$ on a rotary shaker at 200 rpm. Every 24 hours, the cells were pelleted by centrifugation, washed with PBS, and resuspended in YNB, and $10^6$ cells were transferred into a fresh drug tube and incubated as above. These daily passages were continued for 15 days. Cell aliquots were collected on day 0 (before any drug exposure), 5, 10, 15, and MIC was determined using the microbroth dilution assay as described above.

Animal Studies for Cryptococcosis

For survival studies, 4-week old CBA/J female mice (Jackson Laboratory, Bar Harbor, Me.) were used. Ten mice per treatment or control group were used. Mice were infected by nasal inoculation of 20 µL containing $5\times10^5$ cells of *C. neoformans* H99 strain. Treated mice received an intraperitoneal injection of 1.2 mg/kg/day of either BHBM or 1 in 100 µL final volume of PBS containing 0.4% DMSO. Untreated mice, received 100 µL of PBS/0.4% DMSO. Mice were feed ad-libitum and monitored closely for sign of discomfort and meningitis. Mice showing abnormal gait, lethargic, tremor, significant loss of body weight or inability to reach water or food were sacrificed and survival counted from that day. At the end of the survival study, tissue burden culture was performed in mice that survived the infection. Mice were sacrificed and their organs were extracted, and homogenized in 10 ml sterile PBS using a homogenizer (Stomacher80, Cole-Parmer, Vernon Hills, Ill.). Organ homogenates were serially diluted 1:10 in PBS and 100 µL was plated on YPD agar plates and incubated at 30° C. for 72 hours for CFU count. For histopathology, extracted organs were fixed in 10% formalin before paraffin sectioning and staining with either Hematoxylin-Eosin or Mucicarmine. Images were taken at 40× in a Zeiss Axio Observer in brightfield mode.

Animal Studies for Pneumocystosis

For survival studies, C3H/HeN mice ordered from the National Cancer Institute (Bethesda, Md.) were used. Mice were infected with *P. murina* pneumonia through exposure to mice with a fulminant *P. murina* infection (seed mice). These mice were immune suppressed by the addition of dexamethasone at 4 mg/liter to the drinking water. Sulfuric acid at 1 ml/liter was also added to the drinking water for disinfection. The seed mice are rotated within the cages for 2 weeks and then removed. After the mice had developed a moderate infection level (approximately 5 weeks), they were divided into a negative control group (control steroid), positive control group (trimethoprim/sulfamethoxazole) and treatment groups (BHBM or 1). Twelve mice were used in each group. BHBM or 1 were administered intraperitoneally or by oral gavage on a mg/kg/day basis for up to 3 weeks. The dose, route, and frequency of administration varied depending on the agent being tested. At the end of the treatment, mice were sacrificed and processed for analysis. Slides were made from the lung homogenates at different dilutions and stained with Diff-Quik to quantify the trophic forms and Cresyl Echt violet to quantify the asci. Additional group of mice were selectively depleted of their CD4+ lymphocytes by antibody treatment with 300 µg of GK 1.5 antibody (Biovest International, Minneapolis, Minn.) administered intraperitoneally 3 times on days 1, 3, and 7. After this initial treatment, the mice were infected by exposure to *P. murina* infected mice. Mice then were treated with 100 µg of GK 1.5 antibody intraperitoneally once a week for 6 weeks. Mice were then treated with 1.25 or 12.5 mg/kg/day of 1 for 14 days while continuing the GK1.5 treatment. Control mice received vehicle.

Animal Studies for Candidiasis

For survival studies, 8-week old CBA/J female mice (Jackson Laboratory) were used. Eight mice per treatment or control group were used. Mice were infected by intravenous inoculation of 100 µL containing $1\times10^5$ cells of *Candida albicans* SC-5314 strain. Treated mice received an intraperitoneal injection of 1.2 mg/kg/day of either BHBM or 1 in 100 µL final volume of PBS containing 0.4% DMSO. Untreated mice, received 100 µL of PBS/0.4% DMSO. Mice were feed ad-libitum and monitored closely for sign of discomfort. At the end of the survival study, tissue burden culture was performed in mice that survived the infection. Mice were sacrificed and their organs were extracted and homogenized in 10 ml sterile PBS using homogenizer. Organ homogenates were diluted 10 times in PBS, and 100 µL was plated on YPD agar plates and incubated at 30° C. for 72 hours for CFU count.

Toxicity

In Vitro.

The murine macrophage cell line J774.16 was maintained in DMEM containing 10% FBS and 1% Pen-strep. At passage #7, $10^5$ cells/well in DMEM containing 10% FBS was transferred into 96 well plates and cultured for 14 hours for the cells to adhere to the wells. BHBM or 1 were added to the cells at concentration ranging from 0.1 to 100 µg/ml. The wells without the drug served as control. The plate were incubated at 37° C. in the presence of 5% $CO_2$. After 12 or 24 hours, the supernatant was removed and 50 µL of 5 mg/ml of 3-(4,5-dimethylthiazol-2-yl)-2,5-diphenyltetrazolium bromide (MTT) solution in PBS was added to each well and plates incubated for 4 additional 4 hours. The formazan crystal formed inside the cell was dissolved by adding 50 µL of isopropanol containing 0.1N HCL. The optical density was measured at 570 nm.

To determine whether BHBM or 1 toxicity was enhanced by corticosteroids, a separate set of J774.16 cells were incubated with 10 or 100 µg/ml of Dexamethasone alone or combined with either 1, 5 and 10 µg/ml of BHBM or with 1, 5, 10 µg/ml of 1. After 24 hours, the MTT assay was performed as described above.

In Vivo.

Mice toxicity studies were performed using 4-week old CBA/J female mice from Jackson Laboratory. Five mice received 1.2 mg/kg/day of BHBM for 60 days. Three control mice received a solvent injection per day. At 60 day, blood was collect in two tubes: one with $K_2$EDTA and the other without $K_2$EDTA to allow blood clotting. The blood clot was then centrifuged at 1500 rpm for 10 min, serum was collected and analyzed for liver and kidney blood tests. The non-coagulated blood was used for hematocrit and blood cells analysis. These tests were done using MASCOT™ HEMAVET 950FS (Drew Scientific Group, Dusseldorf, Germany)

Pharmacokinetics of BHBM

BHBM was dissolved in a mixture of cremophore: ethanol (1:1) to prepare 10 mg/ml stock solution. The stock solution was diluted in PBS to obtain 200 µg/ml and 400 µg/ml solutions for both IV and IP administrations in C3H/HeN mice (n=3). BHBM was administered to control healthy mice or immunocompromised mice infected with *Pneumocystis murina* at doses of 0.8 mg/kg and 1.6 mg/kg via IV tail vain injection or intraperitoneal injection in 100 µL final volume. The mice from each group were sacrificed and blood samples were collected at pre-dose and 0.5, 1, 2, 4, 8, 12, and 24 post-administration into $K_2$EDTA containing tubes. The samples were centrifuged immediately and plasma was collected and stored at −80° C. until analysis. Plasma samples were extracted using methylene chloride. Briefly, 50 µL of the plasma sample was taken into a glass vial and 10 µL of internal standard N'-(3-bromobenzylidene)-4-hydroxybenzohydrazide was added. After mixing, 1 ml of methylene chloride was added and the samples were vortex mixed for 30 seconds followed by centrifugation for 5 minutes. Eight hundred microliters of supernatant was transferred to another test tube and evaporated to dryness using a centrifugal evaporator. The residue was reconstituted in 100 µL acetonitrile: water (50:50) solution, mixed and transferred to mass spec vials. Separation was performed under isocratic reverse phase chromatographic condition using a water's XBridge C18 column (3.5 µm; 2.1×100 mm) (Waters, Milford, Mass.), a Finnigan Surveyor MS pump (ThermoFisher Scientific, Waltham, Mass.), and a Finnigan Micro AS autosampler (ThermoFisher Scientific). The mobile phase consisted of water: acetonitrile with 0.1% formic acid (50:50) ran at a flow rate of 200 µL/min. Aliquots of 5 µL were analyzed using LTQ-FT liquid chromatography/tandem mass spectrometer (LC/MS/MS) with electrospray source in the positive ion mode (ThermoFisher Scientific, Waltham, Mass.). The retention time of BHBM was 5.7 mins. The lower limit of quantification (LLOQ) was 10 ng/ml. Systemic exposure of BHBM in mice was quantified by calculating the AUC of the drug from pre-dose to the end of the dosing interval ($AUC_{0-t}$) using the linear trapezoidal rule by non-compartmental analysis employing Phoenix winNonlin 6.3 (Pharsight Corp, Mountain View, Calif.). The elimination half-life ($t_{1/2}$) was calculated as $0.693/\lambda_z$, where $\lambda_z$ is the terminal elimination rate constant. Bioavailability of IP route was calculated.

Lipid Mass Spectrometry

For lipid analysis by mass spectrometry, fungal cells (*C. neoformans* or *C. albicans*) were grown in YNB and incubated with BHBM or 1 as explained for the in vivo labeling (except that tritiated palmitate was not added), for 6 hrs. Samples without drug were included as control. Before lipid extraction, lipid internal standards (C17 ceramide and C17 sphingosine) were added. Lipids were then extracted following the methods of Mandala and Bligh and Dyer and one fourth of the sample was aliquoted for determination of the inorganic phosphate. The remainder of the sample was subjected to base hydrolysis and then analyzed using LC/MS. Results were normalized with the inorganic phosphate levels.

In Vitro Activity of Gcs1

For the in vitro Gcs1 assay, *C. neoformans* wild-type (WT) or the Δgcs1 cells were grown in YPD broth overnight at 30° C. in a shaker incubator. Cells were washed with sterile water and then lysed by bead beating in presence of glass bead and protease cocktail inhibitor, as described (Liberto, C. et al. 2001). Next, 800 µg of cell lysate was incubated with 0.3 mM C16 ceramide (C16-R—OH) and in the presence or absence of BHBM. The mixture was subjected to 3 cycles of sonication (20 sec) and vortexing (5 sec). Next, 8 µM of radiolabelled UDP-$^{14}$C-Glucose (American Radiolabeled Chemical) was added and, after brief vortexing, the tubes were incubated at 37° C. for 45 min. The reaction was stopped by adding 0.9 ml of 0.45% NaCl solution containing chloroform:methanol 2:1. The organic phase was collected in a glass tube and flushed with nitrogen. The sample was dried and resuspended in chloroform:methanol 1:1. Sample was then loaded on a TLC plate using by chloroform:methanol:water as the mobile phase.

Yeast Library Screening

Variomics Library:

The screening of the *Saccharomyces cerevisiae* genome-wide variomics libraries for potential BHBM resistant clones was performed as described previously (Huang, Z. et al. 2013) but with slight modifications. About 6×10$^7$ haploid cells was plated on solid SC-Ura medium buffered with HEPES at pH 7.0, which contained BHBM at a concentration of 20 µM (~7 µg/ml) and incubated at 30° C. for 3 days.

Hip-Hop Library:

The yeast deletion collection used here comprises of approximately 5900 individually barcoded heterozygous diploid strains (HaploInsufficiency Prolifing) and ~4800 homozygous diploid strains (HOmozygous deletion Profiling) (Pierce, S. E. et al. 2007). Pools of approximately equal strain abundance were generated by robotically pinning (S and P Robotics, Ontario, Canada) each strain (from frozen stocks) onto YPD agar plates as arrays of 384 strains/plate. After two days of growth at 30° C., colonies were collected from plates by flooding with YPD and aliquoted at optical density of 2 (at 600 nm). The fitness of each strain in each experimental pool was assessed as described (Pierce, S. E. et al. 2007). The dose of BHBM that resulted in 15% growth inhibition in BY4733 (the parent strain of the yeast deletion collection) was determined by performing a dose response over the course of 16 h of growth at 30° C. Screens of the homozygous deletion collection were performed for 5 generations of growth in BHBM, and screens of the Heterozygous deletion collection were collected following 20 generations of growth. Cells were processed as described (Proctor, M. et al. 2011). Briefly genomic DNA was extracted from each sample, subjected to PCR to amplify the unique barcode identifiers and the abundance of each barcode was determined by quantifying the microarray signal as described. A ranked list of all genes in the genome was generated for each experiment and then compared using gene set enrichment analysis or GSEA according to Lee (Lee, A Y et al. 2014).

C6-NBD-Ceramide Staining

The Golgi apparatus of *C. neoformans* and *C. albicans* was stained with C6-NBD-ceramide using a previously described protocol (Kmetzsch, L. et al. 2011), based on the property that this fluorescent lipid accumulates at the Golgi of either living or fixed cells (Pagano R. E. et al. 1989). Control or BHBM-treated (4 µg/ml) yeast cells were fixed with 4% paraformaldehyde in PBS. Cell suspensions were then washed with the same buffer and incubated with C6-NBD-ceramide (20 mM) for 16 h at 4° C. The cells were then incubated with bovine serum albumin (BSA, 1%) at 4° C. for 1 h to remove the excess of C6-NBD-ceramide. After washing with PBS, the cells were incubated with 10 µg/ml DAPI (Sigma-Aldrich, St. Louis, USA) for 30 min at room temperature. The cells were washed again with PBS and stained cell suspensions were mounted over glass slides as described above and analyzed under an Axioplan 2 (Zeiss, Germany).

Statistical Analysis

Statistical analysis for survival studies was performed using Student-Newman-Keuls t test for multiple comparisons using INSTAT. Statistical analysis for tissue burden and for trophic form and asci counts was performed using the analysis of variance (ANOVA). Additional statistic was performed using Student t test.

Comparison Studies

For survival studies, 4-week old CBA/J female mice (Jackson Laboratory, Bar Harbor, Me.) were used. Total of forty mice were infected by tail vein injection of 200 µL containing 10$^5$ cells of *C. neoformans* H99 and were randomly separated into 5 groups (8 mice per group). Treatment started within 2 hours of infection. The treated mice received an intraperitoneal injection of 1.2 mg/kg/day of BHBM, 1, amphotericin B or 10 mg/kg/day of fluconazole in 100 µL final volume of PBS containing 0.4% DMSO. Untreated mice, received 100 µL of PBS/0.4% DMSO. Mice were fed ad-libitum and monitored closely for sign of discomfort and meningitis. Mice showing abnormal gait, lethargy, tremor, significant loss of body weight, or inability to reach water or food were sacrificed and survival was counted until that day.

Sample Preparation for Transmission Electron Microscopy (TEM)

Sample preparation for Transmission electron Microscopy (TEM) was performed similar to the methods of Heung (Heung et al. 2005) with minor modifications. Briefly, *C. neoformans* (H99) were grown in YNB (pH=7.4) at 37° C. and 5% $CO_2$ and treated for 6 hours with either BHBM or 1 (4 µg/mL), non-treated cells were also included as control. The cells were pelleted at 3000 rpm (1700 g) and fixed with 2% EM glutaraldehyde in PBS solution for 1 hour. Samples were then washed in PBS, placed in 1% osmium tetroxide in 0.1M PBS, dehydrated in a graded series of ethyl alcohol and embedded in Embed812 resin. Ultrathin sections of 80 nm were cut with a Leica EM UC7 ultramicrotome (Leica Microsystems Inc., Buffalo Grove, Ill.) and placed on uncoated mesh copper grids. Sections were then counterstained with uranyl acetate and lead citrate and viewed with a FBI Tecnai12 BioTwinG2 electron microscope (FBI, Hillsboro, Oreg.) Transmission Electron Microscope (TEM). Digital images were acquired with an AMT XR-60 CCD Digital Camera system.

BHBM Pre-Screen

For the BHBM revertant screen, the drug-sensitive RYO0622 haploid strain was used (Suzuki, Y., et al. 2011). To determine the $IC_{100}$ dose of BHBM (at which yeast cell growth is inhibited at 100% upon drug exposure), 20 ul of RYO0622 cells (at $OD_{600}$ $1^{-4}$) were plated on solid synthetic complete (SC) media alone, with DMSO, or with a range of BHBM doses (0.2, 0.4, 0.8, 1.6 and 3.2 mM) in a 46-well plate. The plate was incubated for 2 days at 30° C. in the dark.

BHBM Revertant Screening Assay

RYO0622 cells were cultured to mid-log phase (~$OD_{600}$ 0.5) in liquid SC media before adjusting the cell density to 1×10* cells/ml (equivalent to $OD_{600}$~0.1). One ml of cells was plated on solid SC media containing DMSO solvent control (0.26% v/v) or BHBM (at 0.4 mM IC100 dose) and incubated at 30° C. in the dark. A lawn of cells grew on the solvent control, while only a single BHMB-resistant colony was identified after 9 days. Longer incubation did not result in the appearance of further resistant clones. To confirm BHBM resistance, single colonies isolated from the BHBM containing SC media were plated onto fresh solid SC medium containing 0.4 mM BHBM and incubated for 2 days at 30° C. in the dark. Robust BHBM-resistant cells were seen.

Yeast Genomic DMA Preparation

Genomic DMA was extracted from RYO0622 and BHBM-resistant cells using the Puregene kit (Qiagen), according to the manufacturer's instructions.

Next-Generation Sequencing of BHHM-Resistant RYO0622

Genomic DMA was quantified using Qubit fluorometry (Life Technologies) and diluted for sequencing library preparation using Nextera XT library preparation kit according to the manufacturer's instructions (Illumina). Libraries were pooled and sequenced on a single MiSeq lane, generating paired-end 150 bp reads.

Mapping & Variant Calling

Raw FASTQ paired-end reads for the parent (RYO0622) and the revertant were independently aligned to NCBI sacCer3 (genbank/genomes/Eukaryotes/fungi/Saccharomyces_cerevisiae/SacCer_Apr2011) reference genome using bwa mem v0.7.4-r385 with the −M flag to mark shorter split hits as secondary for compatibility with Picard (Li, H. & Durbin, R. 2009). Resultant SAM files were converted to BAM format using samtools v1.1 and sorted by coordinate using Picard v1.96 (SortSam) (http://picard.sourceforge.net). PCR duplicate reads were filtered out using Picard MarkDuplicates (10.24% estimated duplication) and indexed using Picard BuildBamIndex. To call single nucleotide variants (SNVs), we ran the GATK Unified Genotyper v2.1-8 (McKenna, A., et al. 2010) with the NCBI sacCer3 reference genome, stand_call_conf-30, and stand_emit-_conf-10 (DePristo, M. A., et al. 2011). The ploidy parameter was set to 1 since the parent and revertant are in haploid state. Since a database of known indels and known SNPs was not available, we did not perform re-alignment around known indels and quality score recalibration.

TEM.

Sample preparation for Transmission electron Microscopy (TEM) was performed similar to the methods of Hueng et al. with minor modifications (Heung, L. J. et al 2005). Briefly, *C. neoformans* (H99) were grown in YNB (pH-7.4) at 37° C. and 5% $CO_2$ and treated for 6 hours with either BHBM or 1 (4 µg/mL), non-treated cells were also included as control. The cells were pelleted at 3000 rpm (1700 g) and fixed with 2% EM glutaraldehyde in PBS solution for 1 hour. Samples were then washed in PBS, placed in 1% osmium tetroxide in 0.1M PBS, dehydrated in a graded series of ethyl alcohol and embedded in Embed812 resin. Ultrathin sections of 80 nm were cut with a Leica EM UC7 ultramicrotome (Leica Microsystems Inc., Buffalo Grove, Ill.) and placed on uncoated mesh copper grids. Sections were then counterstained with uranyl acetate and lead citrate and viewed with a FEI Tecnai12 BioTwinG2 electron microscope (FEI, Hillsboro, Oreg.) Transmission Electron Microscope (TEM). Digital images were acquired with an AMT XR-60 CCD Digital Camera system.

Generation of BHBM-Resistant Strains.

For the generation of BHBM-resistant strains, the drug-sensitive *S. cerevisiae* RYO0622 haploid strain was used (Suzuki, Y. et al. 2011). Prescreening studies were performed to determine the $IC_{100}$ dose of BHBM for this strain (the 100% inhibitory concentration [$IC_{100}$] at which 100% yeast cell growth is inhibited upon drug exposure). For this screening, 20 µl of RYO0622 cells (at an $OD_{600}$ of $10^{-4}$) were plated on solid synthetic complete (SC) medium alone or with DMSO or with various BHBM concentrations (67, 133, 266, 533, and 1,066 µg/ml) in a 48-well plate. The plates were incubated for 2 days at 30° C. in the dark. These studies revealed an $IC_{100}$ dose of 133 µg/ml.

Screening for the BHBM-resistant mutants was performed by growing the RYO0622 cells to mid-log phase ($OD_{600}$ of ~0.5) in liquid SC medium before adjusting the cell density to 1×$10^6$ cells/ml (equivalent to an $OD_{600}$ of ~0.1). One milliliter of cells was plated on solid SC medium containing DMSO solvent control (0.26% [vol/vol]) or BHBM (133 µg/ml $IC_{100}$ dose) and incubated at 30° C. in the dark. A lawn of cells grew on the solvent control, while seven BHMB-resistant colonies were identified after 9 days. Longer incubation did not result in the appearance of further resistant colonies. To confirm BHBM resistance, single colonies isolated from the BHBM-containing SC medium were plated onto fresh solid SC medium containing 133 µg/ml BHBM and incubated for 2 days at 30° C. in the dark. Robust BHBM-resistant cells were seen.

Next-Generation Sequencing of BHBM-Resistant Strains.

Genomic DNA was extracted from RYO0622 and BHBM-resistant cells using a standard yeast DNA extraction protocol (Hoffman, C. S. et al. 1987). Genomic DNA samples were quantified using Qubit fluorometry (Life Technologies) and diluted for sequencing library preparation using a Nextera XT library preparation kit according to the manufacturer's instructions (Illumina, San Diego, Calif.). For the initial round of sequencing, individual sequencing libraries were prepared for the parent and a single BHBM-resistant clone. These libraries were pooled and sequenced on a single MiSeq lane (Illumina), generating paired-end 150-bp reads. Further BHBM-resistant colonies were obtained in a second screen, and their DNAs were pooled at equal concentrations before preparation of a single sequencing library for the pool. This pool was sequenced alongside a new library for the parent strain on a single HiSeq 2500 lane (Illumina), generating paired-end 100-bp reads.

Mapping and Variant Calling.

Raw FASTQ paired-end reads for the parent (RYO0622) and the BHBM-resistant pool were independently aligned to the NCBI sacCer3 reference genome using bwa mem v0.7.4-r385 (Li, R., Yu, C. et al. 2009) with the −M flag to mark shorter split hits as secondary for compatibility with Picard. Resultant SAM files were converted to BAM format using samtools v1.1 and sorted by coordinate using Picard v1.96 (SortSam). PCR duplicate reads were filtered out using Picard MarkDuplicates and indexed using Picard BuildBamIndex. To call single nucleotide variants (SNVs), the GATK Unified Genotyper v2.1-8 (McKenna, A. et al. 2010) was ran with the NCBI sacCer3 reference genome, stand_call_conf=30, and stand_emit_conf=10 (DePristo, M. A. et al. 2011). The ploidy parameter was set at 1, since the parent and resistant strains are in haploid state. Realignment around known indels and quality score recalibration was not performed, since a database of known indels and known single nucleotide polymorphisms (SNPs) is not available.

Validation of BHBM-Resistant Yeast Mutants.

Four yeast genes (ALP5, COS111, MKK1, and STE2) were selected based on the high-quality variant calls present in the BHBM-resistant pool. To confirm BHBM resistance, the individual haploid Δap15, Δcos111, Δmkk1 and Δste2 deletion mutants were assayed for growth fitness after treatment with BHBM. Unrelated drug controls, including methyl methane sulfonate (MMS) (cytotoxic) and fluconazole (antifungal) were assayed in parallel. Strains were cultured to mid-log phase ($OD_{600}$ of ~0.5) in liquid YPD medium before adjusting the cell density to an $OD_{600}$ of 0.0625 with YPD medium. The cells were transferred to 96-well plates containing 100 μl of YPD with DMSO solvent control (2% [vol/vol]), BHBM (6 to 733 μg/ml), MMS (10 μg/ml to 625 μg/ml), or fluconazole (2 to 306 μg/ml) and incubated at 30° C. for 24 h. The fitness of individual strains was measured using a spectrophotometer plate reader (Tecan GENios, Chapel Hill, N.C.) to read $OD_{600}$ over 24 h as a proxy for cell growth. Relative growth inhibition was calculated by the average rate after normalizing the ODeoovalues in drug wells against the DMSO control wells on each assay plate.

Example 1. Screening the ChemBridge DIVERSET-CL Library

Figure 8:
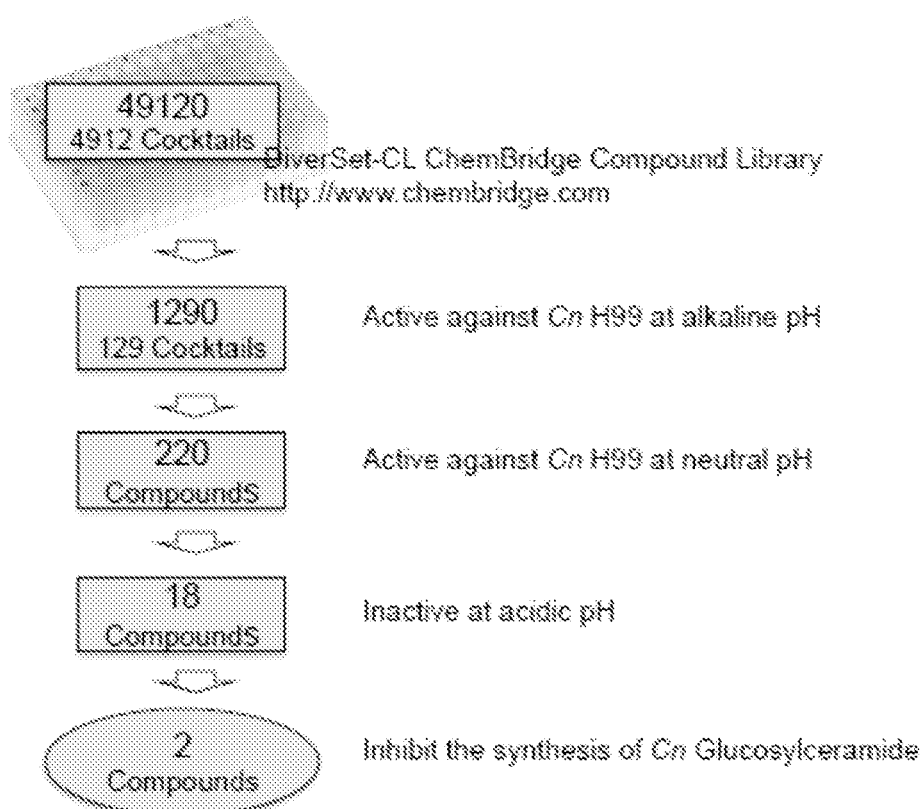
FIG. 8: Schematic of high-throughput screening using the DiverSet-CL ChemBridge Library. Compounds were screened using microtiter plates (96 wells) in which $2 \times 10^4$ *Cryptococcus neoformans* (Cn) H99 strains cells were added to 150 μM individual compound concentration per well in YNB medium with 1.51 DMSO. Compounds were selected for activity if inhibited growth of Cn H99≥80%. Compounds were considered inactive if there was no difference between drug-positive well and drug negative well. Drug-negative well contained $2 \times 10^4$ Cn H99 in YNB medium with 1.5% DMSO.
Figure 9:
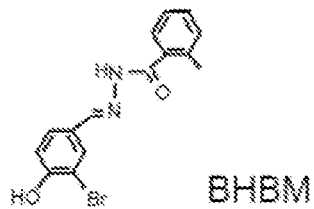
FIG. 9: Structure, solubility and stability of BHBM.

It was previously shown that a *C. neoformans* Δgcs1 mutant lacking GlcCer cannot grow in neutral and alkaline pH at 37° C. and 5% $CO_2$. Thus, 49,120 compounds were screened for those that would inhibit growth of *C. neoformans* under these conditions (FIG. 8). Plates were incubated at 37° C. and 5% $CO_2$ to mimic the environmental conditions found in the host during infection. For the first screening, a total of 4,912 inhibitory assays were performed (10 compounds are mixed in each well in this library). Following this screening, 129 cocktails/wells in which the OD reading was less than 80% of that obtained in the control well were selected. The 1290 compounds were then identified using the ChemBridge database and screened individually using minimum inhibitory concentration (MIC) studies. MIC studies were performed first at alkaline pH (7.4) and then at neutral pH (7.0) and compounds inhibiting the growth of *C. neoformans* at both pH levels were selected. For all compounds, 11 dilutions (from 32 to 0.03 μg/ml) were tested and compounds showing a $MIC_{80} \leq 1$ μg/ml were chosen. Out of 1290, 220 compounds were selected. Next, these compounds were screened at acidic pH (4.0) and 18 compounds that were inactive at this pH (MIC>32 μg/ml) were selected. These 18 compounds were then tested in an in vivo labeling assay for the inhibition of GlcCer synthesis. Two compounds (ID #5271226 and #5285729, ChemBridge Online Chemical Store, San Diego, Calif., USA) were found to significantly inhibit the synthesis of GlcCer in *C. neoformans* cells but not in mammalian (J774) cells (FIG. 1A). Compound #5271226 was identified as N'-(3-bromo-4-hydroxybenzylidene)-2-methylbenzohydrazide (BHBM) and compound #5285729 was identified as 3-bromo-N'-(3-bromo-4-hydroxybenzylidene) benzohydrazide (1). (FIG. 1B and FIGS. 8 and 9). Both compounds were fungicidal—MFC values were 4 μg/ml for BHBM and 1.2 μg/ml for 1 (FIG. 1B).

Example 2. In Vitro Antifungal Activity of BHBM

Figure 12:
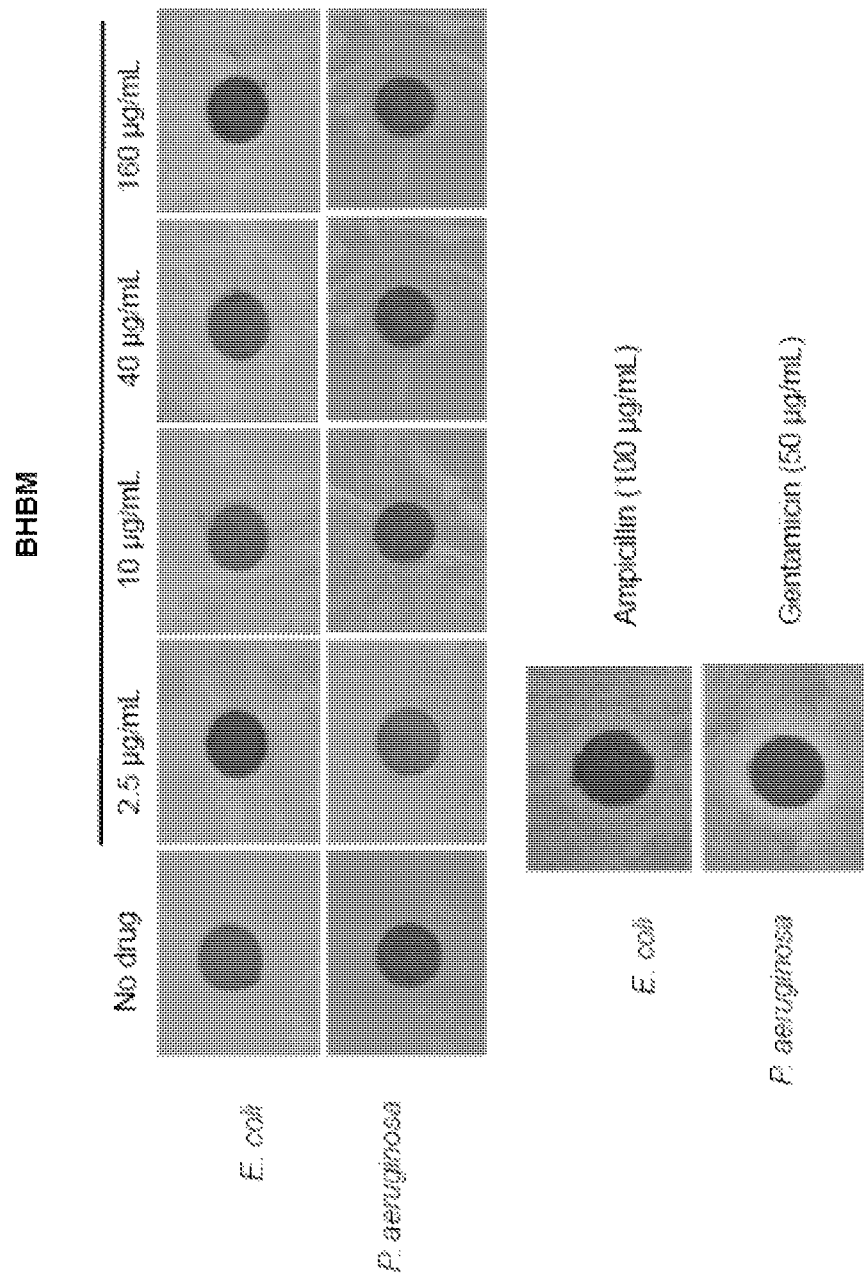
FIG. 12: BHBM has no effect on bacterial cell. *E. Coli* or *P. aeruginosa* ($6 \times 10^7$ cells) were spread onto a LB agar plate. Several wells were punched out using a 1 ml cut-pipet tip and either BHBM, ampicillin or gentamicin at the illustrated concentration was added to the well and the plate was incubated at 30° C. for 24 hr. No zone of inhibition could be seen up to 160 μg/mL BHBM on *E. coli* as well as *P. aeruginosa*. Ampicillin and Gentamicin were used as positive controls.
Figure 13:
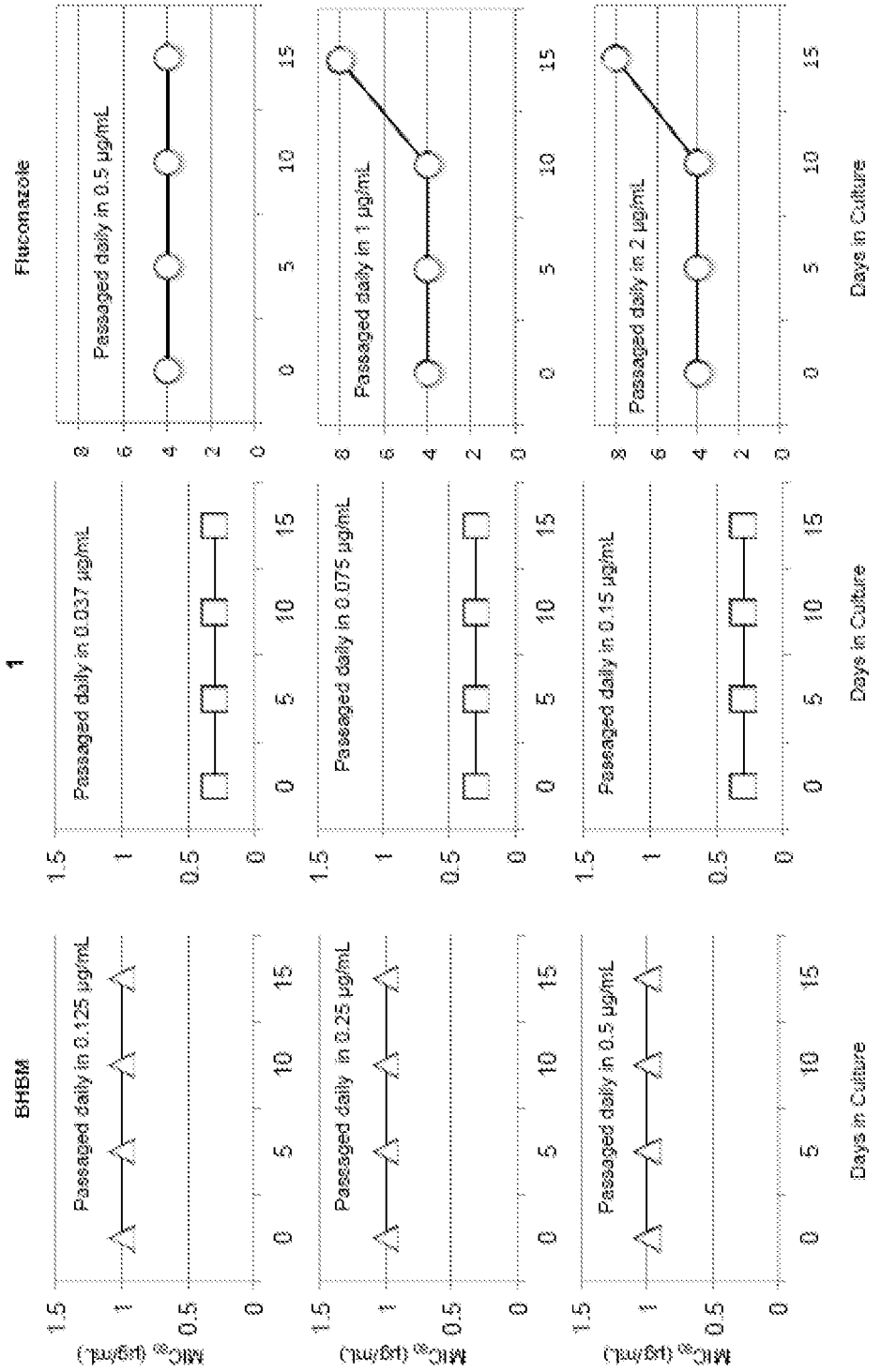
FIG. 13: BHBM and 1 do not induce drug resistance in vivo. Cn cells were passaged daily in either BHBM or 1 at the illustrated concentrations (below $MIC_{80}$) for 15 days. At 0, 5, 10, and 15 days, cells were tested for $MIC_{80}$. Fluconazole was used as positive control.

BHBM was tested against a variety of clinically relevant fungi such as *C. neoformans*, *Cryptococcus gattii*, *Candida albicans*, *Candida krusei*, *Candida glabrata*, *Candida parapsilosis*, *Candida guilliermondii*, *Aspergillus fumigatus*, *Rhizopus oryzae*, *Blastomyces dermatitis*, *Histoplasma capsulatum*, *Coccidioides* spp., *Paecilomyces variotii*, *Pneumocystis murina* and *Pneumocystis jiroveci*. The results are illustrated in Table 1 and in the Table 2. Fluconazole resistant clinical isolates were also included. BHBM showed good in vitro activity against *C. neoformans*, *C. gattii*, *R. oryzae*, *B. dermatitis*, and *H. capsulatum* (Table 1). The compound was moderately active against *C. krusei*, *C. glabrata*, *C. guilliermondii*, *A. fumigatus* and *Coccidioides* spp. (MIC=8-16 μg/ml) and, in general, not active against *C. albicans*, *C. parapsilosis* and *P. variotii*. All Fluconazole-resistant *C. neoformans* strains were sensitive to BHBM. BHBM showed high activity against *P. murina* and very marked activity against *P. jiroveci* (Table 1). Both compounds were also highly synergistic when combined with Fluconazole (FIC indices 0.38 and 0.47 for BHBM and 1 respectively), and Amphotericin B (FIC indices 0.75 and 0.77 for BHBM and 1 #respectively) and additive when combined with caspofungin (FIC index 1 for both BHBM and 1) (FIG. 11). BHBM was synergistic and 1 was additive when combined with Tunicamycin. Neither of the drugs were active against bacteria (MIC>160 μg/ml) (FIG. 12). Next, it was tested whether resistance to these compounds can be developed by incubating *C. neoformans* cells to drug concentrations below the MIC. The results illustrated in FIG. 13 clearly show that, as compared to fluconazole, *C. neoformans* cells do not develop resistance to either BHBM or 1 after 15 days of passages.

TABLE 1

In vitro antifungal activities of N'-(3-bromo-4-hydroxybenzylidene)-2-methylbenzohydrazide (BHBM) determined by the minimum inhibitory concentration (MIC) against several fungal clinical isolates and reference strains, and by the percentage inhibition of ATP (IC$_{50}$) against *Pneumocystis murina/Pneumocystis jiroveci*.

| Species/strain (n) | MIC range (µg/mL) | Species/strain (n) | MIC range (µg/mL) |
|---|---|---|---|
| *Cryptococcus neoformans* (13)[&] | 0.25-8 | *Candida glabrata* (3)[#] | 4->32 |
| *Cryptococcus neoformans* (8)[#S] | 0.5-2 | *Candida parapsilosis* (3)[#] | >32 |
| *Cryptococcus neoformans* (4)[#R] | 1-2 | *Candida parapsilosis* QC[&] | >16 |
| *Cryptococcus gattii* (10)[&] | 0.5-2 | *Candida guilliermondii* (3)[&] | 2->16 |
| *Cryptococcus gattii* (3)[#] | 0.5-1 | *Aspergillus fumigatus* (1)[#] | 8 |
| *Candida albicans* (3)[&] | >32 | *Aspergillus fumigatus* (3)[&] | >16 |
| *Candida albicans* (5)[#] | >32 | *Rhizopus oryzae* (3)[&] | 2 |
| *Candida krusei* (1)[#] | 32 | *Blastomyces dermatitis* (10)[&] | 0.5-1 |
| *Candida krusei* ATCC 6258[#] | 16 | *Histoplasma capsulatum* (10)[&] | 0.125-1 |
| *Candida krusei* QC[&] | 8 | *Coccidioides* spp (10)[&] | 8-16 |
| *Candida glabrata* (10)[&] | 0.125-2 | *Paecilomyces variotii* QC[&] | >16 |

| Agent | Day 1 | Day 2 | Day 3 | Day 4 |
|---|---|---|---|---|
| Pentamidine 1 µg/mL | 78.21/45.70 | 80.30/86.47 | 74.07/84.21 | 27.79/81.44 |
| BHBM 100 µg/mL | 96.98/98.86 | 98.90/98.63 | 99.42/98.08 | 91.47/98.91 |
| BHBM 10 µg/mL | 88.22/96.96 | 94.59/97.76 | 93.57/94.78 | 66.73/90.14 |
| BHBM 1 µg/mL | 66.16/51.48 | 87.58/92.63 | 74.57/87.81 | 44.53/76.96 |
| BHBM 0.1 µg/mL | 6.64/16.15 | 76.03/26.22 | 63.84/39.09 | 16.55/46.25 |
| BHBM IC$_{50}$, *P. murina*^ | 1.02 µg/mL | <0.01 µg/mL | <0.01 µg/mL | 2.02 µg/mL |
| BHBM IC$_{50}$, *P. jiroveci*$ | 0.912 µg/mL | 0.159 µg/mL | 0.074 µg/mL | 0.072 µg/mL |

MIC, minimum inhibitory concentration; IC, inhibitory concentration;
[&]Fungus Testing Lab strains (see Supplementary Table 1);
[#]MDP Lab strains (see Supplementary Table 1);
[S]clinical isolates sensitive to fluconazole;
[R]clinical isolates resistant to fluconazole;
QC, quality control.
^Considered to be "highly active" (IC$_{50}$ <0.010 µg/mL);
$Considered to have "very marked" activity (IC$_{50}$ 0.011-0.099 µg/mL).

TABLE 2

In vitro antifungal activity of BHBM.

| Strain | FTL # | BHBM 24 Hr 50% | BHBM 48 Hr 50% | BHBM 72 Hr 50% | BHBM 96 Hr 50% |
|---|---|---|---|---|---|
| *Candida parapsilosis* | QC | >16 | >16 | | |
| *Candia krusei* | QC | 4 | 8 | | |
| *Paecilomyces variotii* | QC | 8 | >16 | | |
| *Candida glabrata* | 12-3316 | 0.25 | 0.5 | | |
| *Candida glabrata* | 12-3359 | 0.125 | 0.25 | | |
| *Candida glabrata* | 12-3368 | 0.25 | 0.5 | | |
| *Candida glabrata* | 12-3395 | 2 | 2 | | |
| *Candida glabrata* | 12-3396 | 0.5 | 0.5 | | |
| *Candida glabrata* | 12-3431 | 0.125 | 0.125 | | |
| *Candida glabrata* | 12-3446 | 0.25 | 0.5 | | |
| *Candida glabrata* | 12-3469 | 0.5 | 0.5 | | |
| *Candida glabrata* | 12-3474 | 0.25 | 0.25 | | |
| *Candida glabrata* | 12-3490 | 0.25 | 0.5 | | |
| *Candida parapsilosis* | 12-3414 | >16 | >16 | | |
| *Candida parapsilosis* | 12-3434 | >16 | >16 | | |
| *Candida parapsilosis* | 12-3470 | >16 | >16 | | |
| *Candida guiffiermondii* | 12-3273 | >16 | >16 | | |
| *Candida guilliermondii* | 12-1952 | 2 | 2 | | |
| *Candida guiffiermondii* | 12-2800 | >16 | >16 | | |
| *Cryptococcus neoformans* | 12-1355 | | | 1 | |
| *Cryptococcus neoformans* | 12-1585 | | | 1 | |
| *Cryptococcus neoformans* | 12-1625 | | | 2 | |
| *Cryptococcus neoformans* | 12-3177 | | | 4 | |
| *Cryptococcus neoformans* | 12-3271 | | | 1 | |
| *Cryptococcus neoformans* | 12-2444 | | | 1 | |
| *Cryptococcus neoformans* | 12-2730 | | | 0.5 | |
| *Cryptococcus neoformans* | 12-2731 | | | 8 | |
| *Cryptococcus neoformans* | 12-2901 | | | 1 | |
| *Cryptococcus neoformans* | 12-2972 | | | 0.25 | |
| *Cryptococcus neoformans* | 12-3021 | | | 4 | |
| *Cryptococcus neoformans* | 12-3043 | | | 2 | |
| *Cryptococcus neoformans* | 12-2418 | | | 8 | |
| *Cryptococcus gattii* | 11-1264 | | | 0.5 | |
| *Cryptococcus gattii* | 11-1942 | | | 1 | |
| *Cryptococcus gattii* | 11-3112 | | | 1 | |
| *Cryptococcus gattii* | 11-3515 | | | 1 | |
| *Cryptococcus gattii* | 12-429 | | | 1 | |
| *Cryptococcus gattii* | 12-1818 | | | 1 | |
| *Cryptococcus gattii* | 12-1858 | | | 2 | |
| *Cryptococcus gattii* | 12-2475 | | | 1 | |
| *Cryptococcus gattii* | 12-2501 | | | 0.5 | |
| *Cryptococcus gattii* | 12-2674 | | | 1 | |
| *Blastomyces dermatitidis* | 12-1188 | | | | 1 |
| *Blastomyces dermatitidis* | 12-1215 | | | | 1 |
| *Blastomyces dermatitidis* | 12-2304 | | | | 0.5 |
| *Blastomyces dermatitidis* | 12-2530 | | | | 0.5 |
| *Blastomyces dermatitidis* | 12-2661 | | | | 1 |
| *Blastomyces dermatitidis* | 12-2689 | | | | 1 |
| *Blastomyces dermatitidis* | 12-3209 | | | | 0.5 |
| *Blastomyces dermatitidis* | 12-3215 | | | | 0.5 |
| *Blastomyces dermatitidis* | 12-3264 | | | | 1 |
| *Blastomyces dermatitidis* | 12-3454 | | | | 1 |
| *Histoplasma capsulatum* | 12-2629 | | | | 0.25 |
| *Histoplasma capsulatum* | 12-2806 | | | | 1 |
| *Histoplasma capsulatum* | 12-2938 | | | | 0.5 |
| *Histoplasma capsulatum* | 12-2964 | | | | 1 |
| *Histoplasma capsulatum* | 12-3096 | | | | 1 |
| *Histoplasma capsulatum* | 12-3142 | | | | 1 |

TABLE 2-continued

In vitro antifungal activity of BHBM.

| Strain | FTL # | BHBM 24 Hr 50% | BHBM 48 Hr 50% | BHBM 72 Hr 50% | BHBM 96 Hr 50% |
|---|---|---|---|---|---|
| Histoplasma capsulatum | 12-3153 | | | | 0.125 |
| Histoplasma capsulatum | 12-3159 | | | | 0.25 |
| Histoplasma capsulatum | 12-3199 | | | | 0.5 |
| Histoplasma capsulatum | 12-3553 | | | | 1 |
| Coccidioides sp. | 12-3211 | | 8 | | |
| Coccidioides sp. | 12-3216 | | 8 | | |
| Coccidioides sp. | 12-3267 | | 16 | | |
| Coccidioides sp. | 12-3337 | | 16 | | |
| Coccidioides sp. | 12-3364 | | 16 | | |
| Coccidioides sp. | 12-3372 | | 16 | | |
| Coccidioides sp. | 12-3427 | | 16 | | |
| Coccidioides sp. | 12-3453 | | 16 | | |
| Coccidioides sp. | 12-3519 | | 16 | | |
| Coccidioides sp. | 12-3521 | | 16 | | |
| Candida parapsilosis | QC | >16 | >16 | | |
| Candia krusei | QC | 4 | 8 | | |
| Paecilomyces variotii | QC | 8 | >16 | | |
| Candida glabrata | 12-3316 | 4 | 4 | | |
| Candida glabrata | 12-3359 | 4 | 4 | | |
| Candida glabrata | 12-3368 | 2 | 4 | | |
| Candida glabrata | 12-3395 | 2 | 4 | | |
| Candida glabrata | 12-3396 | 2 | 4 | | |
| Candida glabrata | 12-3431 | 0.5 | 1 | | |
| Candida glabrata | 12-3446 | 2 | 2 | | |
| Candida glabrata | 12-3469 | 2 | 2 | | |
| Candida glabrata | 12-3474 | 2 | 2 | | |
| Candida glabrata | 12-3490 | 2 | 2 | | |
| Candida parapsilosis | 12-3414 | >16 | >16 | | |
| Candida parapsilosis | 12-3434 | >16 | >16 | | |
| Candida parapsilosis | 12-3470 | >16 | >16 | | |
| Candida guiffiermondii | 12-3273 | >16 | >16 | | |
| Candida guiffiermondii | 12-1952 | >16 | >16 | | |
| Candida guiffiermondii | 12-2800 | >16 | >16 | | |
| Cryptococcus neoformans | 12-1355 | | | 16 | |
| Cryptococcus neoformans | 12-1585 | | | 8 | |
| Cryptococcus neoformans | 12-1625 | | | 8 | |
| Cryptococcus neoformans | 12-3177 | | | >16 | |
| Cryptococcus neoformans | 12-3271 | | | 8 | |
| Cryptococcus neoformans | 12-2444 | | | >16 | |
| Cryptococcus neoformans | 12-2730 | | | >16 | |
| Cryptococcus neoformans | 12-2731 | | | >16 | |
| Cryptococcus neoformans | 12-2901 | | | >16 | |
| Cryptococcus neoformans | 12-2972 | | | >16 | |
| Cryptococcus neoformans | 12-3021 | | | >16 | |
| Cryptococcus neoformans | 12-3043 | | | >16 | |
| Cryptococcus neoformans | 12-2418 | | | >16 | |
| Cryptococcus gattii | 11-1264 | | | 16 | |
| Cryptococcus gattii | 11-1942 | | | >16 | |
| Cryptococcus gattii | 11-3112 | | | >16 | |
| Cryptococcus gattii | 11-3515 | | | 8 | |
| Cryptococcus gattii | 12-429 | | | 8 | |
| Cryptococcus gattii | 12-1818 | | | 8 | |
| Cryptococcus gattii | 12-1858 | | | >16 | |
| Cryptococcus gattii | 12-2475 | | | >16 | |
| Cryptococcus gattii | 12-2501 | | | >16 | |
| Cryptococcus gattii | 12-2674 | | | >16 | |
| Blastomyces dermatitidis | 12-1188 | | | | 1 |
| Blastomyces dermatitidis | 12-1215 | | | | 1 |
| Blastomyces dermatitidis | 12-2304 | | | | 1 |
| Blastomyces dermatitidis | 12-2530 | | | | 1 |
| Blastomyces dermatitidis | 12-2661 | | | | 2 |
| Blastomyces dermatitidis | 12-2689 | | | | 1 |
| Blastomyces dermatitidis | 12-3209 | | | | 1 |
| Blastomyces dermatitidis | 12-3215 | | | | 1 |
| Blastomyces dermatitidis | 12-3264 | | | | 1 |
| Blastomyces dermatitidis | 12-3454 | | | | 2 |
| Histoplasma capsulatum | 12-2629 | | | | 0.5 |
| Histoplasma capsulatum | 12-2806 | | | | 2 |
| Histoplasma capsulatum | 12-2938 | | | | 1 |
| Histoplasma capsulatum | 12-2964 | | | | 2 |
| Histoplasma capsulatum | 12-3096 | | | | 2 |
| Histoplasma capsulatum | 12-3142 | | | | 2 |
| Histoplasma capsulatum | 12-3153 | | | | 0.25 |
| Histoplasma capsulatum | 12-3159 | | | | 0.5 |
| Histoplasma capsulatum | 12-3199 | | | | 1 |
| Histoplasma capsulatum | 12-3553 | | | | 4 |
| Coccidioides sp. | 12-3211 | | 16 | | |
| Coccidioides sp. | 12-3216 | | 8 | | |
| Coccidioides sp. | 12-3267 | | >16 | | |
| Coccidioides sp. | 12-3337 | | 16 | | |
| Coccidioides sp. | 12-3364 | | 16 | | |
| Coccidioides sp. | 12-3372 | | 16 | | |
| Coccidioides sp. | 12-3427 | | 16 | | |
| Coccidioides sp. | 12-3453 | | 16 | | |
| Coccidioides sp. | 12-3519 | | 16 | | |
| Coccidioides sp. | 12-3521 | | 16 | | |

Example 3. BHBM and 1 have Lethal Activity Against *C. neoformans*

Figure 10:
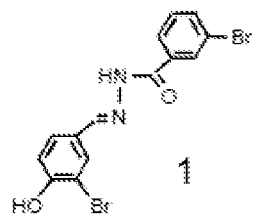
FIG. 10: Structure, solubility and stability of 1.

Since both compounds were fungicidal, their killing activity was examined using a well-established time-kill assay. BHBM showed a concentration-dependent killing (FIG. 2A) whereas 1 showed a time-dependent killing (FIG. 2B). Compound 1 is clearly more effective in killing *C. neoformans* (100% dead cells within 24 hours) and, interestingly, the killing activity does not occur earlier than 24 hours with higher doses (FIG. 2B). BHBM is slower than 1 in killing *C. neoformans* cells and requires at least 72 hours of incubation to kill about 50% of the cells (FIG. 2A). Both compounds are very stable and still retain antifungal activity after 1 year of storage at −20° C. BHBM and 1 require 30% and 50% DMSO respectively at 1 mg/ml concentration, suggesting that their solubility is acceptable but not ideal (FIGS. 9 and 10).

Next, it was tested whether BHBM could kills *C. neoformans* cells when localized intracellularly, as this fungus is considered a facultative intracellular pathogen and, upon phagocytosis, it is able to replicate within macrophages and other phagocytic cells, especially when the host immunity is compromised. To assess the effect of BHBM on intracellular cells, macrophages were first allowed to internalize the fungus, then any remaining extracellular cells were washed out and BHBM was added in absence of opsonins (e.g. complement or antibody). Eventually, intracellular fungal cells will "escape" the macrophages either through macrophage lysis or direct extrusion (Ma, H. et al. 2006; Alvarez, M. & Casadevall, A. 2006) but, due to the lack of opsonins in the medium, these fungal cells cannot re-enter the macrophages. BHBM was found to significantly decrease the intracellular replication of *C. neoformans* cells in a dose-dependent manner, particularly after 12 and 24 hours of incubation (FIG. 2C). These results suggest that, in addition to killing extracellular cells, BHBM also decreases the intracellular replication of *C. neoformans*.

Example 4. BHBM and 1 have Potent Antifungal Activity Against Cryptococcosis

Figure 3C:
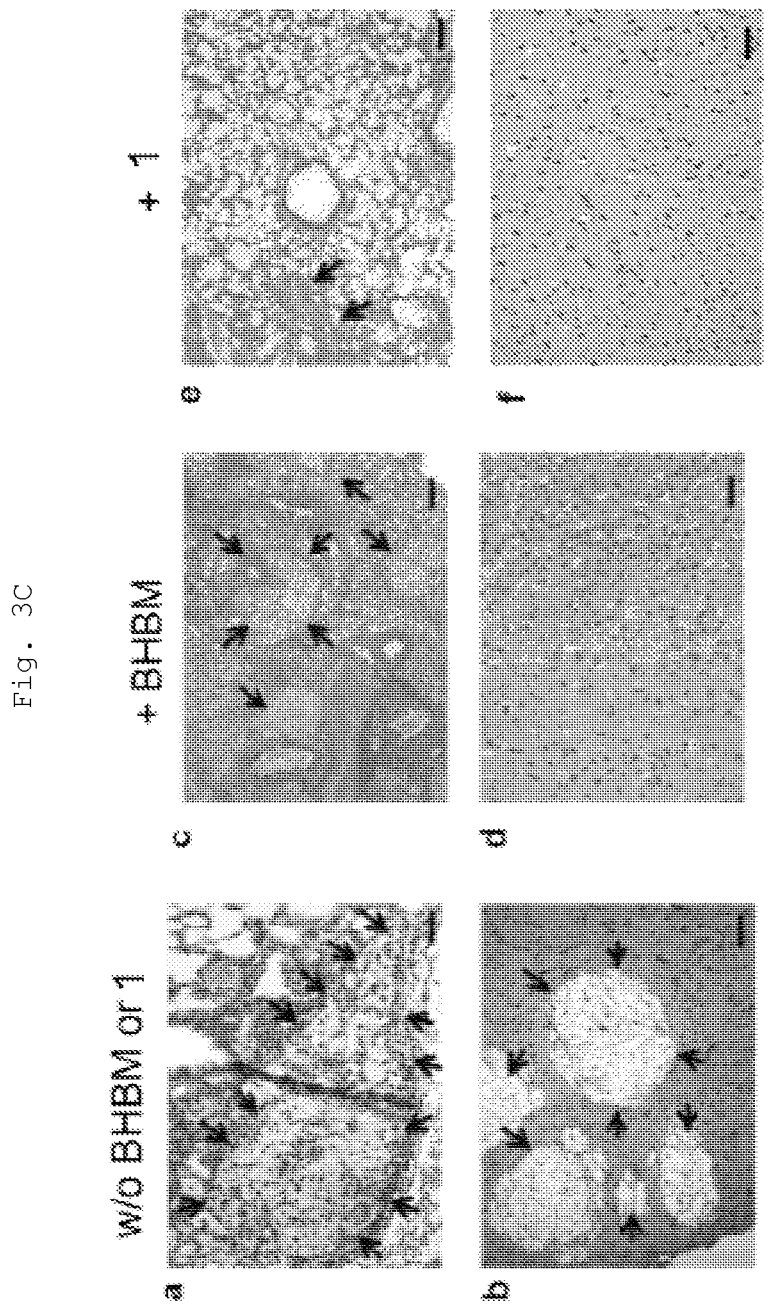
FIG. 3C: Histopathology by H&E staining of lungs and brains of untreated mice (w/o BHBM or 1) at day 25 and treated mice (+BHBM or +1) at day 60 of infection. Lungs and brain tissue of untreated mice showed extensive cryptococcal infiltration (arrows in (a) and (b), respectively). Lungs of mice treated with BHBM (c) or 1 (e) show foci of Cn cells limited to few regions of the lung whereas no fungal cells were observed in brains treated with either BHBM (d) or 1 (f). Scale bar: 150 μm. Panels (a), (c) and (e)=lung. Panels (b), (d) and (f)=brain.

A mice survival study was performed to test the efficacy of BHBM and 1 against cryptococcosis. Five experimental groups of mice were included: mice infected and treated with vehicle (negative control); mice infected and treated with BHBM or with 1; mice uninfected and treated with BHBM or with 1. Treatment was 1.2 mg/Kg/day for BHBM or 1 and was initiated the same day mice were infected with $5\times10^5$ C. neoformans cells intranasally, and continued thereafter. As illustrated in FIG. 3A, 90% of the mice treated with BHBM and 70% of the mice treated with 1 survived C. neoformans infection up to 60 days whereas 100% of untreated mice died within 33 days. At 60 days of infection, the mice that survived (9 for BHBM and 7 for 1) were sacrificed and analyzed for tissue burden (FIG. 3B) and histopathology (FIG. 3C). No C. neoformans cells were found in brains, suggesting that the BHBM and 1 treatment either prevented the dissemination to or/and cleared C. neoformans cells from the brain. Interestingly, BHBM, and more significantly 1, were able to decrease the fungal burden in the lung compared to control mice (infected and untreated) (FIG. 3B). These results are comparable with those obtained upon the infection caused by the mutant lacking GlcCer (Δgcs1), in which no C. neoformans cell were recovered from the brain and a low number of C. neoformans cells were recovered from the lung. This suggests that BHBM and 1 decrease virulence of C. neoformans cells by decreasing GlcCer synthesis in C. neoformans cells during the infection.

Histology analysis of the lungs of the mice infected with C. neoformans and not treated showed spreading of the fungal cells throughout the organ (FIG. 3Ca). These mice also exhibited altered architectural organization in their brain (FIG. 3Cb). In contrast, the lungs of the mice treated with either BHBM or 1 showed a granulomatous response limited in few areas of the lung (FIG. 3Cc and 3Ce). Brain histology of BHBM or 1 treated mice showed no fungal cells and normal structure (FIGS. 3Cd and 3Cf, respectively).

Example 5. In Vivo Toxicity

The uninfected mice treated daily with BHBM or 1 for 60 days were also followed. They appeared normal, maintained a normal weight, and showed a normal physical activity and behavior throughout the observation period. After 60 days, they were sacrificed, and blood work was performed in 5 mice and histology of lungs, brains, kidney, spleen and liver in the remaining 5 mice. Three aged matched control mice (untreated and uninfected) were included for blood work (FIGS. 14, 15 and 16) and histology analysis. Blood work showed a slight increase of liver Aspartate aminotransferase (AST) (125±75 U/L) in BHBM treated mice compared untrated/healthy mice (50±9 U/L) (FIG. 14) and this was the only parameter that was altered. Similar results were obtained with 1. Liver AST was the only parameter that was altered by the drug and all other blood parameters for liver and kidney function were normal, as were the number of erythrocytes, thrombocytes, and leucocytes (FIGS. 15 and 16). In addition, the histological analysis of the organs examined revealed no difference between the BHBM treated and untreated and uninfected mice.

Example 6. BHBM and 1 have Antifungal Activity Against Pneumocystosis

Since BHBM showed in vitro activity against P. murina and P. jiroveci (Table 1), its in vivo activity was tested using a well-established mouse model for pneumocystosis. Four experimental groups of mice were included: mice infected and treated with vehicle (negative control); mice infected and treated with trimethroprim/sulfamethaxozole (T/S); and mice infected and treated with either 0.8 or 1.6 mg/Kg/twice a day of BHBM. A set of mice was followed for survival (FIG. 4A) and a set of mice was used for the microscopic enumeration of asci (FIG. 4B) and nuclei (FIG. 4C) in the lungs. A significant difference was observed between the survival of the BHBM high dose and BHBM low dose treatment groups. Interestingly, the low dose mice showed improved survival over the high dose mice. There was also an Improvement in survival of the low dose mice over the vehicle treated negative controls; however, the difference was not significant. No significant differences were seen in the number of asci or nuclei in lung homogenates of the vehicle treated negative control versus either of the BHBM treatment groups. There was a significant reduction in both asci and nuclei count following 13 days of T/S treatment versus the negative control and BHBM groups.

A different set of mice was used to test the efficacy of 1 in this model. Two drug doses were tested for survival (1.25 and 12.5 mg/kg/day) and 3 drug doses for tissue burden (0.6, 1.25 and 12.5 mg/Kg/day). Mice survival results are illustrated in FIG. 4D and lung asci and nuclei counts are shown in FIG. 4E and FIG. 4F, respectively. Treatment of P. murina infected mice with 1 did not increase survival in our mouse model of P. murina infection compared to control steroid negative controls after 14 days.

However, asci and troph burdens in P. murina infected mice treated with both 1.25 mg/kg/day and 12.5 mg/kg/day of 1 for 14 days were significantly reduced compared to the vehicle treated negative control group (FIGS. 4D and 4F). These data suggest that 1 may have a dose dependent effect in inhibiting growth of P. murina in the lung. Although not statistically significant, 1 appears to display some toxicity in this mouse model immunosuppressed with corticosteroids.

Example 7. In Vitro Toxicity of BHBM and 1

Figure 17:
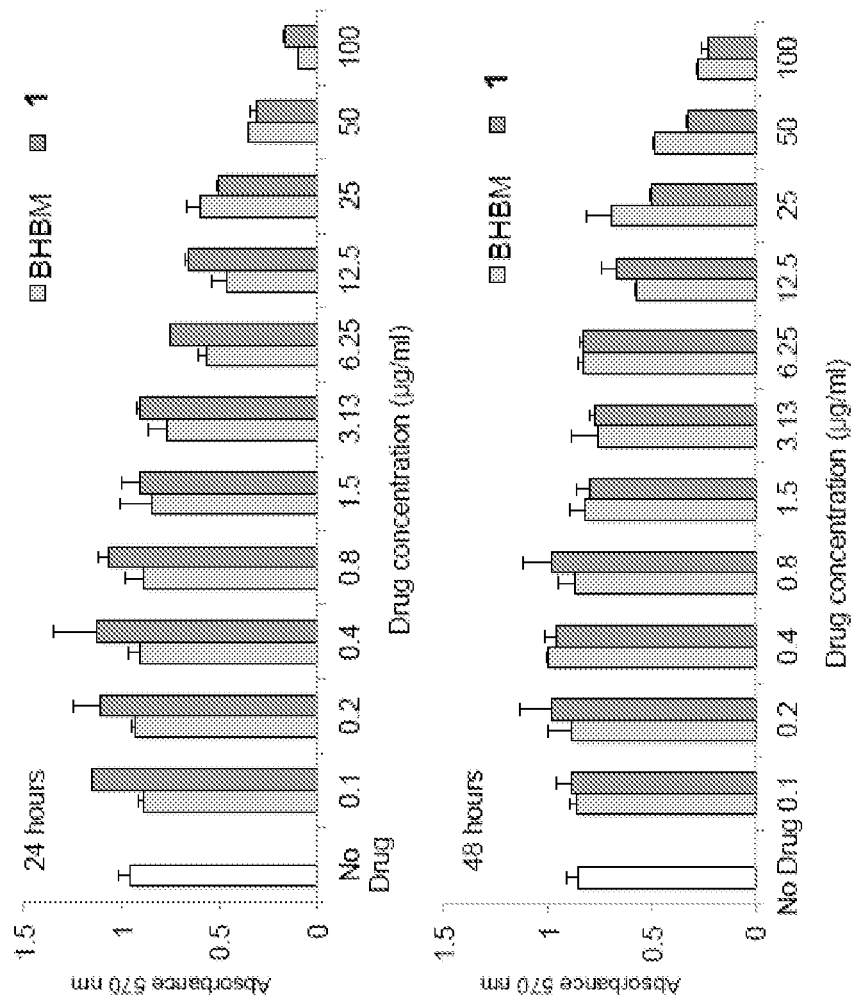
FIG. 17: In vitro toxicity studies at 24 and 48 hr after exposure to BHBM or 1 using dimethylthiazol-diphenyl tetrazolium bromide (MTT) assay in J774 mammalian cells.
Figure 18:
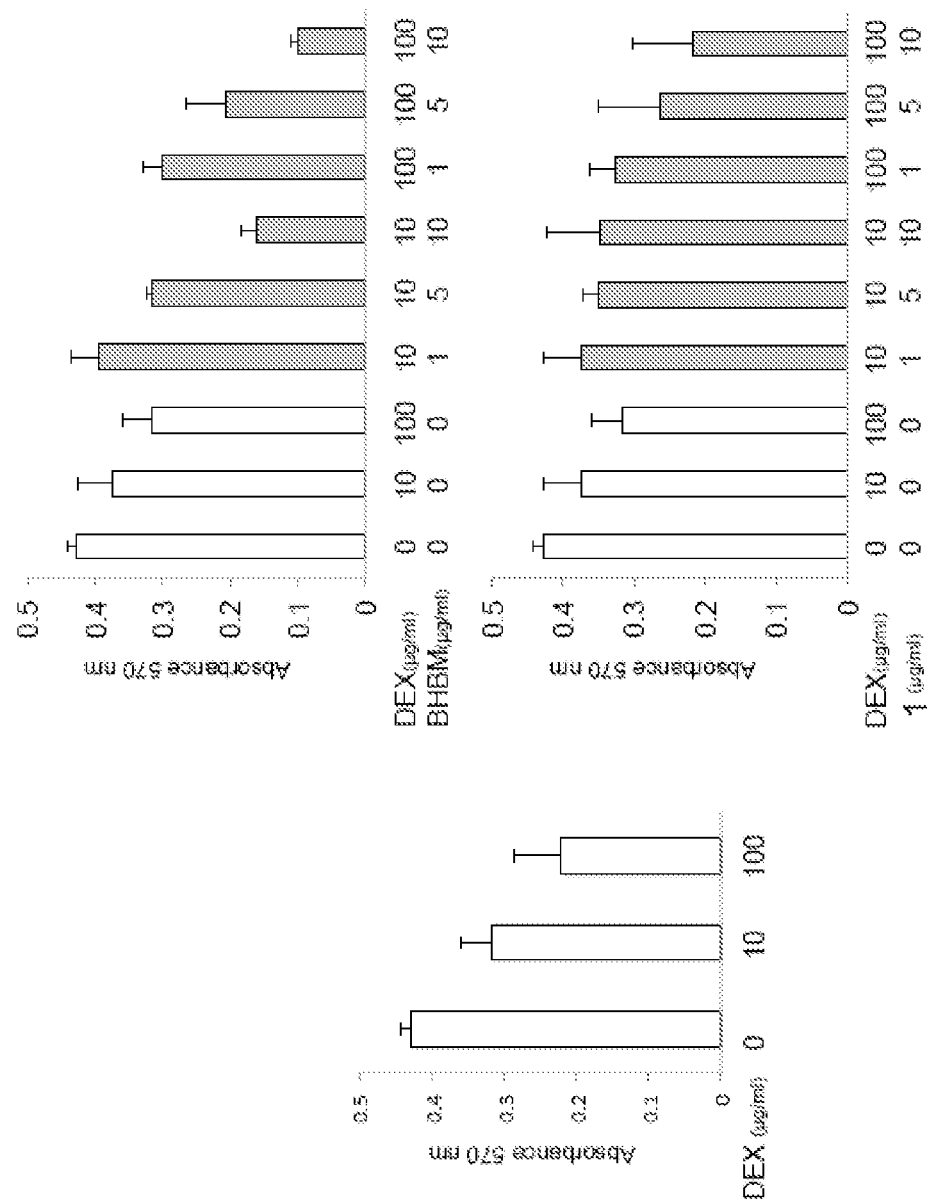
FIG. 18: In vitro toxicity studies at 24 hr of dexamethasone (DEX) alone or in combination with BHBM or 1 using MTT assay in J774 mammalian cells.
Figure 19:
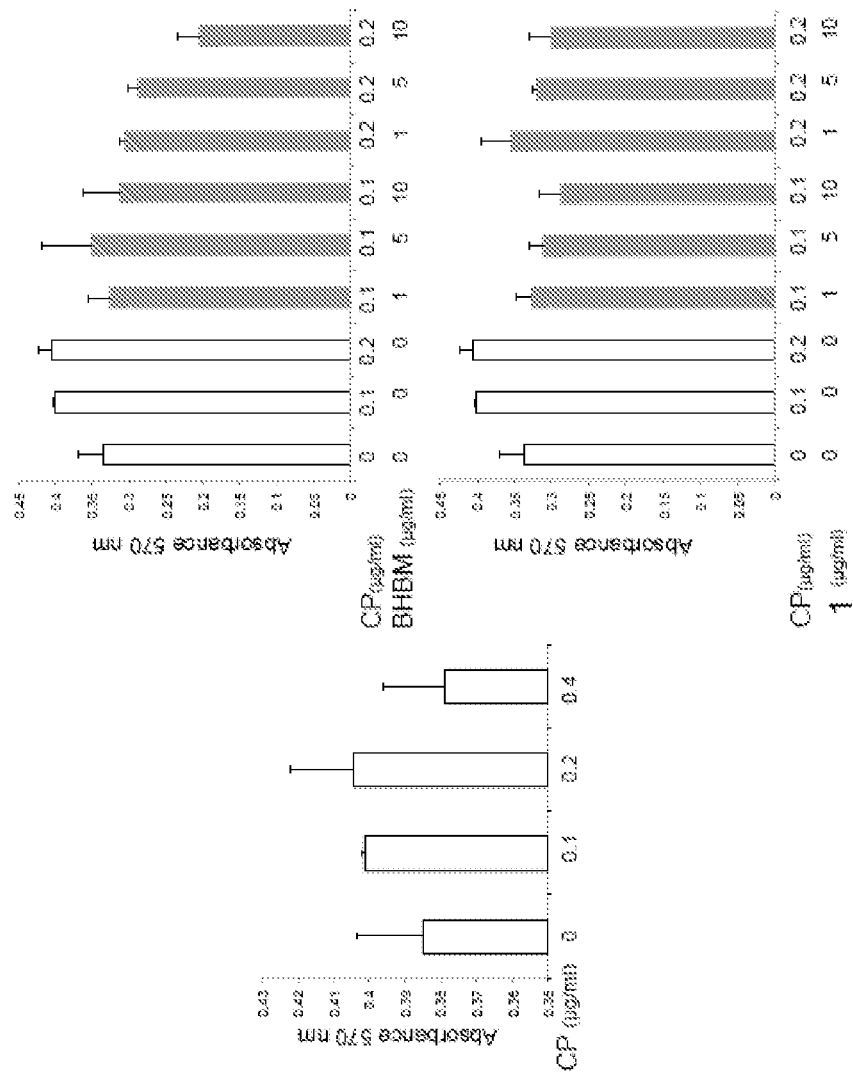
FIG. 19: In vitro toxicity studies at 24 hr of cyclophosphamide (CP) alone or in combination with BHBM or 1 using MTT assay in J774 mammalian cells.

The toxicity of both BHBM and 1 was assessed against J774.16, A549 and L2 mammalian cell lines. We found no or a slight toxicity in J774 (FIG. 17). $EC_{50}$ cytotoxicity at 48 hours was 50 μg/ml for both compound leading to a very good $EC_{50}/MIC_{80}$ selectivity index (50 for BHBM and >100 for 1). A slight to moderate toxicity was observed in A549 and L2 cell line. Interestingly, mammalian cell toxicity (using J774 cell line) was enhanced when BHBM was combined with dexamethasone (FIG. 18). The $EC_{50}$ for BHBM dropped to 10 μg/ml when the drug was combined to 10 μg/ml for dexamethasone. Also, 1 showed an increased toxicity when combined with dexamethasone (FIG. 18). Interestingly, this increased toxicity was not observed when the drugs were combined with another immunosuppressive drug cyclophosphamide (FIG. 19).

Because 1 showed increased toxicity when combined with corticosteroids, the efficacy against pneumocystosis was tested in an immunosuppressed mouse model in which CD4+ cells are depleted instead of using steroids. In this model, treatment with 1 improved survival and significantly decreased the number of asci in the lung at day 14 (FIG. 20). Importantly, no signs of toxicity were observed in this immunosuppressed animal model.

Example 8. BHBM and 1 have Antifungal Activity Against Invasive Candidiasis

Most *Candida* spp examined were resistant In vitro to both BHBM and 1. Previous studies however showed that, in this fungus, GlcCer is required for virulence through a mechanism other than facilitating growth at neutral/alkaline pH (33), which is the pH used in our library screening. Thus, we assessed whether BHBM inhibits GlcCer synthesis in *C. albicans* and, if so, if BHBM or 1 administration will be effective against invasive candidiasis. It was found that the synthesis of GlcCer in *C. albicans* cells is inhibited in a dose dependent manner, similar to the inhibition found in *C. neoformans* cells (FIG. 1A). Therefore, CBA/J mice were infected intravenously with a lethal dose of *C. albicans* cells and then treated them with either BHBM or 1 intraperitoneally using the same dose regimes used to treat cryptococcosis. It was found that 75% or 62.5% of mice treated with 1 or BHBM, respectively, were still alive after 21 days of infection, whereas the average survival of untreated mice was 10±1.7 days (FIG. 5A). Treated mice that survived the infection were sacrificed and their organs were excised and examined for tissue burden. The kidneys were the only organs found to be infected by *C. albicans* and such infection occurred only in approximately half of the mice examined (FIG. 5B). These results suggest that BHBM, and more efficiently 1, are able to clear *C. albicans* infection. They also suggest that, indeed, GlcCer is important for the pathogenicity of *C. albicans*, as found in previous studies (33).

Example 9. Pharmacokinetics

PK studies upon intravenous (IV) or intraperitoneal (IP) doses of BHBM were performed in immunocompetent control healthy mice and immunosuppressed/infected mice (FIG. 21). In immunocompetent mice, the half-life of BHBM upon IV high dose was found to be 1.03 hours. In the same group, the half-life of BHBM upon IP low and high doses were 1.70 and 1.43 hrs, with a bioavailability of 93.62% and 90.59% respectively (FIG. 21). In infected mice, the half-life of BHBM upon IV high dose was found to be 1.24 hours. In the same group, the half-life of BHBM upon IP low and high doses were 0.79 hours and 0.84 hours with a bioavailability of 93.62% and 100.33% respectively (FIG. 21). Overall, the results indicated that systemic exposure ($AUC_{0-t}$ and $C_{max}$) upon IP administration was higher in immunosuppressed/infected group compared to normal group. Preliminary studies on tissue distribution showed that BHBM is found in the brain tissue, suggesting that the molecule is able to cross the blood-brain barrier.

Example 10. Mechanism of Action

Figure 24:
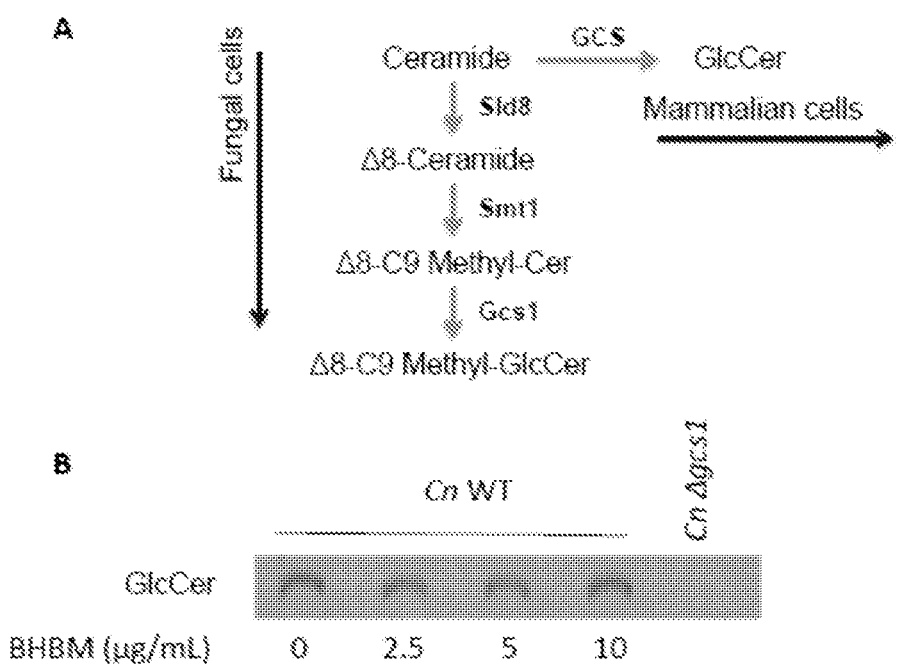
FIG. 24A: Pathway leading to the synthesis of glucosylceramide (GlcCer) in fungal and mammalian cells. GCS, mammalian glucosylceramide synthase; Sld8, shingolipid delta-8 desaturase; Smt1, shingolipid C9 methyl transferase; Gcs1, fungal glucosylceramide synthase.
FIG. 24B: In vitro Gcs1 activity using $^{14}$C-UDP glucose and C16 ceramide in presence of cell lysates extracted from either C. Neoformans (Cn) wild-type (WT) or Cn ΔGcs1 mutant strain in which Gcs1 is deleted without or with different concentrations of BHBM.

BHBM and 1 to inhibit GlcCer production in fungi and not in mammalian cells (FIG. 1A). The synthesis of GlcCer in fungi occurs in 3 steps (FIG. 24A). First, ceramide is disaturated in position 8 of the sphingosine backbone by the sphingolipid delta 8 desaturase (Sld8) producing the Δ8-ceramide. Next, the Δ8-ceramide is methylated in position 9 of the sphingosine backbone by the sphingolipid methyl transferase 1 (Smt1), producing the Δ8-C9-methylceramide. Finally, this ceramide is than used by Gcs1 to make Δ8-C9-methyl GlcCer. Ceramide is produced in the ER and transported to the Golgi by vesicle sorting for the synthesis of complex sphingolipids (Funato, K. & Riezman, H. 2001; Kajiwara, K. et al. 2014; Reggiori, F. & Conzelmann, A. 1998). Both Sld8 and Smt1 enzymes are not found in mammalian cells. In fact, mammalian cells make GlcCer from "ceramide" and, thus, their GlcCer is neither desaturaded nor methylated (Del Poeta, M. et al. 2014). Sld8, Smt1 and Gcs1 are also not found in the yeast model *Saccharomyces cerevisiae* and, thus, this yeast does not make any GlcCer. Thus, it was evaluated as to whether BHBM targets Gcs1, Smt1 or/and Sld8 in *C. neoformans*.

It was found that BHBM does not inhibit the in vitro activities of Gcs1 (FIG. 24B), Smt1 or Sld8 activities. These results suggest that inhibition of GlcCer production by BHBM must occur upstream of Sld8. This hypothesis is further supported by the fact that *S. cerevisiae* and *C. glabrata*, two fungi that do not produce GlcCer, are still partially sensitive to BHBM, although to a lesser extent than *C. neoformans* and other fungi. Hence, a *S. cerevisiae* library was used to identify the potential pathway(s) affected by BHBM. Although *S. cerevisiae* does not produce GlcCer, other genes involved in the sphingolipid pathway upstream Sld8 are conserved between this yeast and other fungi making it an appropriate yeast system to study this pathway.

Therefore, a *Saccharomyces cerevisiae* genome-wide variomic library was screened for genes that, when mutated, might confer resistance to BHBM. Such resistance genes could define target(s) of the compound. A previous proof-of-concept study has shown that this method could be used to rapidly identify targets of small molecules (Huang, Z. et al. 2011). However, BHBM-resistant clones could not be isolated despite multiple attempts. Therefore, a *S. cerevisiae* HIP-HOP heterozygote mutant library was screened (Huang, Z. et al. 2011). The rationale for using the latter for drug-target identification is that if a gene/enzyme is targeted by a drug then the respective heterozygote mutant will be more sensitive to the drug compared to the wild-type "diploid" strain.

Figure 25:
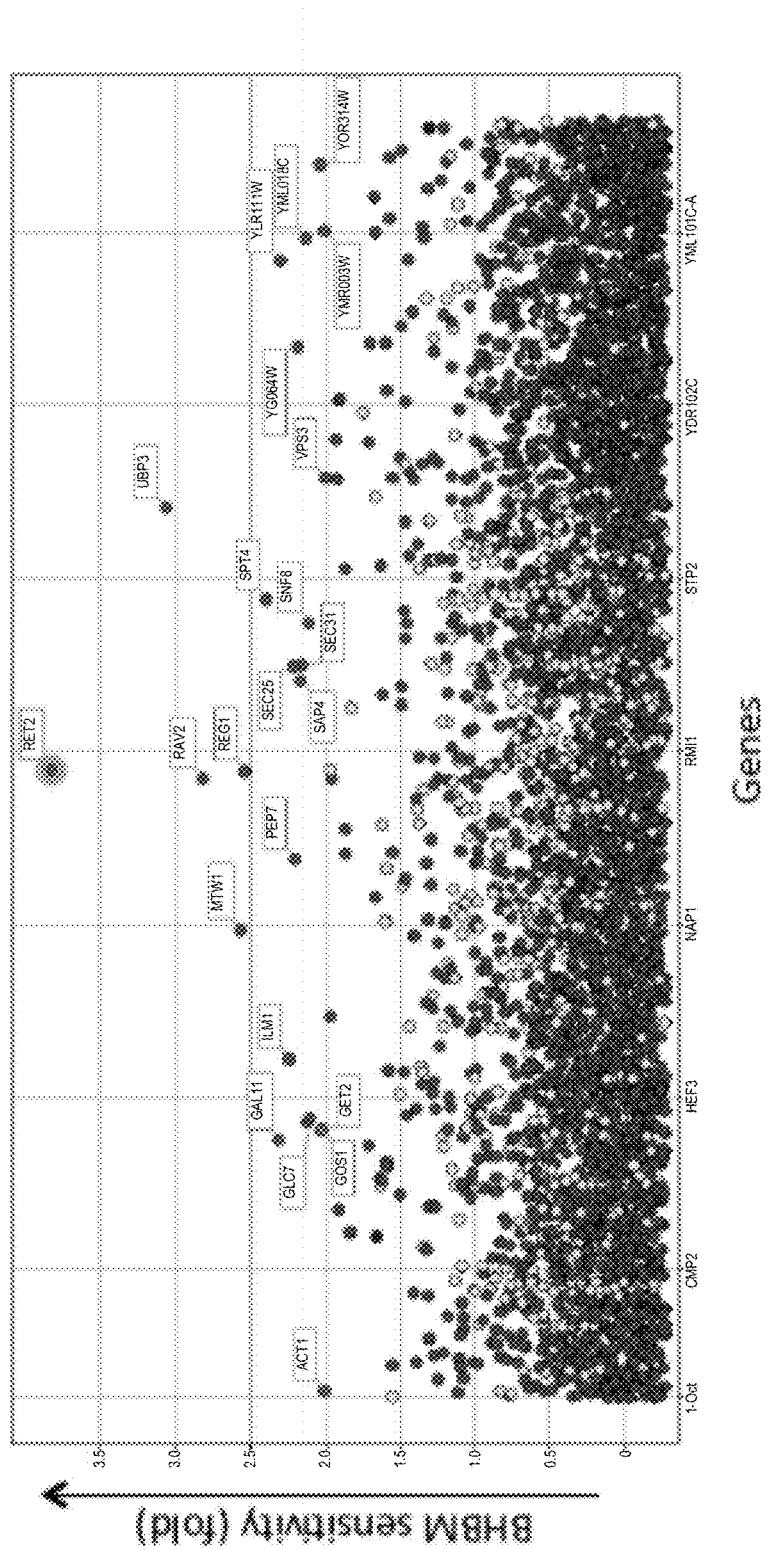
FIG. 25: Hetero insufficiency profiling and homozygoze insufficiency profiling (HIP-HOP) analysis of BHBM. Scatter plot of Saccharomyces cerevisiae heterozygote library treated with BHBM. Plot shows few genes clearly involved in sensitivity to BHBM (see Table 3).

Out of 5,900, 24 heterozygote mutants were found that were >2-fold more sensitive to BHBM compared to the diploid strain (FIG. 25 and Table 3). In these 24 genes, 8 are dubious open reading frames or with no homologies in *C. neoformans*. Among the remaining 16 genes, 9 genes (RET2, UBP3, SEC26, PEP7, SEC31, YML018C, SNF8, GOS1, and RET3) are involved in the regulation of vesicle sorting or transport between Golgi and ER (Table 3). The genes identified are conserved in *C. neoformans* but none of these genes have been characterized. Among the others 7, 6 genes (MTW1, REG1, SPT4, SAP4, GLC7, and ACT1) regulate chromatin organization, cell cycle progression or cell division (Table 3). As briefly discussed above, vesicle transport is the main mechanism by which ceramide is transported between the ER and Golgi for the synthesis of GlcCer and other complex sphingolipids (55-57) and indeed, the loss of GlcCer in *C. neoformans* (Δgcs1) results in cell cycle arrest and block of cell division. Therefore, these data suggest that enzymes involved in ceramide transport may be the target(s) of BHBM resulting in potential inhibition of the enzymes involved in the regulation of cell cycle due to the reduction in GlcCer levels.

TABLE 3

HIP-HOP results of *S. cerevisiae* heterozygote library mutants treated with BHBM. Out of ~6,000 heterozygote mutants, 24 showed at least 2-fold increased sensitivity to BHBM. Out of 24 genes, 8 are dubious open reading frames or have no homologous in *C. neoformans*. Among the remaining 16 genes (shown below), 9 genes (RET2, UBP3, SEC26, PEP7, SEC31, YML018C, SNF8, GOS1, and RET3-gray shaded) are involved in the regulation of vesicle sorting or transport between Golgi and ER. Among the others, 6 genes (MTW1, REG1, SPT4, SAP5, GLC7, and ACT1) regulate chromatin organization, cell cycle progression or cell devision. Vesicle transport is the main mechanism by which ceramide is transported between ER and Golgi for the synthesis of GlcCer. Importantly, loss of GlcCer in fungi results in cell cycle arrest and block of cell division.

| Gene | Fold | Function in *S. cerevisiae* | Homologous in *C. neoformans* |
| --- | --- | --- | --- |
| RET2 | 3.8 | RETrieval from ER. COPI vesicle coat. Involved in retrograde transport between Golgi and ER. | CNAG_01414: hypothetical subunit of the COPI complex. |
| UBP3 | 3.0 | UBiquitin-specific Protease. Involved in protein de-ubiquitination. Regulates anterograde and retrograde transport between ER and Golgi. | CNAG_06920: hypothetical ubiquitin carboxyl-terminal hydrolase 10. |
| MTW1 | 2.5 | Mis TWelve-like. Essential component of the MIND kinetochrore complex. Key regulator of cell cycle progression and cell division | CNAG_04157: hypothetical kinetochore protein. MTW1. |
| REG1 | 2.5 | REsistance to Glucose repression. Glucose metabolism. Involved in the regulation of nucleocytoplasmic shuttling of Hxk2p. Interacts with GLC7 in regulating cell division. | CNAG_05768: hypothetical protein. |
| SPT4 | 2.3 | SuPpressor of Ty's. Component of the DSIF complex. Involved in the regulation of transcription elongation and chromatin organization. | CNAG_04204: hypothetical transcription elongation factor SPT4. |
| SEC26 | 2. | SECretory. COPI vesicle coat. Involved in retrograde transport between Golgi and ER | CNAG_03299: hypothetical protein. |
| PEP7 | 2.2 | CarboxyPEPtidase Y-deficient. Facilitate vesicle-mediated sorting. Facilitates vesicle-mediated sorting. Regulates Golgi to vacuole transport and vesicle docking involved in exocytosis. | CNAG_07848: hypothetical protein. |
| SAP4 | 2.1 | Sit4 Associated Protein. Required for cell cycle progression. | CNAG_03399: hypothetical Sit4 protein. |
| SEC31 | 2.1 | SECretory. COPI and COPII vesicle coat. Involved in vesicle transport between Golgi and ER. | CNAG_04803: hypothetical protein. |
| YML018C | 2.1 | Localized in vacuolar membranes. Regulates transmembrane transport. | CNAG_01467: hypothetical protein. |
| GLC7 | 2.1 | GlyCogen. Regulates cell cycle progression and cell division. | CNAG_03706: hypothetical protein. |
| SNF8 | 2.1 | Sucrose NonFermenting. Component of the ESCRT-II complex. Regulates vesicle sorting. | CNAG_05704: hypothetical protein. |
| GOS1 | 2.1 | GOlgi Snare. v-SNARE protein. Regulates ER to Golgi vesicle transport and vesicle fusion. | CNAG_03287: hypothetical Golgi SNARE protein. |
| ACT1 | 2.0 | ACTin. Involved in the regulation of bud growth and cell division. | CNAG_00483: Actin. |
| VPS3 | 2.0 | Vacuolar Protein Sorting. Regulates vacuolar (H+)-ATPase. | CNAG_07328: hypothetical protein. |
| RET3 | 2.0 | RETrieval from ER. COPI vesicle coat. Involved in retrograde transport between Golgi and ER. | CNAG_04089: hypothetical subunit of the COPI complex. |

Example 11. Biochemical End Microscopic Studies Upon Treatment with BHBM

Figure 6A:
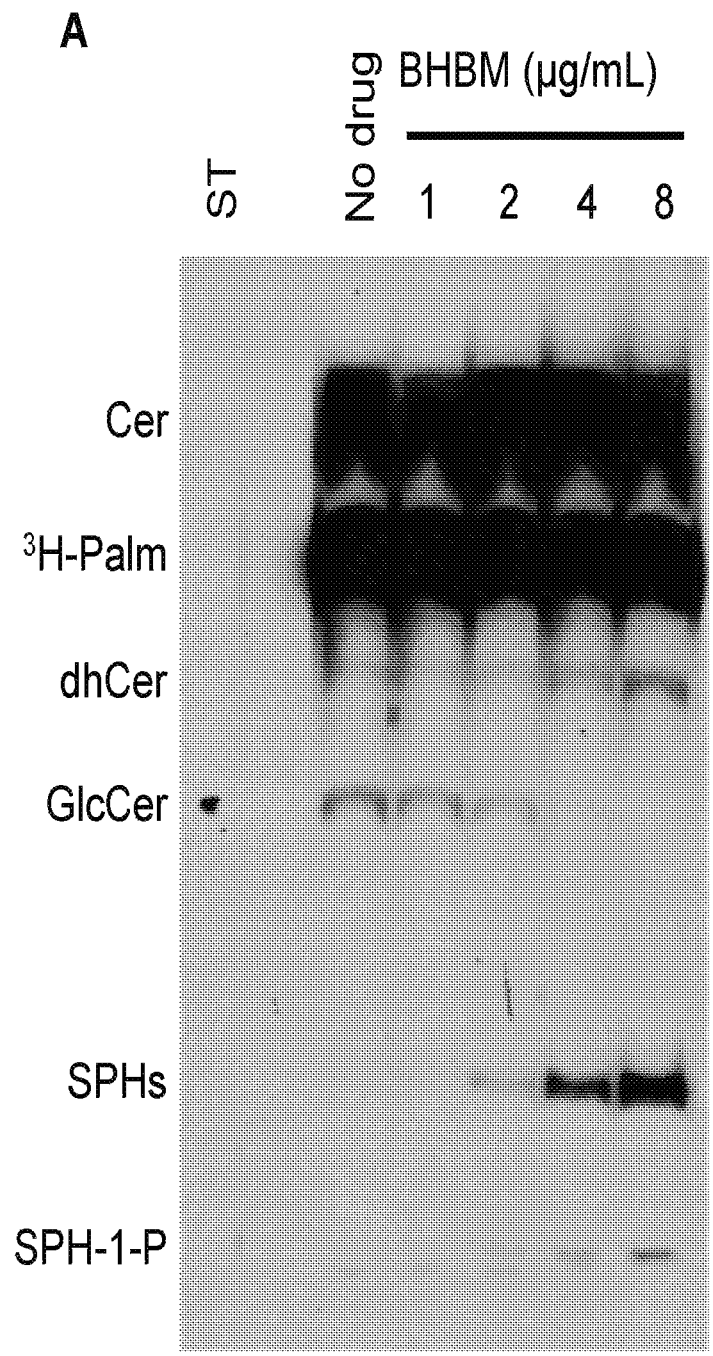
FIG. 6A: Measurements of *C. neoformans* sphingolipids upon treatment with BHBM. Thin layer chromatography of sphingolipids of untreated or BHBM-treated *C. neoformans* cells after in vivo labeling with $^3$H palmitate.
Figure 26:
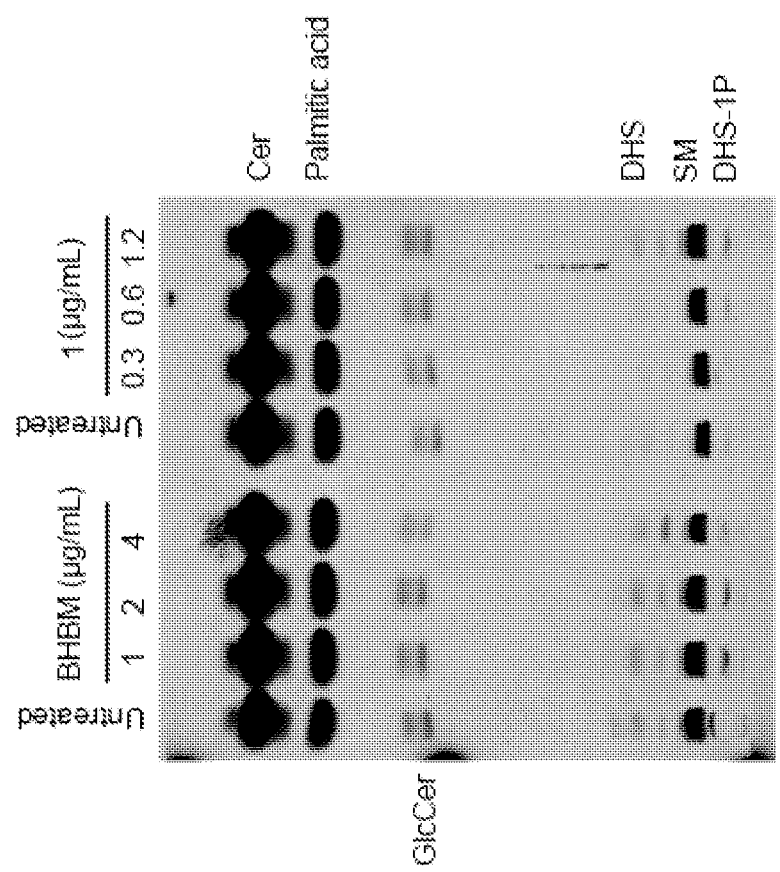
FIG. 26: Tritiated palmitate in vivo labeling of J774 cells in the presence or absence of BHBM or 1. Thin layer chromatography showed no significant changes in the synthesis of mammalian GlcCer upon treatment.
Figure 27:
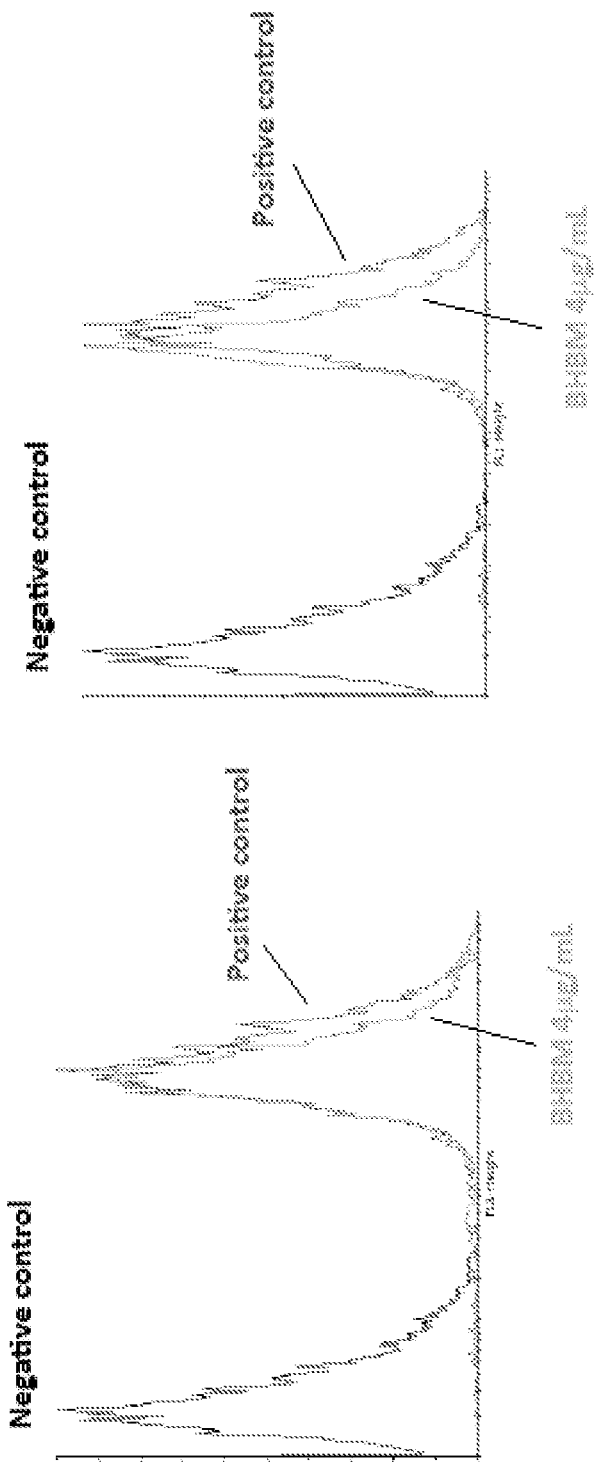
FIG. 27: Bone marrow derived macrophages treated with BHBM for three days. Presence of mammalian GlcCer was detected using FITC labeled cholera toxin subunit B, which binds specifically to mammalian GlcCer. BHBM treatment did not significantly affect GlcCer level.

To support the genetic data, biochemical studies were performed to observe changes in sphingolipid level upon BHBM treatment by TLC and mass spectrometry. As illustrated in FIG. 6, GlcCer decreased and dihydroceramide, sphingosine and sphingosine-1-phosphate increased upon treatment with BHBM (FIG. 6A). These changes were confirmed by mass spectrometry (FIGS. 6B, 6C and 6D). Importantly, no significant changes of GlcCer were observed in mammalian cells at early (radioactive labeling, FIG. 26), or at late time points (fluorescent labeling, FIG. 27), or by mass spectrometry. Taken together, these results suggest that in fungal cells BHBM and 1 most likely target specifically the metabolism or/and transport of certain ceramide species which are then used for the synthesis of GlcCer.

Example 12. Treatment of Fungal Cells with BHBM Affects Golgi Morphology and Cellular Sterol Concentration The well defined relationship between lipid composition, membrane architecture and fungal lipid secretion (Huang, Z. et al. 2011; Oliveira, D. L. et al. 2009) led to the evaluation as to whether exposure of fungal cells to BHBM would affect Golgi morphology, since this organelle is a well known regulator of secretory processes. Staining of control yeast cells with C6-NBD-ceramide revealed the typically disperse Golgi morphology of *C. neoformans* (FIG. 7A) (Rizzo, J. et al. 2009; Kmetzsch, L. et al. 2011). Staining of *C. albicans* with C6-NBD-ceramide was limited to well-defined areas of the cytoplasm. BHBM treatment did induce significant alterations in the Golgi morphology, particularly in *C. albicans*, in which changes in the Golgi morphology were dramatic, including an apparent diffusion of Golgi-related structures to peripheral regions of the cell. DAPI staining revealed that nuclear morphology remained unaffected in all cases. BHBM treatment resulted in marked reductions of secreted vesicles as measured by their sterol content by both *C. neoformans* (FIG. 7B) and *C. albicans* (FIG. 7C). These results further confirmed that BHBM and 1 target vesicular transport in fungi.

Example 13. Comparison of Antifungal Activity of BHBM and 1 with Existing Antifungals (Fluconazole and Amphotericin B)

Mouse survival study was performed to test the efficacy of BHBM and 1 against invasive cryptococcal infection of the central nervous system (CNS). For these studies, the mice were infected intravenously resulting in rapid development of CNS infection. A triazole (fluconazole) and a polyene (amphotericin B) were also included in these studies to test the efficacy of BHBM and 1 to commonly used drugs. BHBM and 1 were used at concentrations of 1.2 mg/kg/day, which were used for intranasal infection studies. Amphotericin B and fluconazole were used at concentrations of 1.2 mg/kg/day and 10 mg/kg/day, respectively. These concentrations were within the concentration range previously used for studies of cryptococcosis in murine models (0.5 to 1.5 mg/kg/day for amphotericin B and 3 to 30 mg/kg/day for fluconazole) (Barchiesi et al. 2000).

Figure 29:
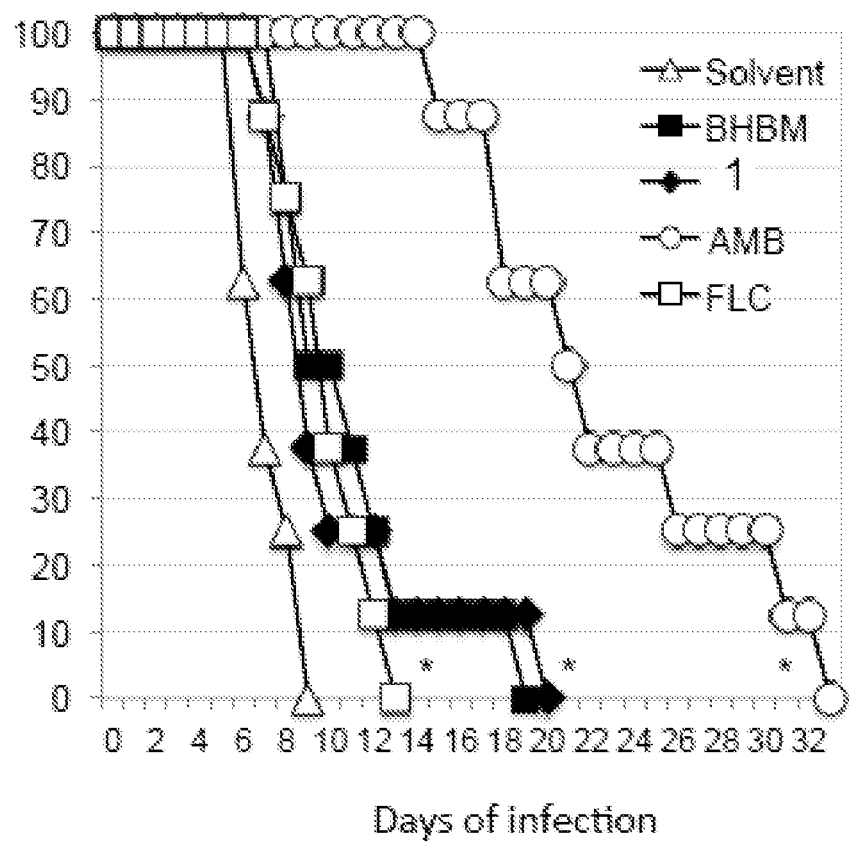
FIG. 29: Comparison of BHBM and 1 with fluconazole and amphotericin B on cryptococcosis. Survival of mice infected intravenously with C. neoformans. The average survival of the control group (solvent) was 7.0±1.1 days. The BHBM, 1 and fluconazole (FLC) groups showed an average survival of 11.1±3.7 (P<0.005), 10.5±4.2 (P<0.01) and 10.0±2.0 (P<0.005), respectively. Amphotericin B (AMB) group had an average survival of 23.5±6.5 (P<0.005). Statistical analysis for survival studies was performed using Kruskal-Wallis test.

All mice in the vehicle treated (control) group, succumbed to the infection within nine days (FIG. 29). This was in agreement with the study of Barchiesi using the same infection method (Barchiesi et al. 2000). All drugs prolonged mice survival significantly compared to control although none of the drugs completely protected the mice from the infection. Mice treated with BHBM and 1 succumbed 11.1±3.7 and 10.5±4.2 days post-infection, which was similar to the survival pattern observed with fluconazole (10±2 days post-infection) (FIG. 29). The comparable efficacy of BHBM and 1 against fluconazole is quite significant considering that the concentration of fluconazole used for treatment was almost eight times higher than both drugs. Amphotericin B was the most efficient drug in prolonging mice survival (without completely protecting the mice); however, the well-established high toxicity of this drug has made it an unfavorable choice for treatment of cryptococcal infections.

Since both BHBM and 1 were effective in protecting mice from cryptococcosis following intranasal infection of mice, it was decided to push the envelope and examine their effectiveness against an invasive model of CNS cryptococcal infection. Fluconazole and amphotericin B were included in these studies. In addition to being mainstream drugs against cryptococcal infections; these drugs can penetrate the cerebrospinal fluid, thus providing a good benchmark to compare the efficacy of our drugs against CNS infections (Paterson, L. et al. 1978; Tucker, R. et al. 1988).

Mice survival studies showed that both BHBM and 1 were similar to fluconazole in prolonging mice survival (FIG. 29). This is of significant importance as the concentration of fluconazole used for these studies was almost eight times higher than that of BHBM and 1, suggesting that these drugs could be more effective than fluconazole. Toxicity studies showed that both BHBM and 1 are well tolerated by mice (FIGS. 14-16), the low concentration of drugs needed to prolong mice survival further bolsters these results as lower concentration can lead to lower toxicity. The observation that BHBM and 1 both prolong mice survival following CNS infection suggests that these drugs are also able to penetrate the CNS. This is corroborated by our preliminary studies showing the presence of BHBM in brain tissue.

In the mice survival study amphotericin B was the most effective drug in protecting the mice against cryptococcosis (FIG. 29). However, it is well established that amphotericin B suffers from drawbacks such as adverse reactions and nephrotoxicity, thus its use as a stand-alone drug is undesirable (Gallis, H. A. et al. 1990; Sawaya, B. P. et al. 1995). Amphotericin B has been used in combination therapy with other drugs for the treatment of cryptococcosis, since our drugs have a different mechanism of action compared to polyenes, they could be favorable potential candidates for combination therapy with amphotericin B (Larsen, R. A. et al. 1990; Graybill, J. R. et al. 1980).

Example 14. Electron Microscopy Analysis of *C. Neoformans* Cells Treated with BHBM or 1

Figure 30D:
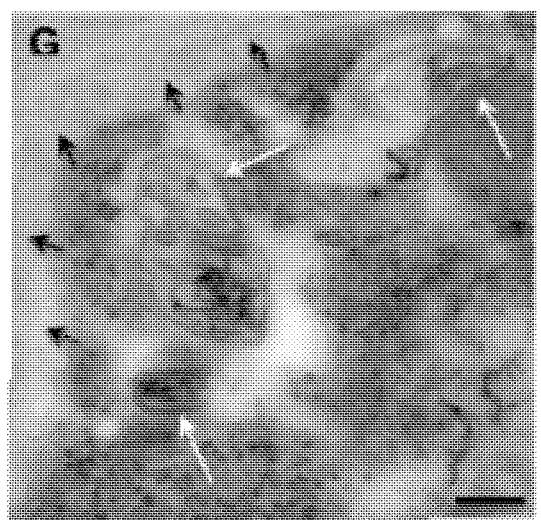
Figure 31:
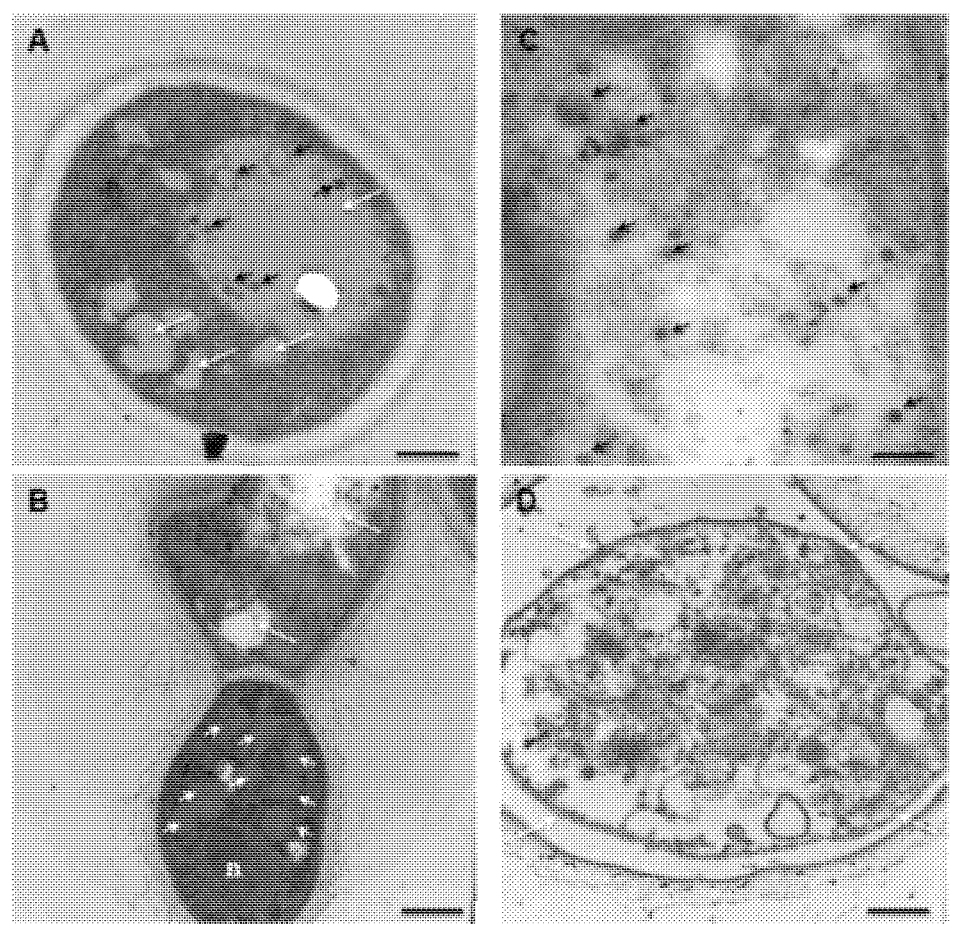
FIG. 31A-D: TEM images of C. neoformans treated with 4 μg/mL of BHBM (A or D) or 1 (B and C) for 6 hours. Giant multivescular bodies (long white arrows are present in A, B, and D containing multiple vesicles (black arrows) which eventually replace the entire cell (D). (C) is a higher magnification image of a multivescular body in (B). Short arrows in B illustrate the many vacuoles present in this bud cell. Black scale bar=500 nm in A and B; 100 nm in C and D.

The effect of drug treatment on cell ultrastructure was examined using Transmission Electron Microscopy (FIG. 30). Electron micrographs showed an accumulation of large vacuoles in the cells treated with both BHBM and 1 (FIG. 30A-C). The number of vacuoles per $\mu m^2$ of cell surface area were 0.84±0.58 in BHBM and 0.93±0.54 in 1 treated cells, respectively compared to 0.33±0.36 in untreated cells. These vacuoles accumulate numerous small vesicles and aberrant membrane compartments similar to those observed in *S. cerevisiae* mutants with deficiency in the vesicular secretory pathway between Golgi and ER and vacuolar integrity (Hua, Z. & Graham, T. R. 2003; Salama, N. R. et al. 1997; Bryant, N. J. & Stevens, T. H. 1998; Jarmoszewicz, K. et al. 2012; Webb, G. C. et al. 1997). Interestingly, some of these compartments appear to resemble aberrant multivesicular bodies (FIG. 30D), which in some BHBM and 1 treated cells occupy the entire cells (FIG. 31).

Since the HIP-HOP library screening had identified genes involved in vesicle sorting and transport as potential targets of BHBM and since fluorescent microscopy using NBD-ceramide suggest an alteration of the Golgi apparatus in treated cells, we used TEM to investigate the effect of drug treatment on vesicle transport phenomena. TEM images showed a significant accumulation of vacuoles in the drug treated cells (FIG. 30A-C). These vacuoles will eventually fuse to form giant vacuoles containing numerous small vesicles that eventually will replace the entire structure of the cells. This suggests that after only 6 hours of treatment the normal cellular structure is already significantly altered. This is not observed in untreated cells or in mammalian cells treated with the drugs for 72 hours.

Interestingly, multiple abnormal membrane structures containing numerous small vesicles were also observed in BHBM and 1 treated cells (FIG. 30D), which are consistent with multivesicular bodies. The shape of vesicles in multivesicular bodies is irregular and eventually they confluent in large vesicular bodies that totally replace the normal cell structure (FIG. 31).

The aberrant multivesicular bodies loaded vesicles found in the BHBM and 1 treated cells also suggest that the vesicular transport between the trans-Golgi network, the vacuole and endosome is also affected by BHBM and 1. If these vesicles are important for the transport and recycling of methylated ceramide then GlcCer synthesis is arrested. It is also possible that BHBM only target the vesicular intracellular transport and that the defect of extracellular vesicular secretion is due to the lack GlcCer, as this sphingolipid is contained in these secretory vesicles (Nimrichter, L. & Rodrigues, M. L. 2011) and thus, it may help to stabilize their membrane for proper secretion. The lack of GlcCer in the drug-treated cells may account for this phenotype as this sphingolipids is contained in these secretory vesicles and thus, it may help to stabilize their membrane for proper trafficking.

These abnormal membrane structures and accumulation of vacuoles have also been reported in a *S. cerevisiae* mutant deficient in NEO1 gene, which is required for COPI-dependent transport from the Golgi to the ER (Bryant, N. J. & Stevens, T. H. 1998) and in a mutant deficient in SEC31, which encodes for a subunit of COPII vesicle coat protein important for the ER-Golgi transport (Salama, N. R. et al. 1997) and in the SLA2 mutant, that regulates vesicle transport and endocytosis (Mulholland, J. et al. 1997; Wesp, A. et al. 1997). Various VPS/PEP genes have been also implicated in the regulation of the proper trafficking of vesicles from the trans-Golgi to the vacuole in *S. cerevisiae* (Bryant, N. J. & Stevens, T. H. 1998; Jarmoszewicz, K. et al. 2012; Webb, G. C. et al. 1997) and in *Candida albicans* (Palmer, G. E. 2011). Intriguingly, the genes that regulate COPI, COPII, and trans-Golgi vesicular trafficking were also identified by the HIP-HOP screening assay as the potential target(s) of BHBM (Table 2) and, as discussed herein, SLA2 was identified in the sequencing of the BHBM-resistant strain.

Example 15. Treatment of Fungal Cells with BHBM or 1 Affects Intracellular Vesicular Membrane Organisation and Structure To further validate the effect of BHBM and 1 on vesicular structure and organization, the effect of drug treatment on cell ultrastructure was examined using Transmission Electron Microscopy (FIGS. 7 & 30). Electron micrographs showed an accumulation of large vacuoles in the cells treated with both BHBM and 1 (FIG. 30A-C). The number of vacuoles per $\mu m^2$ of cell surface area were 0.84±0.58 in BHBM and 0.93±0.54 in 1 treated cells, respectively compared to 0.33±0.36 in untreated cells. These vacuoles accumulate numerous small vesicles and aberrant membrane compartments similar to those observed in *S. cerevisiae* mutants with deficiency in the vesicular secretory pathway between Golgi, E R and plasma membrane (Hua, Z. & Graham, T. R. (2003); Salama, N. R. et al. 1997); Bryant, N.J. 6 Stevens, T. H. 1998; Jarmoszewicz, K. et al. 2012; Webb, G. C., et al. 1997; Mulholland, J. et al. 1997) identified by the HIP-HOP and the genome sequencing of the BHBM-resistant strain. Interestingly, some of these compartments appear to resemble aberrant multivesicular bodies (FIG. 30D), which in some BHBM and 1 treated cells occupy the entire cells (FIG. 31).

In order to pinpoint the fungal molecular target of BHBM, a BHBM resistant mutant was generated using the *S. cerevisiae* RYO0622 strain. This strain is particularly suitable for drug target discovery because bears precise deletions of all 16 ATP-binding cassette transporters with clades associated with multidrug resistance (Suzuki, Y., et al. 2007). Following the methodology described in the method section, one stable resistant colony to BHBM was obtained, whose genome was sequenced along with the parent genome and compare with the genome of NCBI sacCer3. Using GATK, 53 SNVs unique to the parent, 39 unique to the revertant, and 202 shared by the parent and revertant were identified. Of the 39 SNVs unique to the variant 10 were classified as low quality calls leaving 29 revertant-specific SNVs that pass the quality threshold. Out of 29, 17 mutations were eliminated because they were inconsistently present (<90%) in the revertant reads or they showed a low coverage depth (<100 reads) in the parent data. The resulting 12 mutations are illustrated in the Supplementary File RYO0622-SR.xlsx. These 12 mutations are localized in the intergenic region ARS209 (7 mutations), upstream the ATG start site of the OM14 gene (1 mutation), in the coding region of the ALP1 gene (3 mutations) and SLA2 gene (1 mutation) (Table 4).

TABLE 4

Sequence comparison using the Genome Analysis Toolkit (GATK) of *S. cerevisiae* RYO0622 sensitive and resistant strains to BHBM. Out of ~1,000,000 cells, one colony became resistant to BHBM (see methods). The genome of the resistant strain, along with the genome of the parent sensitive strain, was sequenced. The two genomes were then compared to NCBI sacCer3 using GATK and Strelka. The Table illustrates mutations in genes involved in ER-Golgi vesicular trafficking and endocytosis (SLA2 and ALP1).

| Gene | Chromosome position, Nucleotide mutations, AA mutation and location | Function in *S. cerevisiae* | Homologous in *C. neoformans* |
|---|---|---|---|
| SLA2 | Chr XIV 189585, C-T, Ser512Phe | Synthetic Lethal with ABP1 Glucose metabolism. Also called END4 and MOP2. Involved in actin filament organization, PMA1 localization and function, endocytosis, exocytosis, and vesicle transport. Interacts with ACT1, VPS (see HIP-HOP) and SEC family. | CNAG_02237 hypothetical protein. |
| ALP1 | Chr XIV 136877 A-G, Pro253Pro Chr XIV 136894 T-C, Ile255Ile Chr XIV 136900 T-A, Asn261Ser | Arginine transporter, basic amino acid permease. ALP1 has a paralog, CAN1. Interacts with the sphingolipid metabolizing gene ISC1 and it is regulated by RIM101. Important in endocytosis and drug resistance. | CNAG_07902 hypothetical protein. |

Strelka v1.0-14 (Saunders, C. T., et al. 2012) was run to call differential (somatic) variants using the parent as the "normal" sample and the revertant as the "tumor" sample; otherwise the provided default configuration for bwa reads was used unchanged. Strelka identified 18 "somatic" SNVs between the revertant and parent. Nine mutations identified by GATK were also confirmed by Strelka. The difference between Strelka and GATK may be attributable to the differences in specificity of the methods.

The involvement of BHBM in targeting vesicle transport is further confirmed by the sequencing of the *S. cerevisiae* resistant colony to BHBM. The revertant showed mutations in the SLA2, ALP1 genes and in few intergenic regions. Particularly interesting is the mutation found in the SLA2 gene (Table 4). The SLA2 (also called END4 or MOP2)

gene regulates vesicle transport and endocytosis in *S. cerevisiae* (Mulholland, J. et al. 1997; Wesp, A. et al. 1997). The temperature sensitive Δsla2 mutant accumulates Golgi derived secretory vesicles strikingly similar to the vesicles observed by our electron microscopy of BHBM treated *C. neoformans* cells (FIG. 30). The SLA2 gene also regulates cell cycle progression in *S. cerevisiae* and *C. albicans* and the *Candida* gene complements *S. cerevisiae* Δsla2 mutant, suggesting the function of this gene is conserved among fungi (Asleson, C. M., et al. 2001; Gale, C. A. et al. 2009) and most likely in *C. neoformans*. The SLA2 gene is essential for fungal growth at 37° C. (Mulholland, J. et al. 1997; Wesp, A. et al. 1997) and this explains why BHBM resistant strains were not found in our *C. neoformans* screening (performed at 37° C.), but were found in *S. cerevisiae* screening (performed at 30° C.).

The Sla2 protein has 3 major domains: the N-terminus, the coil and the C-terminus domains (Gottfried, I. et al. 2010). The C-terminus domain contains the I/LWEQ modules and interacts with actin (McCann, R. O. & Craig, S. W. 2010). This domain shares high similarity with the mammalian counterpart protein Talin (McCann, R. O. & Craig, S. W. 1997). On the other hand, the coil domain and the N-terminus domains are highly divergent from Talin and these domains specifically control endocytosis and vesicle transport in yeasts. Interestingly, the coil domain interacts with Rvs167 for controlling endocytosis and vesicle transport [13] and our HIP-HOP analysis showed Rvs167 to be 1.7 time more sensitive to BHBM (Table 2). The coil domain is also important for the dimerization of Sla2, which appears to be required for activity (Gourlay, C. W. et al. 2003). The point mutation in the resistant colony is localized in the coil domain resulting in changing of the amino acid 512 from serine to phenylalanine. Since mutations in the coil domain significantly increase the half-life of Sla2 (Mulholland, J. et al. 1997; Wesp, A. et al. 1997; Ynag, S. et al. 1999), it is possible that the mutation at 512 is a gain of function. Thus, it was proposed that the target of BHBM is the coil or/and the N terminus of Sla2. It is possible that BHBM acts to break the dimer, which is reinforced or simply prevented by the Ser512Phe mutation. These domains are fungal specific and are different from the counterpart regions of the human homolog Talin. This explains the effect of BHBM in blocking vesicle transport and GlcCer synthesis in fungi but not in mammalian cells.

It is possible that the other mutations identified in the resistant strain are also involved (Table 4). Particularly, ALP1 regulates the transport of basic amino acids, which might be involved in regulating fungal tolerance to alkaline environment, in which BHBM is indeed particularly active. Also, Alp1 interacts with inositol sphingolipid phospholipase C 1 (Isc1) enzyme, but although Isc1 is an important enzyme in the sphingolipid pathway for the generation of long chain ceramide (Farnoud, A. M. et al. 2014; Henry, J. et al. 2011; Shea, J. et al. 2006; Garcia, J. et al. 2008), it is not directly involved in the synthesis of GlcCer. Mutations or/and point mutations of these genes identified by HIP-HOP and by the genome sequencing can be generated for testing whether the genes are in fact targeted by the drug.

Example 16. Synthesis and In Vitro Activity and Toxicity of New Derivatives

Figure 22:
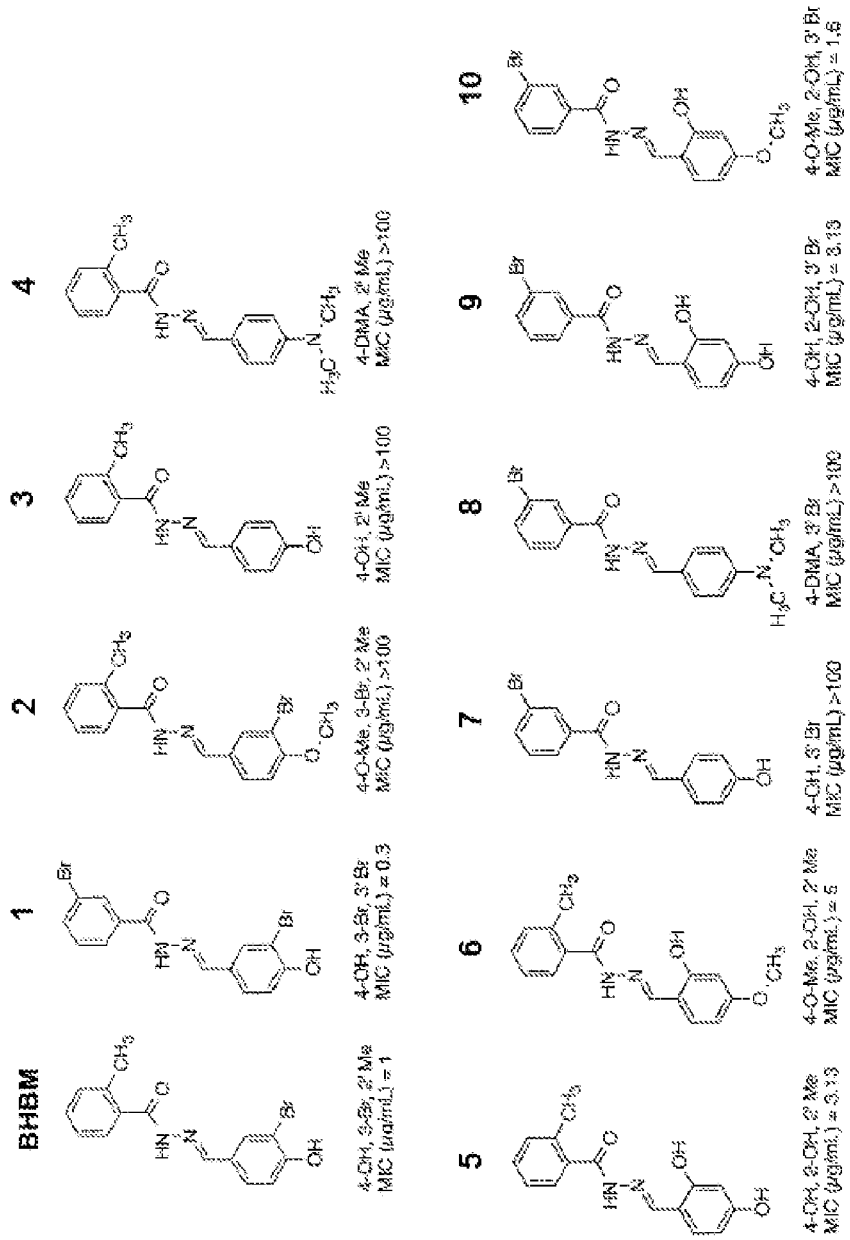
FIG. 22: $MIC_{80}$ of compounds BHBM and 1-10.

Although the compound BHBM is relatively safe when used alone, their in vitro toxicity increases when used in combination with corticosteroids. In addition, while active against *C. neoformans* and most dimorphic fungi, both BHBM is less effective against certain *Candida* spp. and *A. fumigatus*. Additionally, BHBM has a short half-life in bloodstream (~1.4 hour) and, although BHBM is very soluble, it required a small amount of DMSO (0.41) for complete dissolution. Additional compounds were synthesized with improved activity, improved toxicity and/or solubility profiles of BHBM and/or 1 (FIG. 22). It was found that compound 1 has improved activity (FIG. 23). Compound 9 is 50-fold more soluble than the parent 1 (FIG. 23). Compound 10 retained a potent In vitro activity against *C. neoformans*, with improved toxicity (FIG. 23).

Example 17. Additional Analogs

An additional aspect of the invention provides derivatives of compounds 1, 5, 6, 9 or 10 that also inhibit fungal shingolipid synthesis and are active as antifungal agents. These derivatives have analogous or improved activity to any one of compounds 1, 5, 6, 9 or 10.

Example 18. Cellular Targets

To pinpoint the cellular targets of BHBM, a second approach, generation of BHBM-resistant mutants was followed. The drug-sensitive *S. cerevisiae* RYO0622 strain was used for the generation of mutants (Suzuki, Y. et al. 2011). A pre-screening study exposing this strain to various concentrations of BHBM revealed that a drug concentration of 133 µg/mL completely inhibited yeast growth ($IC_{100}$ dose). Incubating $10^6$ cells of *S. cerevisiae* RYO0622 strain with BHBM at $IC_{100}$ dose resulted in seven resistant colonies, the genomes of which were sequenced and compared with the genome of NCBI sacCer3 using the Genome Analysis Toolkit (GATK). This analysis led to the identification of mutations in four genes (APL5, COS111, MKK1, and STE2) that were present in all resistant mutants.

The proteins encoded by these loci are known to be involved in vesicle trafficking, budding, and cell cycle progression (Knaus, M. et al. 2007; Elia, L. et al. 1998; Merchan, S. et al. 2011; Tongm, Z. et al. 2007), which are again in agreement with the observations of cell morphology and known phenotypes in the absence of GlcCer (Rittershaus, P. C. et al. 2006; Rodrigues, M. L. et al. 2000). These findings also closely match the pathway proposed by the HIP-HOP analysis. Interestingly, these four genes each interact with UBI4 which encodes ubiquitin and which is conjugated to proteins to target them for degradation. UBI4 is a member of the endomembrane recycling pathways as defined by Finley et al. (Finley, D. et al. 2012).

Figure 32A:
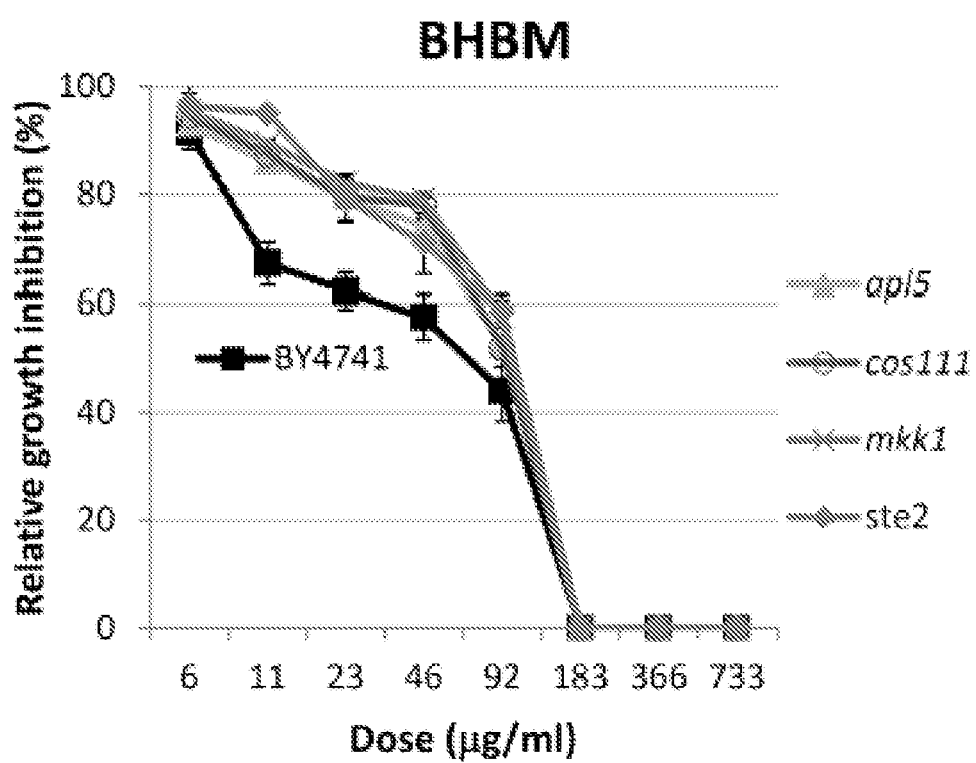
FIG. 32A-C: Effect of BHBM, fluconazole and methyl methane sulfonate (MMS) on wild-type BY4741 and Δap15, Δcos111, Δmkk1 and Δste2 deletion strains. Relative growth inhibition was calculated by the average rate after normalizing the OD600 values in drug wells against the DMSO control wells on each assay plate. The mutant strains show increased resistance to BHBM but not to fluconazole or MMS. Results from two independent growth assays.
Figure 32B:
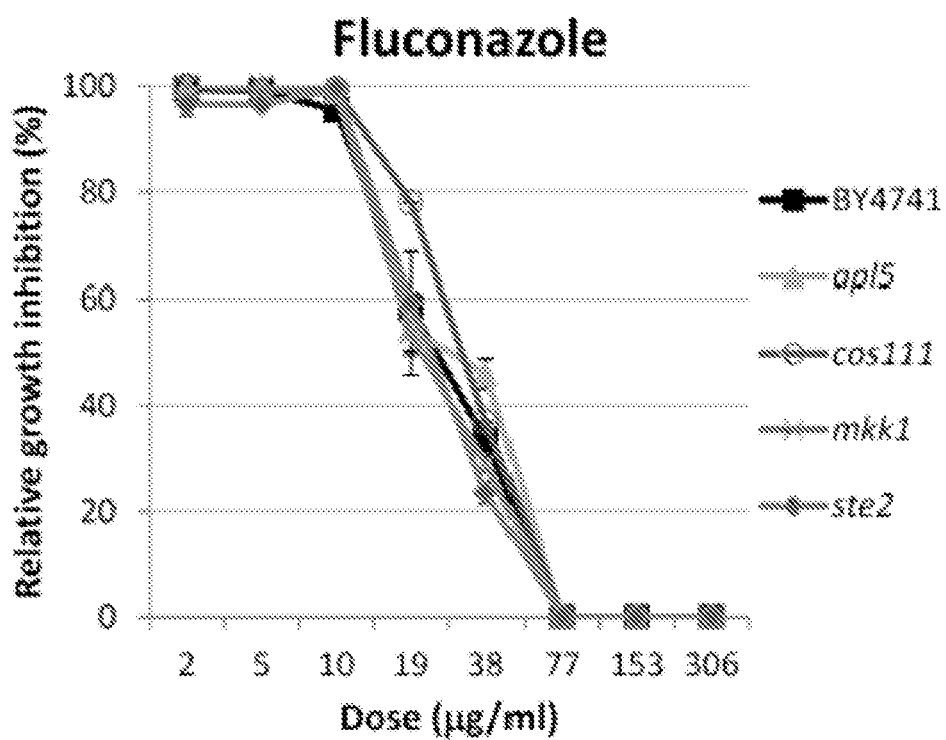
Figure 32C:
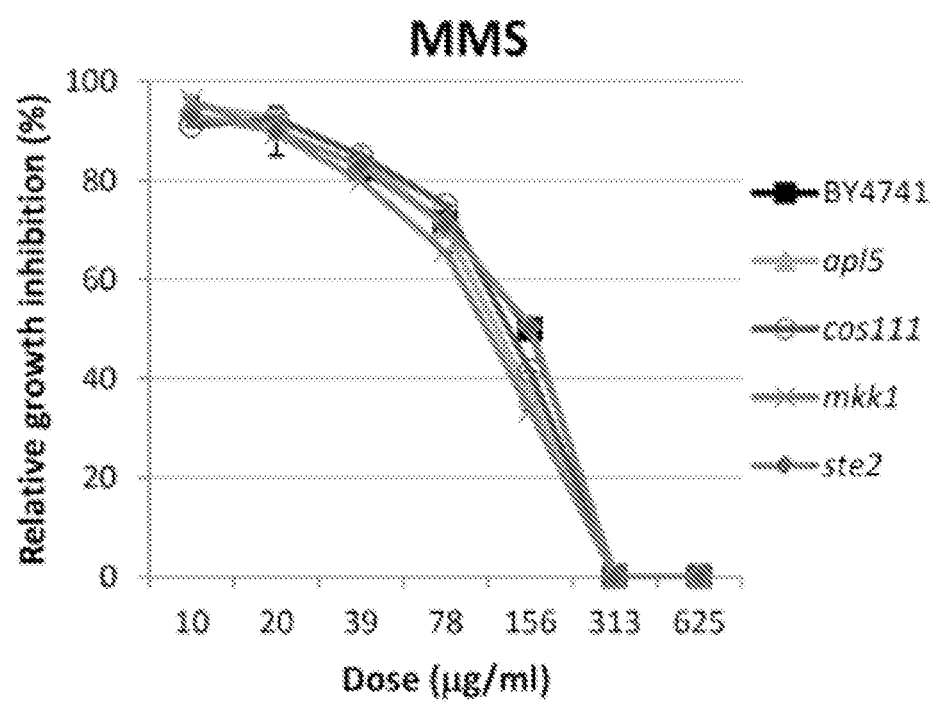

To confirm drug resistance, individual mutants along with the parent strain were grown in the presence of various concentrations of BHBM. Various concentrations of fluconazole and methyl methane sulphonate (MMS) were used as controls (FIG. 32A-C). All individual mutants showed increased resistance to BHBM in the range of 11 to 92 µg/mL (FIG. 32A), while all mutants showed similar susceptibility to fluconazole and MMS. The increased resistance of these mutants to BHBM treatment confirms that the above-mentioned genes are indeed the targets of BHBM and the absence of these targets impairs the killing activity of the drug. It is worth noting that deep sequencing analysis also revealed the presence of mutations in another gene SLA2, also involved in vesicular transport (Mulholland, J. et al. 1997). Although the Δsla2 mutant was not resistant to BHBM, it remains to be determined if point mutations within the SLA2 open reading frame do in fact confer resistance.

Discussion

There Is a major clinical need for new drugs due to a dramatic increase of morbidity and mortality by invasive fungal infections. Using *C. neoformans* as a model organism, a ChemBridge synthetic library of ~50,000 compounds and looked for inhibitors of cryptococcal growth at neutral and alkaline pH and select those compounds that inhibited GlcCer synthesis. Two compounds were identified (BHBM and 1) that decreased the synthesis of GlcCer in *C. neoformans* but not in mammalian cells. These compounds were effective in vitro against a series of pathogenic fungi, protect mice from cryptococcal meningitis, invasive candidiasis and significantly decrease lung burden of *P. murina*, the murine model of human pneumocystosis. The compounds had limited toxicity in vitro, were well tolerated in animals and possess acceptable pharmacokinetic properties. Mechanistic studies revealed that the compounds may target enzymes involved in the transport of vesicles between ER and Golgi, which is the main mechanism by which ceramide is transported for the synthesis of GlcCer. It was also found that these compounds may affect the function of enzymes involved in cell cycle progression and cell division, further confirming the key role of GlcCer in the regulation of these fungal cellular processes. Finally, in vitro resistance was not developed and a strong synergistic or additive effect was observed.

Without being limited by a particular theory, the compounds contained herein decrease the synthesis of fungal but not mammalian GlcCer. This action seems to be specific to the transport of fungal ceramide species. The compounds are active in vitro against fungi, especially *C. neoformans, P. murina, P. jiroveci, R. oryzae*, and dimorphic fungi. The compounds appear to be effective in vivo against cryptococcosis, candidiasis and also against pneumocystosis. However, some toxicity emerged when BHBM was combined with corticosteroids. The compounds do not induce resistance in vitro and they are synergistic with existing antifungals.

*C. albicans* is resistant in vitro but not in vivo. Studies performed in this fungus have suggested that GlcCer is important for virulence but through a mechanism other than facilitating growth at neutral/alkaline pH (33), which is the pH used to screen our ChemBridge library. Hence, inhibition of GlcCer in *C. albicans* by BHBM does not block fungal growth in vitro. However, because the compound still decreases GlcCer synthesis, which is required for *Candida* virulence, the treatment is effective in partially protecting mice from invasive candidiasis. These findings support previous studies suggesting that the effect of GlcCer in vivo during *Candida* infection goes beyond the regulation of fungal alkaline tolerance.

A recent paper describes the synthesis of isoniazid derivatives and their antifungal action against *H. capsulatum* (de Aguiar Cordeiro, R. et al. 2014). These compounds decrease the synthesis of ergosterol in *H. capsulatum*, although not as dramatic as itraconazole does (de Aguiar Cordeiro, R. et al. 2014). In contrast, the present compounds do not decrease the synthesis of ergosterol (FIG. 28).

The lead compounds possess a good selectivity index ($EC_{50}$/MIC>50) although we hope that this index can be significantly improved by the synthesis of new derivatives. Data showing that some derivatives that we already produced have much better solubility, at least in vitro, suggest the possibility that compounds with higher selectivity index can be produced. Of interest was the change in the phenolic OH group in BMBH, alkylation of this group (Compound 2) resulted in the loss of activity. This implicated that a hydrogen promoter may be relevant to activity. Replacement of the bromo-substituent by hydrogen resulted in an inactive molecule (Compound 3, Compound 7) implying that the phenol group alone is not sufficient and that a bulky hydrophobic group might be required. In the absence of the bromo substituent, replacement of the phenolic group by dimethylamino also renders an active molecule (Compound 4, Compound 8). Surprisingly, introducing two hydroxyl groups in positions 2 and 4 (Compound 5, Compound 9) resulted in 32% or 9.6% antifungal activity when based on BMBH and 1, respectively. The 2-OH group probably forms an intra-molecular hydrogen bond to the Schiff base nitrogen. Unexpectedly, the 4-methoxy derivatives still retained antifungal activity; the BMBH-derived analog was slightly less active (20%) than the hydroxyl form, whereas the activity of the 1-derived analog improved significantly to 19%. Compound 5 is 30-fold more water-soluble than BHBM.

Both BHBM and 1 inhibit GlcCer synthesis; however, this lipid is most likely not the only target of these compounds. In fact, the blockage of fungal growth in alkaline pH due to the loss of GlcCer (Δgcs1 mutant) can be restored if Δgcs1 cells are shifted to an acidic environment (Singh A. et al. 2012). This can occur even after the cells are left in cell cycle arrest for 72 hours. This means that the lack of GlcCer has a "static" effect on cell growth. But BHBM, and more efficiently 1, kills fungal cells. One explanation for this effect is found by analyzing the HIP-HOP results, in which several genes/enzymes affected by BHBM are essential (Table 3). Additionally, treatment with BHBM or 1 acutely leads to the accumulation of sphingosines (FIG. 6A), which is highly toxic to fungal cells (Chung, N. et al. 2001; Chung, N. et al. 2000). The accumulation of sphingosine species is not present when Gcs1 is deleted (Rittershaus, P. C. 2006) or in mammalian cells treated with BHBM or 1. Thus, the effect of BHBM seems to go beyond the inhibition of GlcCer and this may account for the fungal killing effect exerted by the drugs and not by the absence of GlcCer.

In addition, the observation that BHBM reduces the intracellular proliferation of *C. neoformans* within macrophages (acidic environment) also suggests that the effect of the drug goes beyond its in vitro activity at neutral and alkaline pH. Perhaps the effect of BHBM on reducing vesicular secretion, which is not linked to the pH of the medium, is responsible for the growth inhibition of internalized fungi because secreted vesicles are virulence bags that can protects the fungus against host cells (Rodrigues, M. L. et al. 2008).

Our toxicity and PK studies revealed that both BHBM and 1 are, in general, well tolerated. However, serum half-life ($T_{1/2}$), $C_{max}$ and $AUC_{0-t}$ are low at the dose regimes used. These doses were selected because they were effective in protecting against *C. neoformans* and *C. albicans* infections. It is likely that soon after the administration the drug promptly leaves the bloodstream and concentrates in specific organs and tissues. Preliminary results on tissue distribution revealed that BHBM is found in the brain. This suggest not only that the drug crosses the blood-brain barrier but it may also explain the low serum half-life and $C_{max}$. Once maximum tolerated dosages (MTDs) are determined, PK parameters and tissue distribution will be better assessed. However, the compounds seem to be well tolerated and, after 60 days of treatment, mice only presented a slightly increased level of liver AST.

The study and the characterization of the genes identified by the HIP-HOP screening does reveal not only the mechanism of action of the present compounds but also new means by which GlcCer and other complex sphingolipids (e.g. IPC) are synthesized in fungal cells. The fungal GlcCer synthetic pathway appears to be highly specialized because BHBM does not block the synthesis of mammalian GlcCer (FIG. 1A and FIG. 26) or the synthesis of fungal IPC (data not shown), which also occurs in the Golgi. In fact, in addition to GlcCer, most fungi also make another glycosphingolipid in the Golgi called inositol phorphorylceramides (IPCs and its derivatives). These lipids are synthesized from different ceramide species named "phytoceramides" (Del Poeta, M. et al. 2014; Nimrichter, L. et al. 2011; Rittenour, W. R. et al. 2011). Since BHBM does not decrease the level of IPC, it suggests that the vesicles involved in transporting methylated ceramides may be different than those transporting phytoceramides. This type of specialization seems to be present also in mammalian cells, in which inhibition of the transport of certain species of ceramide (very long chain) decreases GlcCer but not sphingomyelin levels (Loizides-Mangold, U. et al. 2012). This means that there is a high specialization in the transport of ceramide species between the ER and the Golgi and, thus, it is possible to specifically target one transport without affecting the other(s). The effect of the present compounds on ER-Golgi vesicles is supported by their additive or synergistic action when combined with tunicamycin, an inhibitor of N-linked glycosylation and an ER vesicle stress inducer.

The specificity in inhibiting the transport of cellular vesicles is further supported by the visualization of labeled ceramide in fungal cells treated and untreated with BHBM and by the inhibition of secreted vesicles (FIG. 7). These studies indicate that BHBM not only inhibits intracellular vesicular transport of ceramide but also the secretion of vesicles extr In summary, new molecules were identified that target the synthesis of fungal but not mammalian GlcCer. These hydrazycins have potent antifungal activity in vitro and in vivo against a variety of clinically important fungi. They also displayed synergistic action with current antifungals, low toxicity, favorable PK parameters, and fungal specific mechanisms of action.

REFERENCES

Aerts A M, et al. The antifungal activity of RsAFP2, a plant defensin from *raphanus sativus*, involves the induction of reactive oxygen species in *Candida albicans*. *J Mol Microbiol Biotechnol.* 2007; 13(4):243-7.

Albuquerque P C, et al. Vesicular transport in *Histoplasma capsulatum*: an effective mechanism for trans-cell wall transfer of proteins and lipids in ascomycetes. *Cell Microbiol.* 2008; 10(8):1695-710.

Alvarez M, and Casadevall A. Phagosome Extrusion and Host-Cell Survival after *Cryptococcus neoformans* Phagocytosis by Macrophages. *Curr Biol.* 2006; 16(21):2161-5.

Aoki K, Newly discovered neutral glycosphingolipids in aureobasidin A-resistant zygomycetes: Identification of a novel family of Gala-series glycolipids with core Gal alpha 1-6Gal beta 1-6Gal beta sequences. *J Biol Chem.* 2004; 279(31):32028-34.

Asleson, C. M., et al. *Candida albicans* INT1-induced filamentation in *Saccharomyces cerevisiae* depends on Sla2p. Molecular and cellular biology 21, 1272-1284 (2001).

Barchiesi, F., et al. Interactions between triazoles and amphotericin B against *Cryptococcus neoformans*. Antimicrobial agents and chemotherapy 44, 2435-2441 (2000).

Benfield T, et al. Second-line salvage treatment of AIDS-associated *Pneumocystis jirovecii* pneumonia: a case series and systematic review. *J Acquir Immune Defic Syndr.* 2008; 48(1):63-7.

Bligh E G, and Dyer W J. A rapid method for total lipid extraction and purification. *Can J Bioch Physiol.* 1959; 37; 911-7.

Brown G D, Denning D W, Gow N A, Levitz S M, Netea M G, and White T C. Hidden killers: human fungal infections. *Sci Transl Med.* 2012; 4(165):165rv13.

Bryant, N.J. & Stevens, T. H. Vacuole biogenesis in *Saccharomyces cerevisiae*: protein transport pathways to the yeast vacuole. Microbiology and molecular biology reviews: MMBR 62, 230-247 (1998).

Carmona E M, and Limper A H. Update on the diagnosis and treatment of *Pneumocystis* pneumonia. *Ther Adv Respir Dis.* 2011; 5(1):41-59.

Chamilos G, Lewis R E, and Kontoyiannis D P. Lovastatin has significant activity against zygomycetes and interacts synergistically with voriconazole. *Antimicrob Agents Chemother.* 2006; 50(1):96-103.

Chung N, Mao C, Heitman J, Hannun Y A, and Obeid L M. Phytosphingosine as a specific inhibitor of growth and nutrient import in *Saccharomyces cerevisiae*. *J Biol Chem.* 2001; 276(38):35614-21.

Chung N, and Obeid L M. Use of yeast as a model system for studies of sphingolipid metabolism and signaling. *Methods Enzymol.* 2000; 311(8):319-31.

Colosi I A, et al. Susceptibility of 100 filamentous fungi: comparison of two diffusion methods, Neo-Sensitabs and E-test, for amphotericin B, caspofungin, itraconazole, voriconazole and posaconazole. *Med Mycol.* 2012; 50(4):378-85.

Cushion M T, et al. Transcriptome of *Pneumocystis carinii* during fulminate infection: carbohydrate metabolism and the concept of a compatible parasite. *PLoS One.* 2007; 2(5):e423.

da Silva A F, et al. Glucosylceramides in *Colletotrichum gloeosporioides* are involved in the differentiation of conidia into mycelial cells. *FEBS Lett.* 2004; 561(1-3):137-43.

Dannaoui E, et al. In vitro susceptibilities of zygomycetes to conventional and new antifungals. *J Antimicrob Chemother.* 2003; 51(1):45-52.

de Aguiar Cordeiro R, et al. Synthesis and antifungal activity in vitro of isoniazid derivatives against *Histoplasma capsulatum* var. *capsulatum*. *Antimicrob Agents Chemother.* 2014; 58(5):2504-11.

de Medeiros L N, et al. Backbone dynamics of the antifungal Psd1 pea defensin and its correlation with membrane interaction by NMR spectroscopy. *Biochim Biophys Acta.* 2010; 1798(2):105-13.

DePristo, M. A., et al. A framework for variation discovery and genotyping using next-generation DNA sequencing data. Nature genetics 43, 491-498 (2011).

Del Poeta M, Nimrichter L, Rodrigues M L, and Luberto C. Synthesis and biological properties of fungal glucosylceramide. *PLoS Pathog.* 2014; 10(1):e1003832.

Del Poeta M, et al. Synergistic antifungal activities of bafilomycin A(l), fluconazole, and the pneumocandin MK-0991/Caspofungin acetate (L-743,873) with calcineurin inhibitors FK506 and L-685,818 against *Cryptococcus neoformans*. *Antimicrob Agents Chemother.* 2000; 44(3):739-46.

Farnoud, A. M., Mor, V., Singh, A. & Del Poeta, M. Inositol phosphosphingolipid phospholipase C1 regulates plasma membrane ATPase (Pma1) stability in *Cryptococcus neoformans*. FEES letters (2014).

Farowski F, et al. Intracellular concentrations of micafungin in different cellular compartments of the peripheral blood. *Int J Antimicrob Agents.* 2012; 39(3):228-31.

Farowski F, et al. Intracellular concentrations of anidulafungin in different compartments of the peripheral blood. *Int J Antimicrob Agents.* 2013; 41(4):379-82.

Funato K, and Riezman H. Vesicular and nonvesicular transport of ceramide from ER to the Golgi apparatus in yeast. *J Cell Biol.* 2001; 155(6):949-59.

Fungal Infection Trust, How common are fungal diseases? *Fungal Research Trust 20th Anniversary Meeting*. Fungal Infection Trust/London. June 18th 2011, updated December 2012.

Gale, C. A., et al. SLA2 mutations cause SWE1-mediated cell cycle phenotypes in *Candida albicans* and *Saccharomyces cerevisiae*. *Microbiology* 155, 3847-3859 (2009).

Gallis, H. A., Drew, R. H. & Pickard, W. W. Amphotericin B: 30 years of clinical experience. Review of Infectious Diseases 12, 308-329 (1990).

Garcia, J., et al. Mathematical modeling of pathogenicity of *Cryptococcus neoformans*. Molecular System Biology 4, 183-195 (2008).

Garcia-Rodas R, et al. Capsule Growth in *Cryptococcus neoformans* Is Coordinated with Cell Cycle Progression. *MBio.* 2014/5(3).

Goncalves S, Abade J, Teixeira A, and Santos N C. Lipid composition is a determinant for human defensin HNP1 selectivity. *Biopolymers.* 2012/98(4):313-21.

Gottfried, I., Ehrlich, M. & Ashery, U. The Sla2p/HIP1/HIP1R family: similar structure, similar function in endocytosis? Biochemical Society transactions 38, 187-191 (2010).

Gourlay, C. W., et al. An interaction between Sla1p and Sla2p plays a role in regulating actin dynamics and endocytosis in budding yeast. Journal of cell science 116, 2551-2564 (2003).

Graybill, J. R., Williams, D. M., Van Cutsem, E. & Drutz, D. J. Combination therapy of experimental histoplasmosis and cryptococcosis with amphotericin B and ketoconazole. Review of Infectious Diseases 2, 551-558 (1980).

Guery B P, et al. Management of Invasive candidiasis and candidemia in adult non-neutropenic intensive care unit patients: Part I. Epidemiology and diagnosis. *Intensive Care Med.* 2009; 35(1):55-62.

Gullo A. Invasive fungal infections: the challenge continues. *Drugs.* 2009; 69 Suppl 1, 65-73.

Henry, J., Guillotte, A., Luberto, C. 6 Del Poeta, M. Characterization of inositol phospho-sphingolipid-phospholipase C 1 (Isc1) in *Cryptococcus neoformans* reveals unique biochemical features. FEES letters 585, 635-640 (2011).

Heung L J, Luberto C, and Del Poeta M. Role of sphingolipids in microbial pathogenesis. *Infect Immun.* 2006; 74(1):28-39.

Heung, L. J., Kaiser, A. E., Luberto, C. 6 Del Poeta, M. The role and mechanism of diacylglycerol-protein kinase C1 signaling in melanogenesis by *Cryptococcus neoformans*. *J. Biol. Chem.* 280, 28547-28555 (2005).

Hoffman. C. S., Winston, F. A ten-minute DMA preparation from yeast efficiently releases autonomous plasmids for transformation of *Escherichia coli*. Gene 57:267-272 (1987).

Hua, Z. 6 Graham, T. R. Requirement for neo1p in retrograde transport from the Golgi complex to the endoplasmic reticulum. Molecular biology of the cell 14, 4971-4983 (2003).

Huang L, Morris A, Limper A H, Beck J M, and Participants ATSPW. An Official ATS Workshop Summary: Recent advances and future directions in pneumocystis pneumonia (PCP). *Proc Am Thorac Soc.* 2006; 3(8):655-64.

Huang Z, et al. A functional variomics tool for discovering drug-resistance genes and drug targets. *Cell Rep.* 2013; 3(2):577-85.

Huang Z, et al. Sampangine inhibits heme biosynthesis in both yeast and human. *Eukaryot Cell.* 2011; 10(11):1536-44.

Ishibashi Y, et al. Quality control of fungus-specific glucosylceramide in *Cryptococcus neoformans* by endoglycoceramidase-related protein 1 (EGCrP1). *J Biol Chem.* 2012; 287(1):368-81.

Jarmoszewicz, K., Lukasiak, K., Riezman, H. & Kaminska, J. Rsp5 ubiquitin ligase is required for protein trafficking in *Saccharomyces cerevisiae* COPI mutants. PloS one 7, e39582 (2012).

Kajiwara K, et al. Osh proteins regulate COPII-mediated vesicular transport of ceramide from the endoplasmic reticulum in budding yeast. *J Cell Sci.* 2014; 127(Pt 2):376-87.

Kazanjian P, et al. *Pneumocystis carinii* cytochrome b mutations are associated with atovaquone exposure in patients with AIDS. *J Infect Dis.* 2001; 183(5):819-22.

Kechichian T B, et al. Depletion of alveolar macrophages decreases the dissemination of a glucosylceramide-deficient mutant of *Cryptococcus neoformans* in immunodeficient mice. *Infect Immun.* 2007/75(10):4792-8.

Kelley C F, et al. Trends in hospitalizations for AIDS-associated *Pneumocystis jirovecii* Pneumonia in the United States (1986 to 2005). Chest. 2009; 136(1):190-197.

Kmetzsch L, et al. Role for Golgi reassembly and stacking protein (GRASP) in polysaccharide secretion and fungal virulence. *Mol Microbiol.* 2011; 81(1):206-18.

Larsen, R. A., Leal, M. A. E. & Chan, L. S. Fluconazole Compared with Amphotericin B plus Flucytosine for Cryptococcal Meningitis in AIDSA Randomized Trial. *Annals of Internal Medicine* 113, 183-187 (1990).

Lee A Y, et al. Mapping the cellular response to small molecules using chemogenomic fitness signatures. *Science*. 2014/344(6180):208-11.

Levery S B, et al. Disruption of the glucosylceramide biosynthetic pathway in *Aspergillus nidulans* and *Aspergillus fumigatus* by inhibitors of UDP-Glc:ceramide glucosyltransferase strongly affects spore germination, cell cycle, and hyphal growth. *FEBS Lett.* 2002; 525(1-3):59-64.

Li, R, et al. SOAP2: an improved ultrafast tool for short read alignment. Bioinformatics 25:1966-1967 (2009).

Li, H. & Durbin, R. Fast and accurate short read alignment with Burrows-Wheeler transform. Bioinformatics 25, 1754-1760 (2009).

Liu O W, Chun C D, Chow E D, Chen C, Madhani H D, and Noble S M. Systematic genetic analysis of virulence in the human fungal pathogen *Cryptococcus neoformans*. *Cell.* 2008; 135(1):174-88.

Lobo D S, et al. Antifungal *Pisum sativum* defensin 1 interacts with *Neurospora crassa* cyclin F related to the cell cycle. *Biochemistry.* 2007; 46(4):987-96.

Loizides-Mangold U, David F P, Nesatyy V J, Kinoshita T, and Riezman H. Glycosylphosphatidylinositol anchors regulate glycosphingolipid levels. *J Lipid Res.* 2012; 53(8):1522-34.

Luberto C, Toffaletti D L, Wills E A, Tucker S C, Casadevall A, Perfect J R, Hannun Y A, and Del Poeta M. Roles for inositol-phosphoryl ceramide synthase 1 (IPC1) in pathogenesis of *C. neoformans. Genes Dev.* 2001; 15(2):201-12.

Ma H, Croudace J E, Lammas D A, and May R C. Expulsion of live pathogenic yeast by macrophages. *Curr Biol.* 2006; 16(21):2156-60.

Ma L, Borio L, Masur H, and Kovacs J A. *Pneumocystis carinii* dihydropteroate synthase but not dihydrofolate reductase gene mutations correlate with prior trimethoprim-sulfamethoxazole or dapsone use. *J Infect Dis.* 1999; 180(6):1969-78.

Mandala S M, et al. The discovery of australifungin, a novel inhibitor of sphinganine N-acyltransferase from *Sporormiella australis*. Producing organism, fermentation, isolation, and biological activity. *J Antiblot (Tokyo).* 1997; 50(4):339-43.

Maschmeyer G, Haas A, and Cornely O A. Invasive aspergillosis; epidemiology, diagnosis and management in immunocompromised patients. *Drugs.* 2007; 67(11):1567-601.

Mayr A, and Lass-Florl C. Epidemiology and antifungal resistance in invasive Aspergillosis according to primary disease: review of the literature. *Eur J Med Res.* 2011; 16(4):153-7.

McCann, R. O. & Craig, S. W. The I/LWEQ module: a conserved sequence that signifies F-actin binding in functionally diverse proteins from yeast to mammals. Proceedings of the National Academy of Sciences of the United States of America 94, 5679-5684 (1997).

McKenna, A., et al. The Genome Analysis Toolkit: a MapReduce framework for analyzing next-generation DNA sequencing data. Genome research 20, 1297-1303 (2010).

Mello Ede, O., et al. Functional expression and activity of the recombinant antifungal defensin PvD1r from *Phaseolus vulgaris* L. (common bean) seeds. *BMC Biochem.* 2014; 15(1):7.

Mulholland, J., Wesp, A., Riezman, H. & Botstein, D. Yeast actin cytoskeleton mutants accumulate a new class of Golgi-derived secretory vesicle. Molecular biology of the cell 8, 1481-1499 (1997).

Munoz P, Guinea J, Narbona M T, and Bouza E. Treatment of invasive fungal infections in immunocompromised and transplant patients: AmBiLoad trial and other new data. *Int J Antimicrob Agents.* 2008; 32 Suppl 2: S125-31.

Nimrichter L, and Rodrigues M L. Fungal glucosylceramides: from structural components to biologically active targets of new antimicrobials. *Front Microbiol.* 2011; 2; 212.

Noble S M, French S, Kohn L A, Chen V, and Johnson A D. Systematic screens of a *Candida albicans* homozygous deletion library decouple morphogenetic switching and pathogenicity. *Nat Genet.* 2010; 42(7):590-8.

Nosanchuk J D, Nimrichter L, Casadevall A, and Rodrigues M L. A role for vesicular transport of macromolecules across cell walls in fungal pathogenesis. *Common Integr Biol.* 2008; 1(1):37-9.

Odabasi Z, Paetznick V, Rex J H, and Ostrosky-Zeichner L. Effects of serum on in vitro susceptibility testing of echinocandins. *Antimicrob Agents Chemother.* 2007; 51(11):4214-6.

Oguro Y, Yamazaki H, Takagi M, and Takaku H. Antifungal activity of plant defensin AFP1 in *Brassica juncea* involves the recognition of the methyl residue in glucosylceramide of target pathogen *Candida albicans. Curr Genet.* 2014; 60(2):89-97.

Oliveira D L, Freire-de-Lima C G, Nosanchuk J D, Casadevall A, Rodrigues M L, and Nimrichter L. Extracellular vesicles from *Cryptococcus neoformans* modulate macrophage functions. *Infect Immun.* 2010; 78(4):1601-9.

Oliveira D L, Nimrichter L, Miranda K, Frases S, Faull K F, Casadevall A, and Rodrigues M L. *Cryptococcus neoformans* cryoultramicrotomy and vesicle fractionation reveals an intimate association between membrane lipids and glucuronoxylomannan. *Fungal Genet Biol.* 2009; 46(12):956-63.

Oura T, and Kajiwara S. *Candida albicans* sphingolipid C9-methyltransferase is involved in hyphal elongation. Microbiology. 2010; 156(Pt 4):1234-43.

Oura T, and Kajiwara S. Disruption of the sphingolipid DeltaB-desaturase gene causes a delay in morphological changes in *Candida albicans. Microbiology.* 2008; 154(Pt 12):3795-803.

Palmer, G. E. Vacuolar trafficking and *Candida albicans* pathogenesis. Communicative & integrative biology 4, 240-242 (2011).

Pagano R E, Sepanski M A, and Martin O C. Molecular trapping of a fluorescent ceramide analogue at the Golgi apparatus of fixed cells: interaction with endogenous lipids provides a trans-Golgi marker for both light and electron microscopy. *J Cell Biol.* 1989; 109(5):2067-79.

Perlroth J, Choi B, and Spellberg B. Nosocomial fungal infections: epidemiology, diagnosis, and treatment. *Med Mycol.* 2007; 45(4):321-46.

Peterson, L., Kelty, R., Hall, W. & Votava, H. Therapy of *Candida* peritonitis: penetration of amphotericin B into peritoneal fluid. Postgraduate medical journal 54, 340-342 (1978).

Pierce S E, et al. Genome-wide analysis of barcoded *Saccharomyces cerevisiae* gene-deletion mutants in pooled cultures. *Nat Protoc.* 2007; 2(11):2958-74.

Proctor M, et al. The automated cell: compound and environment screening system (ACCESS) for chemogenomic screening. *Methods Mol Biol.* 2011; 759(239-69.

Ramamoorthy V, et al. Sphingolipid C-9 methyltransferases are important for growth and virulence but not for sensitivity to antifungal plant defensins in *Fusarium graminearum. Eukaryot Cell.* 2009; 8(2):217-29.

Reggiori F, and Conzelmann A. Biosynthesis of inositol phosphoceramides and remodeling of glycosylphosphatidylinositol anchors in *Saccharomyces cerevisiae* are mediated by different enzymes. *J Biol Chem.* 1998; 273 (46):30550-9.

Rhome R, et al. Biosynthesis and immunogenicity of glucosylceramide in *Cryptococcus neoformans* and other human pathogens. *Eukaryot Cell.* 2007; 6(10):1715-26.

Rhome R, et al. Surface localization of glucosylceramide during *Cryptococcus neoformans* infection allows targeting as a potential antifungal. *PLoS One.* 2011; 6(1): e15572.

Rittenour W R, et al. Control of glucosylceramide production and morphogenesis by the Bari ceramide synthase in *Fusarium graminearum. PLoS One.* 2011; 6(4):e19385.

Rittershaus P C, et al. Glucosylceramide is an essential regulator of pathogenicity of *Cryptococcus neoformans*. *J Clin Invest*. 2006; 116(6):1651-9.

Rizzo J, et al. Role of the Apt1 protein in polysaccharide secretion by *Cryptococcus neoformans*. *Eukaryot Cell*. 2014; 13(6):715-26.

Rodrigues M L, Nimrichter L, Oliveira D L, Nosanchuk J D, and Casadevall A. Vesicular Trans-Cell Wall Transport in Fungi: A Mechanism for the Delivery of Virulence-Associated Macromolecules? *Lipid Insights*. 2008; 2; 27-40.

Rodrigues M L, and Djordjevic J T. Unravelling secretion in *Cryptococcus neoformans*: more than one way to skin a cat. *Mycopathologia*. 2012/173(5-6):407-18.

Rodrigues M L, Nakayasu E S, Oliveira D L, Nimrichter L, Nosanchuk J D, Almeida I C, and Casadevall A. Extracellular vesicles produced by *Cryptococcus neoformans* contain protein components associated with virulence. *Eukaryot Cell*. 2008; 7(1):58-67.

Rodrigues, M. L., et al. Vesicular polysaccharide export in *Cryptococcus neoformans* is a eukaryotic solution to the problem of fungal trans-cell wall transport. *Eukaryotic cell* 6, 48-59 (2007).

Rogers T R. Treatment of zygomycosis: current and new options. *J Antimicrob Chemother*. 2008; 61 Suppl 1(135-40.

Rueping M J, eInvasive candidiasis and candidemia: from current opinions to future perspectives. *Expert Opin Investig Drugs*. 2009; 18(6):735-48.

Ruping M J, Vehreschild J J, and Comely O A. Patients at high risk of invasive fungal infections: when and how to treat. *Drugs*. 2008; 68(14):1941-62.

Saito K, Takakuwa N, Ohnishi M, and Oda Y. Presence of glucosylceramide in yeast and its relation to alkali tolerance of yeast. *Appl Microbiol Biotechnol*. 2006; 69:1-7.

Salama, N. R., Chuang, J. S. & Schekman, R. W. Sec31 encodes an essential component of the COPII coat required for transport vesicle budding from the endoplasmic reticulum. *Molecular biology of the cell* 8, 205-217 (1997).

Saribas Z, Yurdakul P, Cetin-Hazirolan G, and Arikan-Akdagli S. Influence of serum on in vitro susceptibility testing of echinocandins for *Candida parapsilosis* and *Candida guilliermondii*. *Mycoses*. 2012; 55(2):156-60.

Saunders, C. T., et al. Strelka: accurate somatic small-variant calling from sequenced tumor-normal sample pairs. *Bioinformatics* 28, 1811-1817 (2012).

Sawaya, B. P., Briggs, J. P. & Schnermann, J. Amphotericin B nephrotoxicity: the adverse consequences of altered membrane properties. *Journal of the American Society of Nephrology* 6, 154-164 (1995).

Shea, J., Kechichian, T. B., Luberto, C. 6 Del Poeta, M. The cryptococcal enzyme inositol phosphosphingolipid-phospholipase C (Isc1) confers resistance to the antifungal effects of macrophages and promotes fungal dissemination to the central nervous system. *Infection and immunity* 74, 5977-5988 (2006).

Singh A, and Del Poeta M. Lipid signalling in pathogenic fungi. *Cellular microbiology*. 2011; 13(2):177-85.

Singh A, Na C, Silva L C, Prieto M, Futerman A H, Luberto C, and Del Poeta M. Membrane lipid topography controlled by sphingolipids regulates pathogenicity of *Cryptococcus neoformans*. *Cellular Microbiology*. 2012; 14(4):500-16.

Singh J, Rimek D, and Kappe R. In vitro susceptibility of 15 strains of zygomycetes to nine antifungal agents as determined by the NCCLS M38-A microdilution method. *Mycoses*. 2005; 48(4):246-50.

Sorrell T C, Chen SC-A, Phillips P, and Marr K A. In: Heitman J, Kozel T R, Kwon-Chung K J, Perfect J, and Casadevall A eds. *Cryptococcus: from human pathogen to model yeast*. Washington, D C: ASM; 2011:595-606.

Suzuki, Y., et al. Knocking out multigene redundancies via cycles of sexual assortment and fluorescence selection. *Nature methods* 8, 159-164 (2011).

Tavares P M, et al. In vitro activity of the antifungal plant defensin RsAFP2 against *Candida* isolates and its in vivo efficacy in prophylactic murine models of candidiasis. *Antimicrob Agents Chemother*. 2008; 52(12):4522-5.

Thevissen K, et al. The plant defensin RsAFP2 induces cell wall stress, septin mislocalization and accumulation of ceramides in *Candida albicans*. *Mol Microbiol*. 2012; 84(1):166-80.

Thevissen K, et al. Defensins from insects and plants interact with fungal glucosylceramides. *J Biol Chem*. 2004; 279(6):3900-5.

Toledo M S, et al. Characterization of cerebrosides from the thermally dimorphic mycopathogen *Histoplasma capsulatum*: expression of 2-hydroxy fatty N-acyl (E)-Delta(3)-unsaturation correlates with the yeast-mycelium phase transition. *Glycobiology*. 2001; 11(2):113-24.

Tucker, R., et al. Pharmacokinetics of fluconazole in cerebrospinal fluid and serum in human coccidioidal meningitis. *Antimicrobial agents and chemotherapy* 32, 369-373 (1988).

Tuite N L, and Lacey K. Overview of invasive fungal infections. *Methods Mol Biol*. 2013; 968, 1-23.

Vallejo M C, et al. The pathogenic fungus Paracoccidioides brasiliensis exports extracellular vesicles containing highly immunogenic alpha-Galactosyl epitopes. *Eukaryot Cell*. 2011; 10(3):343-51.

Warnecke D, and Heinz E. Recently discovered functions of glucosylceramides in plants and fungi. *Cell Mol Life Sci*. 2003; 60(5):919-41.

Webb, G. C., et al. Pep7p provides a novel protein that functions in vesicle-mediated transport between the yeast Golgi and endosome. *Molecular biology of the cell* 8, 871-895 (1997).

Wesp, A., et al. End4p/Sla2p interacts with actin-associated proteins for endocytosis in *Saccharomyces cerevisiae*. *Molecular biology of the cell* 8, 2291-2306 (1997).

World Health Organization. World Malaria Report 2013—http://www.who.int/malaria/publications/world_malaria_report_2013/en/. Accessed Dec. 11, 2013.

World Health Organization. Global Tuberculosis Report 2013—http://www.who.int/tb/publications/global_report/en/. Accessed November 2013.

Yanni S B, et al. Higher clearance of micafungin in neonates compared with adults: role of age-dependent micafungin serum binding. *Biopharm Drug Dispos*. 2011; 32(4):222-32.

Yang, S., Cope, M. J. & Drubin, D. G. Sla2p is associated with the yeast cortical actin cytoskeleton via redundant localization signals. *Molecular biology of the cell* 10, 2265-2283 (1999).

The invention claimed is:

1. A compound having the structure:

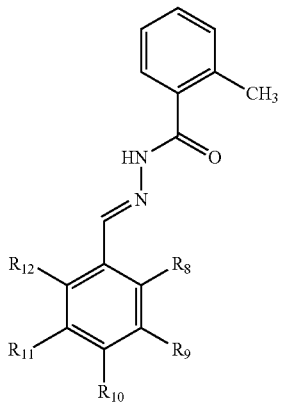

wherein
$R_8$=—OH,
$R_9$ and $R_{11}$ are each —H,
$R_{10}$ is —N(CH$_3$)$_2$,
$R_{12}$=—H; or

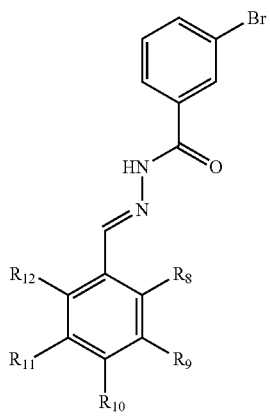

wherein
R8=—OH,
$R_9$ and $R_{11}$ are each independently —H or —Br,
$R_{10}$ is —N(CH$_3$)$_2$,
$R_{12}$=—H,
or a pharmaceutically acceptable salt thereof.

2. A compound having the structure:

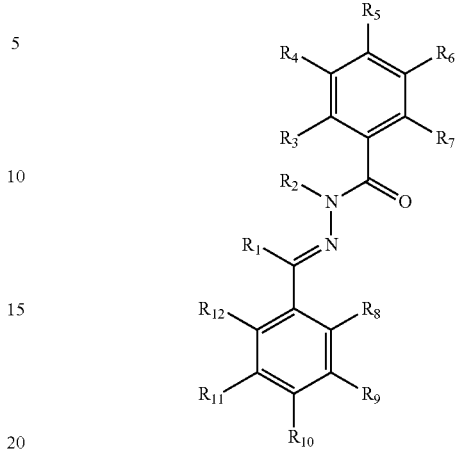

wherein
$R_1$ is —H;
$R_2$ is —H;
$R_3$, $R_4$, $R_6$ and $R_7$ are each —H, —Br, or —OH;
$R_5$ is —COR$_{13}$, wherein $R_{13}$ is alkyl;
$R_8$ is —OH;
$R_9$, $R_{13}$, $R_{11}$ and $R_{12}$ are each —H, —Br, —Cl, alkynyl, or —OH,
wherein at least two of $R_8$, $R_9$, $R_{10}$, $R_{11}$ and $R_{12}$ are other than —H, or a pharmaceutically acceptable salt thereof.

3. A pharmaceutical composition comprising the compound of claim 1 and a pharmaceutically acceptable carrier.

4. A pharmaceutical composition comprising the compound of claim 2 and a pharmaceutically acceptable carrier.

5. A pharmaceutical composition comprising the compound of claim 2, an antifungal agent and a pharmaceutically acceptable carrier.

6. The pharmaceutical composition of claim 5, wherein the antifungal agent is fluconazole, amphotericin B, caspofungin, tunicamycin or aureobasidin A.

7. A method of inhibiting the growth of or of killing a fungus comprising contacting the fungus with an effective amount of the compound of claim 2 or a pharmaceutically acceptable salt thereof, so as to thereby inhibit the growth of or kill the fungus.

8. A method of inhibiting fungal shingolipid synthesis in a fungus comprising contacting the fungus with an effective amount of the compound of claim 2 or a pharmaceutically acceptable salt thereof, so as to thereby inhibit fungal shingolipid synthesis in the fungus.

9. A method of inhibiting fungal shingolipid synthesis in a fungus in a mammal without substantially inhibiting mammalian shingolipid synthesis comprising administering to the mammal an effective amount of the compound of claim 2 or a pharmaceutically acceptable salt thereof, so as to thereby inhibit fungal shingolipid synthesis in the fungus in the mammal without inhibiting mammalian shingolipid synthesis.

10. A method of inhibiting the growth of or of killing a fungus comprising contacting the fungus with an effective amount of the compound of claim 2 or a pharmaceutically acceptable salt thereof and an antifungal agent, so as to thereby inhibit the growth of or kill the fungus.

11. The method of claim 10, wherein the antifungal agent is fluconazole, amphotericin B, caspofungin, tunicamycin or aureobasidin A.

12. A compound having the structure:

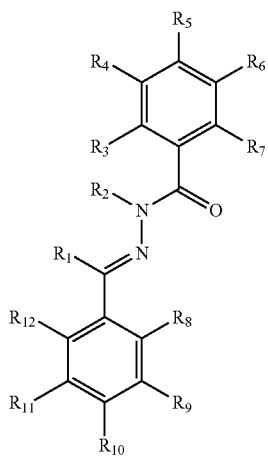

wherein
R$_1$ is —H;
R$_2$ is —H;
R$_5$ is —Br;
R$_3$, R$_4$, R$_6$ and R$_7$ are —H, —Br or —OH;
R$_8$ is —OH;
R$_9$, R$_{10}$, R$_{11}$ and R$_{12}$ are each —H, —Br, —Cl, alkynyl or —OH,
wherein at least one of R$_{10}$ or R$_{11}$ is alkynyl,
or a pharmaceutically acceptable salt thereof.

13. A method of inhibiting the growth of or killing a fungus comprising contacting the fungus with an effective amount of the compound of claim 12
or a pharmaceutically acceptable salt thereof,
so as to thereby inhibit the growth of or kill the fungus.

* * * * *